United States Patent
Reed et al.

(10) Patent No.: US 6,419,933 B1
(45) Date of Patent: *Jul. 16, 2002

(54) **COMPOUNDS AND METHODS FOR THE DETECTION AND PREVENTION OF *T.CRUZI* INFECTION**

(75) Inventors: Steven G. Reed, Bellevue; Yasir A. W. Skeiky; Michael J. Lodes, both of Seattle; Raymond L. Houghton, Bothell; John M. Smith, Everett; Patricia D. McNeill, Des Moines, all of WA (US)

(73) Assignee: Corixa Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/256,976

(22) Filed: Feb. 24, 1999

Related U.S. Application Data

(63) Continuation-in-part of application No. 08/993,674, filed on Dec. 18, 1997, which is a continuation-in-part of application No. 08/834,306, filed on Apr. 15, 1997, which is a continuation-in-part of application No. PCT/US96/18624, filed on Nov. 14, 1996, now Pat. No. 6,054,135, which is a continuation-in-part of application No. 08/557,309, filed on Nov. 14, 1995, now Pat. No. 5,916,572.

(51) Int. Cl.$^7$ ............................................. A61K 39/002
(52) U.S. Cl. ............................... 424/269.1; 424/185.1; 424/191.1; 424/192.1; 424/193.1; 530/300; 530/350; 435/69.1
(58) Field of Search .................. 530/350; 424/269.1, 424/185.1, 192.1, 193.1, 191.1; 435/69.1, 7.4

(56) References Cited

U.S. PATENT DOCUMENTS

| | | | |
|---|---|---|---|
| 4,870,006 A | 9/1989 | Dragon et al. | 435/7.22 |
| 5,304,371 A | 4/1994 | Reed | 424/88 |

FOREIGN PATENT DOCUMENTS

| | | |
|---|---|---|
| WO | 90/02564 | 3/1990 |
| WO | 92/09895 | 6/1992 |
| WO | 93/16199 | 8/1993 |
| WO | 94/01776 | 1/1994 |
| WO | 96/29605 | 9/1996 |
| WO | 97/18475 | 5/1997 |
| WO | 99/31246 | 6/1999 |

OTHER PUBLICATIONS

Bastos et al., "Use of recombinant peptide antigens of Trypanosoma cruzi in a diagnostic test for Charga's disease," *Memorias Do Instituto Oswaldo Cruz* 93(Suppl. II):286–287, Nov. 1998.

Campana et al., "Evaluation of specific Synthetic peptide combinations in serodiagnosis of Chagas' disease," *Mem. Inst. Oswaldo cruz.* 93(Suppl. II):234–235, Nov. 1998.

Houghton et al., Multiepitope synthetic peptide and recombinant protein for the detection of antibodies to Tryanosoma cruzi in patients with treated and untreated Changa's disease, *The Journal of Infectious Diseases* 181(1):325–330, Jan. 2000.

Buschiazzo et al., "Sequence of the gene for a Trypanosoma cruzi protein antigenic during the chronic phase of human Chagas disease," *Molecular and Biochemical Parasitology* 54: 125–128, 1992.

Campetella et al., "A Superfamily of Trypanosoma cruzi Surface Antigens," *Parasitology Today* 8:11, 378–381, 1992.

Frasch and Reyes, "Diagnosis of Chagas Disease Using Recombinant DNA Technology," *Parasitology Today* 6:4, 137–139, 1990.

Frasch et al., "Comparison of Genes Encoding Trypanosoma cruzi Antigens," *Parasitology Today* 7:6, 148–151, 1991.

Hoft et al., "Trypanosoma cruzi Expresses Diverse Repetitive Protein Antigens," *Infect. And Immunity* 57:7, 1959–1967, 1989.

Ibanez et al., "Multiple Trypanosoma cruzi antigens containing tandemly repeated amino acid sequence motifs," *Molecular and Biochemical Parasitology* 30: 27–34, 1988.

Peralta et al., "Serodiagnosis of Chagas'0 Disease By Enzyme Linked Immunosobent Assay Using Two Synthetic Peptides as Antigens," *Journal of Clinical Microbiology* 32:4, 971–974, 1992.

Skeiky et al., "Antigens Shared by *Leishmania* Species and *Trypanosoma cruzi*: Immunological Comparison of the acidic Ribosomal P0 Proteins," *Infection and Immunity* 62(5): 1643–1651, 1994.

Skeiky et al., "Cloning and Expression of *Trypanosoma cruzi* Ribosomal Protein P0 and Epitope Analysis of Anti–P0 Autoantibodies in Chagas' Patients," *J. Exp. Med.* 176: 201–211, 1992.

Skeiky et al., "*Trypanosoma cruzi* Acidic Ribosomal P Protein Gene Family," *Journal of Immunology* 15(10): 5504–5515, 1993.

Vergara et al., "Assay for Detection of Trypanosoma cruzi Antibodies in Human Sera Based on Reaction with Synthetic Peptides," *Journal of Clinical Microbiology* 29:9, 2034–2037, 1991.

Primary Examiner—Jennifer E. Graser
(74) Attorney, Agent, or Firm—Seed Intellectual Property Law Group PLLC

(57) ABSTRACT

Compounds and methods are provided for diagnosing *Trypanosoma cruzi* infection. The disclosed compounds are polypeptides, or antibodies thereto, that contain one or more epitopes of *T. cruzi* antigens. The compounds are useful in a variety of immunoassays for detecting *T. cruzi* infection. The polypeptide compounds are further useful in vaccines and pharmaceutical compositions for inducing protective immunity against Chagas' disease in individuals exposed to *T. cruzi*.

8 Claims, 10 Drawing Sheets

SEQUENCE LISTING

<160> NUMBER OF SEQ ID NOS: 95

<210> SEQ ID NO 1
<211> LENGTH: 518
<212> TYPE: DNA
<213> ORGANISM: Trypanosoma cruzi

<400> SEQUENCE: 1

```
cgggaaaaga aggctgttac gacgcacgag cttggctttg agggcgagga ctgggactac     60
gtgctggagc ggcggcgcgc ggaggtgaag gacgtgctgg ccgtcgagac ggcgcgggcg    120
ttgggactcg agcgtgagga cgtgctggag gtggaggtcg acgcagtgcc tcggagcctc    180
attgcgtttg tcacggtccg tcatccatca ctgctgagcg accgcaggtg gaagagacgc    240
tggcgcgctg cgagtacagg aaattgtggg cgctgtacga gacgcggcca ctggagtcgt    300
cagtgctgat gaggcggttt gagggcgacg actgggacct cgtggttgac aacaaccgca    360
ggaagcttga ggacgcgttc agcagggaga cggccgcgca ctgggcgtgt cgccgaggca    420
ggttgtgctt ctggactgca gggttggcag ccttctcatg gtattcaagg tgcttggatg    480
cgccatgagc gacgcagaga tcacggaacg gaccgagg                            518
```

<210> SEQ ID NO 2
<211> LENGTH: 560
<212> TYPE: DNA
<213> ORGANISM: Trypanosoma cruzi

<400> SEQUENCE: 2

```
cggcggtagt ctgcgatgct gtggaccgac gcattgaaat acacaccgtc ttcggcgttc     60 cttttttta tatgtttttt tttattgaga agatgtcttg tttgttgttg tttttttca    120 gtttttatga tacgagcagt ttgtccgact gcattcatgc agtgattggt aattctttct    180
attctttgga attatggcga tattattctt gtcttttaaa attcttacaa ccaattgtgc    240
cttagagttt cctgcttagt tgctattaac acactgttag gaacgcgaaa ccatgcagat    300
cttcgtgaag acactgacgg gcaagacgat cgcgctcgag gtggagtcca gcgacaccat    360
tgagaacgtg aaggcgaaga tccaggacaa ggagggtatc cgccggacca gcagcgcctg    420
atcttcgctg gcaagcagct ggaggacggc cgcacgctcg cagactacaa catccagaag    480
gagtccacgc tgcaccttgt gctgcgcctg cgcggcggca tgcagatctt cgtgaagaca    540
ctgacgggta aagacgatcg                                                560
```

<210> SEQ ID NO 3
<211> LENGTH: 436
<212> TYPE: DNA
<213> ORGANISM: Trypanosoma cruzi
<220> FEATURE:
<223> OTHER INFORMATION: Where n is an unknown nucleic acid

<400> SEQUENCE: 3

```
cggctgcctc ctctgcttcc ttcctcggac gtgcccgaag catggagct gcctcctctg    60 cttccttcct cggacatacc cgaaggcatg gagctgccac ctctgcttcc ttcctcggac   120
gtacccgcgg gcatggagct gacacctctg cttccttcct cggacgtgcc cgaaggcatg   180
gagctgccac ctctgcttcc ttcctcggac gtacccgcgg gcatggagct gccacctctg   240
sttccttcct cggacgtacc cgcgggcatg gagctgcctc ctctgcttcc ttcctcggac   300
gtacccgcgg rcatagagct gccacctctg atttcctncc tcggacgtac ccncaggnat   360
ggagatgnct cctctgnttc ctgcctcgga cgtncccnaa ggnatagagn tgcncctctg   420
nttcctncct cggaag                                                   436

<210> SEQ ID NO 4
<211> LENGTH: 373
<212> TYPE: DNA
<213> ORGANISM: Trypanosoma cruzi

<400> SEQUENCE: 4
cctcaggggc tcttggcgtt cctttttttc ttgttgtttt gagttttttt ttcttttgtt    60
ttggtttgtc gtctctgttt ttatgtgcgt tgttttcggt ttttcttttt gttcttcctg   120
cctgtcatgt gactagtttt atgttttcca ggccgaccgt cactcaattt ttttattttt   180
atttttattt atttatttga cccgcctttc tctgtagttt acgagagttt agatttttat   240
tgattggtag tttagggcca tcaggcggga ggggcgagtc tggcggaaga caaaacaaaa   300
tacgatggac tcgaccaaca gcatcgagaa atcgcttctg atggagatgg agcgggaggt   360
tgagagggcg agg                                                      373

<210> SEQ ID NO 5
<211> LENGTH: 560
<212> TYPE: DNA
<213> ORGANISM: Trypanosoma cruzi

<400> SEQUENCE: 5
cagaaaaaga acgtagattt ccaaccaaaa cagcaagagc ggatccaaca acgaccaaac    60
aactcattat tcgagctctc caaaatatat cgcttgcctt cgggattgaa ccctcatcta   120
cagtaaaata cgccgaaagc acgcaagaag aaaatggaaa acgttcacaa agtgaggccg   180
aggagcgtgc acggcgggag gctgaggaac gagcacggcg agaggctgag gaacgagccc   240
aacgagaggc tgaggaacga gcccaacgag aggctgagga acgagcacgg cgggaggctg   300
agaagcgtgc ccggcgagag gctaaggaac gagcatggca agaggccgaa gaacgagccc   360
aacgagaggc tgaggagcgt gcccggcgag aggctgagga gcgtgcccgg cgagaggttg   420
aggagcgtgc ccggcaagag gctgaggaac tcgcacggca agagtctgag gaacgtgcac   480
ggcaagaggc cgaagaacga gcatggcaag aggctgagga gcgtgcccaa cgagaggctg   540
aggagcgtgc tcaacgagcg                                               560

<210> SEQ ID NO 6
<211> LENGTH: 440
<212> TYPE: DNA
<213> ORGANISM: Trypanosoma cruzi
<220> FEATURE:
<223> OTHER INFORMATION: Where n is an unknown nucleic acid

<400> SEQUENCE: 6
gcctcctgca actcgagctg gcagcgtgga ggtgcngcag gaactctcaa nagangacgg    60
ctctccctcg atancnttcg gagtgacttn gactgttgcg ccntttccgt ntcactattt   120
```

-continued

```
ctattgcttt taatttgctg gagaggcgcg tgtaggaggg aaagagtagt aacatggcag      180
aatcatcaaa aacgatgttg cgttagtaga gaggagggaa acatcgagac gttgagggtt      240
gcgacggnca aaattatgta catttacctg aattaggata agacttcata tggcataaac      300
tcgtggcgtt gttggtggtt ataacaagca acggtgacga tgtcttaggc tacactgctg      360
cactcaaaga gttttacagg tacttgcggg atatttgttc ctgtgagttt gttttctatt      420
gtaatttatt nngtctcaat                                                  440
```

<210> SEQ ID NO 7
<211> LENGTH: 1915
<212> TYPE: DNA
<213> ORGANISM: Trypanosoma cruzi

<400> SEQUENCE: 7

```
cgatgcgtct gtcgtagacc tgggaggcga ggcccatggg acacactatg cctttttgcc       60
cgatgtgatc aagggggattg cgcaggaaga gctgtacctg gaagacgatg cgtacttcca     120
ggagttgctt gcgaggtata agaacttgt ccctgtgggt gccgagccaa ccgagccacg       180
cgcaaagcag ttgcgcgagc aaatgcggat acgggctggg cagcttgctg ttgacacccg      240
aaagcttcat gcgccgaag agcgggctgc atcgcggatg gcgacacttt acccgtttgt       300
gggctcggcg ccgctgggag ttgctctgtg gaatatcccc gtggaggcgg acgaagagtt      360
ctgtgcactt ctgctgaagc gcgaagaagc gctggcgggg aagtcagggt ccgtccacga      420
agtggaatct gcgctgagcg cgcgtgcgga agcgatggcg aaggcggtgc tggaggagga      480
ggaggcgctt gcggcgggcat ttccatttct ggggcggagt gttaagggag cccctctgcg     540
tgagttggct ctcatgtctg atcccaattt tgcggagctg gcgacacggc acgcgcagga     600
ggcgacctcg ggcgatgcgg cgggtatttt gcgccttgag caggagctgc gtgaccaggc     660
atgtcgcata gcacgtgagg tgcgagtggc tcggcggctt gacgccgtcg caatgaggac      720
ctgcacgagc ggtacccgtt tcttcccgag gagccggtgc gcggcattct tcttggtgct      780
gtgcgtccgg tgcagcaacc ggcgttccgc gagctttcaa acaagttgga tgagcagcgc      840
cgggacccga cacgcaacgc agccgcgatc cgcacgacgg aggagcagat gactgcgttg      900
gtggtgcgac tggctgagga gcgcgcggag gcgacggaga gggcgcatga gcagtacccg      960
tttctcccac gacgtgtgct gggcgtgcgc cttggtgaca tctcgctgca ggaggatgat     1020
gtgttgtcac agctggcgcg gcgtcgtgtg cggcagctaa gaaactccaa gacggcgatt     1080
gacgcacacg caactgaaga agagatgata aggcgcgcag aggagctggc tcgcaacgtg     1140
aagcttgtcg acgcataccg tgggaatggg aacgagtacg tgcgtgcctg caacccgttt     1200
ctcgtgtacg aggaccgcaa gtgcgtcctc ctgagtgagc tgccgcttgc cggtggcgac     1260
gtgtaccagg gcttgttccg ggattatctg actgcgctgg aggacgccga ggcaaatgca     1320
ccgcggatcg cggagctgga gaatgcgctt cggtcccgtg cggatgagtt ggcgctggag     1380
gtttgcgaga gggacgcgcg gttgttgcat tactcattcc tctcggccca ggatgttcct     1440
ggttggtctg aagcactgct gcatgacgcg gagtttcagc agctacgtga gcgttacgag     1500
gaactgagca aggatccaca ggggaacgcc gaggcattgc gtgagcttga ggatgcaatg     1560
gaggctcgga gcagagccat tgcggaagcg ttgcggactg cagagcgact aatccactga     1620
gcaggcgagg ctgaagacgc cgtcacaggc ggggtctggc gtgtccgcgg gtgatcgaat     1680
gcatggcagc gagcatgcgg atctcgcgca tgaaggggga agcacggctg gcggcaccat     1740
```

```
gagggggggca gagtctgtct ccaagagcag tgggaaacac tctcaaggtc ggtctcgcat    1800
gcgtctgtcg tagacctggg aggcgaggcc catgggacac actatgcctt tttgcccgat    1860
gtgatcaagg ggattgcgca ggaagagctg tacctggaag acgatgcgta cttcg         1915
```

<210> SEQ ID NO 8
<211> LENGTH: 400
<212> TYPE: DNA
<213> ORGANISM: Trypanosoma cruzi
<220> FEATURE:
<223> OTHER INFORMATION: Where any n is an unknown nucleic acid

<400> SEQUENCE: 8

```
ttaccaagct gagatagata aaaggctgca ggagcagctt gcccctgaga ggatgagggc      60
tctttccgca tttctttcgg agtgactttg actgttgcgc cgtttccgtg tcactatttc     120
tattgctttt aatttgctgg agaggcgcgt gtaggaggga aagagtagta acatggcaga    180
atcatcaaaa acgatgttgc gttagtagag aggagggaaa catcgagacg ttgagggttg    240
cgacggncaa aattatgtac atttacctga attaggataa gacttcatat ggcataaact    300
cgtggcgttg ttggtggtta taacaagcaa cggtgacgat gtcttaggct acactgctgc    360
actcaaagag ttttacaggt acttgcggat atttgttcct                          400
```

<210> SEQ ID NO 9
<211> LENGTH: 936
<212> TYPE: DNA
<213> ORGANISM: Trypanosoma cruzi

<400> SEQUENCE: 9

```
gcctcctgca actcgtgctg gcagcgttga agttcggcag aaatctcaac aaacgccttc     60
tgtccctcgg aaaccttccc gttaagagac acaagcagtt caatgagcga catggtcgct    120
tcggacacgt ccaatgcttt catggtttgt tccagccgcc gctgaaagtt atccacacat    180
gagaacaaca aagacaaatc taaatcggcg tcgccgtgct catacacatc aaacgccacc    240
gtctcgccca aacattcaa aaagttcacc aaaaagttta caagcttact caaattgtca    300
cgaagtgagc taacggtaat ttctaaactt ccatttcttg cgtcatccct agccttcgcc    360
gcgactacct tctccttcca tagcactagc ttctcctcca ccaaacgaat accgctctcc    420
ttttctttca cagcaacctc acattccctt tcaatttcat tcaacctaat tggattattt    480
tcttaaacga cttgccgtgc cctcctcggg ctgatgaaag gcctcgccca gctgcgcacg    540
cagattcacg gtgtccgccc cgttctgctc ccggagagcg gccagttcct cggtggttcg    600
cttcagctcg cgatgcacct cctcgcgctg ctgcaaggcc tcgtccagct gcgcacgcag    660
attcacggtg tccgccccgc tctgctcccg gagagcgggc agttcctcgg tggttcgctt    720
cagctcgcga tgcacctcct cgcgctgctg caaggcctcg tccagctgcg cacgcagatt    780
cacggtgtcc gccccgctct gctcccggag agcgggcagt tcctcggtgg ttcgcttcag    840
ctcgcgacgc acctcctcgc gctgctgaa ggcctcgccc agctgcgcac gcagattcac    900
ggtgtccgcc cctctctgct cccggagggc gggcag                              936
```

<210> SEQ ID NO 10
<211> LENGTH: 702
<212> TYPE: DNA
<213> ORGANISM: Trypanosoma cruzi
<220> FEATURE:
<223> OTHER INFORMATION: Where any n is an unknown nucleic acid

<400> SEQUENCE: 10

```
acttgaaaga ntgacccaat aatngggttc cttattgtgc caccccaaat aaacccgtaa    60
ccaatttgtg gctgggatgg atcccccac nctctttgac ncatgtcaag agtanatggg   120
acgtcaaagt cacttagaga gggattcatg ggtnccattg atcacaagag cctnctggaa   180 gaccccgtg aagataaccc aatgagattt atcgtctgca taagatcaca cgaggcggta   240
ttagcaatta tcttcacaga ttcttttcct tgtgatggtg gcttgcggta gtttgtcatc   300
attgttttct gaatgcaatg aagcacacga cttgtaatac gttctccatg tctttcaatc   360
gtttccaacg cctccacaat gtctgcagga tccccaggaa ggtcagcagt catcagaagc   420
tcttcacatg aacgccgtaa actaggatca cgctcaacaa ggctagcaat cgcatttgcc   480
attctcggat tccacttgca aaaccactcc ggaagtttat ttccacgact gacctctgtc   540
ataatgttga acctctccct aaagccttta cccgccacgg caagccacat ctcaagagct   600
atcataccca ggctgtattc atccacttta aagtcgtagt cttcccctcg ctcttgctct   660
ggggcacagt acaacacaga acccaagttt cctgtaggac cg                    702
```

```
<210> SEQ ID NO 11
<211> LENGTH: 510
<212> TYPE: DNA
<213> ORGANISM: Trypanosoma cruzi

<400> SEQUENCE: 11
cgagtattcc tgtggaaatt gatattagaa accaggactt ttcttttctt gacccggcac    60
cggagggcat tcctattcag gacatacatc ttatgggaga ttctgcattt gccgcatctg   120
cgcgtgagcg catgaaactg aaaagaaatc ctgttgcgaa tgcgagcaag atcagtgccc   180
ttgaggagga gatggatcaa cgtgctcatg tattggctaa gcaggtgcgt gacaaagagc   240
gcactttcct tgatccagag cctgagggtg ttccacttga gttgctttca ttaaatgaaa   300
atgaggcctc acaggaattg gagcgagagc ttcgtgccct aaatcgcaaa ccccggaagg   360
atgccaaagc aatagttgct cttgaagatg atgtgcgtga cgaacacacg tgcttgccaa   420
ggagctaaag gaaaatgagc ggaacatctt tgttggctcc acagcctgag ggtgtgccgg   480
tgtctgagct gtcgttggat ttagacgagc                                    510
```

```
<210> SEQ ID NO 12
<211> LENGTH: 320
<212> TYPE: DNA
<213> ORGANISM: Trypanosoma cruzi
<220> FEATURE:
<223> OTHER INFORMATION: Where any n is an unknown nucleic acid

<400> SEQUENCE: 12
cggtcgtggc agagccaaag ccaccaacag caggtgccga cgtgtgcgcg gcagagccga    60
agccaccagc agcaggcgcc gaagtggtcg tggcagagcc aaagccacca gcagcaggtg   120
ccgacgtgtg cgcggcagag tcgaagccac caacagcagg tgccgacgtg gtcgtggcag   180
agccaaagtc accagtagta gggnccgacg tgtgngtggc agagncanag ncaccagtag   240
naggtgncga cgtngtcgtg gnagagncga ngtcaccagc aggaggtgnc gacgtntgng   300
nggnagaggc gatgtcacca                                               320
```

```
<210> SEQ ID NO 13
<211> LENGTH: 302
<212> TYPE: DNA
<213> ORGANISM: Trypanosoma cruzi
```

<400> SEQUENCE: 13

```
atgcatctcc cccgtacatt attttgcgga aaattggatt tttacgggga ggtggggttc        60
gattggggtt ggtgtaatat aggtggagat ggagtgcagt gggataggat tagaatgtag       120
ttggtgtagt acagagttta tatagtatag tgttgatgtt attatacaat gaggtaagag       180
aatggagtga gaaagagtat gtttgttagt ttggttgtta atgttatgta ttcatgttat       240
cagtatatgt tgtatgtgta tggtgatagc ggtgggtgta gctgtatgtg gtaggttaga       300
gt                                                                     302
```

<210> SEQ ID NO 14
<211> LENGTH: 298
<212> TYPE: DNA
<213> ORGANISM: Trypanosoma cruzi

<400> SEQUENCE: 14

```
cagtttcaat ttcctctcca cctgatcccg ctgttgcaaa agcgtccttg atgtatcctg        60
ctccttttgcc gctagcgcct cccttgctaa gcgcagttcc tcttgcagcc tcgcctgcac      120
ccgttccgcc tccattaatc tcttctcccc gattgcttct ttggcgcgta atcctccag       180
ttccttctct atcaaagtgt gcctcccatt cctgatccgc gactcttcac aggcttcttg      240
ctccgcgtca cggagacgcc tcttgagagc ctcgttcttc tcttccaggt cttctggg       298
```

<210> SEQ ID NO 15
<211> LENGTH: 2144
<212> TYPE: DNA
<213> ORGANISM: Trypanosoma cruzi

<400> SEQUENCE: 15

```
cgcggaattc ttaccaagct gagatagata aaggctgca ggagcagctt gcccctgaga         60
ggatgaaggc tctttccaca tttctttggg agtgaccttg actgttgcgc cgtttccgtg       120
tcactatttc tattgctttt aaattgctgg agaggcgcgt gtaggagaga aagagtagta       180
acatggcgga atcatcaaaa acgatgttgc gtaagtagag aggagggaaa catcgagacg       240
ttgagggttg cgacggccaa gattatgtac atttacctga attaggataa gacttcatat       300
ggtataaagt cgtggcgttg ttggtggtta taacaagcaa cggtgacgat gtctcagtct       360
acactgctac aatcaaagag ttttacaggt acttgtggat atttgttcct gtgagtttgt       420
tttctattat aatttatttt gtctcaattt tttgtttccc cgcttcctac ggtctctttt       480
tttcttcgtt cttgaaattt caattattgc ttaaccacaa gcatccagta cttcaacctc       540
cccatcaaat ggtgtcgctg aagctgcagg ctcgtttggc ggcggacatt ctccgctgcg       600
gtcgccaccg tgtgtggctg gaccctaatg aggcctctga gatttccaat gcaaactcgc       660
gcaagagcgt gcgcaagttg atcaaggatg gtctgattat tcgcaagcct gtcaaggtgc       720
actcgcgctc ccgctggcgc cacatgaagg aggcgaagag catgggccgc cacgagggcg       780
ctgggcgccg cgagggtacc cgcgaagccc gcatgccgag caaggagctg tggatgcgcc       840
gtctgcgcat tctccgccgc ctgctgcgca agtaccgcga ggagaagaag attgaccgcc       900
acatttaccg cgagctgtac gtgaaggcga agggaacgt gtttcgcaac aagcgtaacc       960
tcatggagca catccacaag gtgaagaacg agaagaagaa ggaaaggcag ctggctgagc      1020
agctcgcggc gaagcgcctg aaggatgagc agcaccgtca aaggcccgc aagcaggagc      1080
tgcgtaagcg cgagaaggac cgcgagcgtg cgcgtcgcga agatgctgcc gctgccgccg      1140
ccgcgaagca gaaagctgct gcgaagaagg ccgctgctcc ctctggcaag aagtccgcga      1200
```

```
aggctgctgc acccgcgaag gctgctgctg cacccgcgaa ggccgctgct ccacccgcga    1260
agaccgctgc tgcacccgcg aaggctgctg cacctgccaa ggctgctgct ccacccgcga    1320
aggctgctgc tccacccgcg aagaccgctg ctccacccgc gaagaccgct gctccacccg    1380
cgaaggctgc tgctccaccc gcgaaggccg ctgctccacc cgcgaaggcc gctgctccac    1440
ccgcgaaggc cgctgctgca cccgcgaagg ccgctgctgc acccgcgaag gctgctgctc    1500
cacccgcgaa ggccgctgct ccacccgcga aggctgctgc tccacccgcg aaggctgctg    1560
ctccacccgc gaaggctgct gctgctcccg ttggaaagaa ggctggtggc aagaagtgaa    1620
gcgcgcacta gtacgaccaa cttgtttttt ttttggtat ttaatatttt ctgaggaaga    1680
agtgggtatt gagggtcttt ctttccgcgt ttgtgttggt ttgtggtgtt cgtgacatta    1740
tagtagatcc aaagtattct tcagtgtccc ttttcctttt ctccatcctt tttcctattt    1800
tttgtttgtc ttctctacga tctttgttgt cgtgtgacct ccgctgtatg gaactgacgg    1860
ccggcgttgt gagagacgat gtcgcacgtc acggcggacc tggagtattt taaatgtgac    1920
atgtgcgggg tgtatctgca caaagacatc ttttgcgacc atcgacgtga gtgtaaaggc    1980
cttgattcga aagagctgaa gaagagccag tgtcgtcaga tcgggatggc attagacaag    2040
gaggcacggc accgaattgc gtcacgaatg gctgatggag caactctcgt gcctgtcgag    2100
cttgcagaac gacatcaaca ggcgcgtgtg cggcgtaatg tggc                      2144
```

<210> SEQ ID NO 16
<211> LENGTH: 456
<212> TYPE: DNA
<213> ORGANISM: Trypanosoma cruzi

<400> SEQUENCE: 16

```
tgtgctgcag aaggagaggg atgaagccgt ggcggagaat gcccagctgc agaaggagag     60
ggatgacgcc gtggcggaga atgcccagct gcagaaggag agggatgacg ccgtggcgga    120
gaatgcccag ctgcagaagg agagggatga cgccgtggcg gagaatgccc agctgcagaa    180
ggagagggat gacgccgtgg cggagaatgc ccagctgcag aaggagaggg acgaagccgt    240
ggcggagaat gcccagctgc agaggggagag ggatgacgcc gtggcggagg atgcccagct    300
gcagaaggag agggatgaag ccgtggcgga gaatgcccag ctgcagaggg gagagggatga    360 agccgtggcg gagaatgccc agctgcagaa ggagagggat gacgtcgtgg cggagaatgc    420
ccagctgcag aaggagaggg atgacgccgt ggcgga                               456
```

<210> SEQ ID NO 17
<211> LENGTH: 2446
<212> TYPE: DNA
<213> ORGANISM: Trypanosoma cruzi
<220> FEATURE:
<223> OTHER INFORMATION: Where any n is an unknown nucleic acid

<400> SEQUENCE: 17

```
tgaaggccgt tgatcctttt cagggaacga caccgccgcc ctataaatgg caagaaatga     60
ctggatctga ggcggcagcc ggctcgcttt gtgtacccag ccttgctgag gtggccggcg    120 gtgtgttttgc cgttgctgaa gctcagcgca gtgaaaggga cgaagcctgc ggccatgctg    180
cgattgcaac aacgcacatt gagacgggcg gtggtggctc aaaggcgatc tcggcgatgg    240
atgcaggcgt ttttctcgta gaacttgtgg atgccgccag tggtacgatc aggacacgag    300
aaaagatgca gccaacgaca attgtgagcg gcgacactat ctacatggcc cttggggact    360
```

```
acgagaagaa gacgtctggg ggtcgggctg ccgatgcaga tggctggagg cttttactga      420 tgagggaac tctcactgag gatggtgggc agaagaaaat catgtggggt gatatccgtg       480
cagtggaccc tgtggccatc gggcttactc aattcctgaa gagggtgatc ggtggcggag      540
gatcgggtgt tgtgacgaag aacggttacc ttgtgcttcc catgcaggca gtagaaaagg     600
atggaaggag tgttgtactg tccatgcgtt caacatgcg tatagaagca tgcgagctct      660
cgtccggtac gacaggtagt aactgcaagg aaccatccat cgcgaatttg aaggaaatc      720 taattttaat tacttcttgc gctgccggct actacgaagt attcaggtcc cttgactctg     780
ggacaagttg ggaaatgagt ggtaggccaa ttagtcgcgt gtggggcaac tcgtatggtc     840 gaaagggta tggcgttcgc tgtggcctca ccaccgtaac cattgaggga agggaagtgc      900
tgcttgttac cacgccagtg tatttggagg agaaaaatgg tagggtcgg cttcatcttt      960 gggtgacgga cggtgcacgt gtgcatgatg ctgggccgat atccgatgca gctgatgacg    1020
ctgctgccag ttccctgttg tatagcagtg ggggcaatct gatttcgctg tacgagaata    1080
agagtgaggg gtcatacggt cttgttgctg tgcacgtgac tacgcagctg agcggataa      1140 agactgtgtt gaagaggtgg caggagttgg atgaagccct aagaacgtgc agatccactg    1200
ccactatcga cccggtgaga aggggcatgt gtattcgtcc cattcttact gacgggcttg    1260
ttggctattt gtctggtctg tcgactggga gtgagtggat ggacgagtac ctctgcgtga    1320
acgcaactgt tcatgggacg gtgagagggt tctccaatgg agtgacgttt gaaggacccg    1380 gagcagggc ggggtggcct gttgcccgaa gtggacagaa tcaaccgtac catttcttac      1440
acaaaacgtt cactctagtg gtgatggcgg tcatccacga taggccgaag aaacgcaccc    1500
ccattccttt gattcgtgtg gtgatggatg acaatgacaa gactgtgcta tttggtgtgt    1560
tttacaccca tgatgggagg tggatgactg taattcatag tggcggtaga caaatacttt    1620
caacagggtg ggacccagaa aaaccgtgtc aggtagtgct cgcacacgac acgggccatt    1680
gggatttcta cgttaacgcg aggaaggctt actttggcac ctacaagggt ctcttctcca    1740
aacaaacagt atttcacaca tccaattcca cggggagagt ggggaagttg cagagtccag    1800
ccatttgtca ctcttcaacg cccgtttgta taaccgaaga ctcaattcca agcatctaag    1860
atggctcatg tcggcgaga caggcccaaa atacgatgat ggcagctctt attctgcgag    1920
tgcgtccgag gaaggaagca gaggtggcag ctccatgccc gcgggtacgt ccgaggaagg    1980
aagcagaggt ggcagctcca tgcctgcggg tacgtccgag gaaggaagca gaggaggcag    2040
ctccatgcct gcgggtacgt ccgaggaagg aagcagagga ggcagctcca tgcctgcggg    2100
tacgtccgag gaaggaagca gaggtggcag ctccatgcct gcgggcactt ccgaagaagg    2160
aagcagaagt ggcanctcca tgccttcggg ctcttccgaa gaaggaagca gaagaggccg    2220
ctccctgcct tcgggttctt ccgaaggaag gaagcagagg aggccctccc tgcctgcggg    2280
ttcttccgaa gaaggaaaca gaagtggcnc tccatgcccg cgggttcttc cgaggaagga    2340
accagaagaa gcnctccctg cccgcnggtt cntccnaaga agaaacana agttggccnc    2400 tcccngcccc nngtttcttc cnaangaaag aaacaaaagt ggcccc                  2446
```

<210> SEQ ID NO 18
<211> LENGTH: 345
<212> TYPE: DNA
<213> ORGANISM: Trypanosoma cruzi

<400> SEQUENCE: 18

```
gggtacgtcc gaggaaggaa gcagaggtgg cagctccatg cctgcgggta cgtccgagga     60
```

```
aggaagcaga ggtgtcagct ccatgcctgc gggtacgtcc aggaaggaa  acagaggagg    120 caactccatg cctgcgggta cgtccgagga aggaagcaga ggtggcagct ccatgccttc    180
gggcacgtcc gaggaaggaa gcagaggtgg cagctccatg ccttcgggta cgtccgagga    240
aggaagcaga ggaggcagct ccatgcctgc gggtacgtcc gaggaaggaa gcagaggtgg    300
cagctccatg cccgcgggta cgtccgagga aggaagcaga ggccg                   345

<210> SEQ ID NO 19
<211> LENGTH: 835
<212> TYPE: DNA
<213> ORGANISM: Trypanosoma cruzi

<400> SEQUENCE: 19
ggcacgagct gtactatatt gtaggagagc agccatgggt atcgttcgca gccgcctgca     60
taaacgcaag atcaccggtg aaagacgaa  gatccaccgg aagcgcatga aggccgaact    120
cggccgtctt cccgcgcaca cgaagcttgg cgcccgccgc gtgagtcccg tccgcgcccg    180
cggtgggaac ttcaagctcc gcggtcttcg cctggacacc ggcaattttg cgtggagcac    240
agaagccatt gctcagcggg cccgtatcct cgacgttgtg tacaacgcca cttctaacga    300
gctggtgcgc acgaagacgc ttgtgaagaa ctgcattgtt gtggtggacg ccgcgccctt    360
caagttatgg tacgcgaagc actacggtat cgaccttgag ccgcgaagag caagaagacg    420
ctgcagagca cgacggagaa gaagaagtcg aagaagacct cacacgccat gactgagaag    480
tacgacgtca agaaggcctc cgacgagctg aagcgcaagt ggatgctccg ccgcgagaac    540
cacaagattg agaaggcagt tgctgatcag ctcaaggagg gccgtctgct cggccgcatc    600
acgagccgcc ctggccagac agcccgcgcc gatggtgcac tgctggaggg cgccgaactg    660
cagttctatc tgaagaagct cgagaagaag aagcggtaga aaggatgtt  cgggagacgg    720 gaggaggcgc caccaccacc actcatggtg atgcaccac  tacctacttt gttttcattt    780
tttgttttac ctctaatttt ttaggccaga ggggggggaaa aaaaaaaaa  aaaaa         835

<210> SEQ ID NO 20
<211> LENGTH: 555
<212> TYPE: DNA
<213> ORGANISM: Trypanosoma cruzi

<400> SEQUENCE: 20
ggcacgagaa aaagaaaac  aaacaaataa aatcaaaaac agtaaatcca tcacttcaac     60
aatgagcatt gagagcgcct tttacgcctt tgcctccttt ggtggtgcgc ccacgaaaga    120
gatggacaat gctcacttct ccaagatgct gaaggagacg aaggtcattg gaaagcaatt    180
caccagcacc gacgccgatc ttctcttcaa caaagtgaag gcaaagggag cccgcaaaat    240
tacattgtcg gattttgttg acaaggctgt tcctgagatt gcatcaaagt taagaagtc     300 cgcggaggaa ttgatcgcag atatttcaag ttgctctccc gaggcacgcg caaccaaggc    360
cgatgcagtt aagttccacg acgataagaa catgtacact ggtgtctaca aggccggcgg    420
gccaacaaac gtggatcgca actccggctc cctttcaggt gtcgtggatc gccgtgtggc    480
gcagactgac gttcgtggca cgactgcttc ccagaagtaa agagggaaac gaaatggaaa    540
aaaaaaaaaa aaaaa                                                    555

<210> SEQ ID NO 21
<211> LENGTH: 936
<212> TYPE: DNA
```

<213> ORGANISM: Trypanosoma cruzi

<400> SEQUENCE: 21

```
ggcacgagag ctctcttcgt cagtcatgac gctcgggaag aacaagcgca tcagcaaggg      60
cggcaagcgc ggcaagaaga agacccagga gacgatgagc cgcaaggagt ggtacgatgt     120
ggttgccccc aagaactttg aggtgcgcca gtttggcaag accatctgca acaagaccca     180
gggcacaaag atcgcggcgg actacctgcg cgggcgcgtg tacgaaagca accttgcgga     240
tctgaacaag acgcaaggcg acgacgacgc ctaccgcaag gtgaagtttg ttgtgcagga     300
ggtgcagggc cgcaacctgc ttacgcagtt ccacagcatg gaaatgacat ctgaccgcgt     360
gtacttttg  ctgcgcaagt ggtgcacgac gatcgaggcg gcagtggaga cgaagactgc     420
ggacggctac accctgcgcc tcttcgtgat tgccttcacg aagaagcaga gcaaccagct     480
gtcgaagaac tgctatgcca agacgcgcct ggtgaagtgg gtgcgccatc gcatcacgaa     540
cctcatccgc cagcgcctgt cgaaggtgaa catcaacgag gcggtgacgc tgctgacacg     600
caacatcctg cgcgatcgtc tggcaaagcg ctgcaacccc atcgtgccgc tgcgcgatct     660
ccgcatccgc aaggtgaagg tggtccgcac ccccggtt  tgacgcccag gcgcttctga     720
atgcacacgg cgagatcccc gcctcggctg agggtgaggc acgcgtcgtc gaggaagccc     780
aagaggctcc cgccgctgaa gccacagcct aagccttcca tgtggaggaa ggatgtgtga     840
tgtgaaagct ctttgttctt ttttctttct attttgaaac ggtgattccg catatatata     900
ttaaaaaaaa aaaaaaaaaa aaaaaaaaaa aaaaaa                              936
```

<210> SEQ ID NO 22
<211> LENGTH: 581
<212> TYPE: DNA
<213> ORGANISM: Trypanosoma cruzi

<400> SEQUENCE: 22

```
gtactatatt gttgctatta acacactgtt aggaacgcga aaccatgcag atcttcgtga      60
agacactgac gggcaagacg atcgcgctcg aggtggaatc cagcgacacc attgagaacg     120
tgaaggcgaa gatccaggac aaggagggca ttccgccgga ccagcagcgc ctgatcttcg     180
ctggcaagca gctggaggac ggccgcacgc tcgcagacta caacatccag aaggagtcca     240
cgctgcacct tgtgctgcgc ctgcgcggtg tgtgatgga  gccgacactt gaggccctgg     300
cgaagaagta caactgggag aagaaggtat gccgccgctg ctacgcccgt ctgccggtgc     360
gtgcgtccaa ctgccgcaag aaggcatgtg gccactgctc caacctccgc atgaagaaga     420
agctgcggta gtctgcgatg ctgtggaccg acgcattgaa atacacaccg tcttcggcgt     480
tcctttttt  tatatgtctt ttttttatt  gagaagatgt cttgtttgtt gttgttttt      540
tttcaaaaaa aaaaaaaaa  aaaaaaaaa  aaaaaaaaa  a                         581
```

<210> SEQ ID NO 23
<211> LENGTH: 30
<212> TYPE: PRT
<213> ORGANISM: Trypanosoma cruzi

<400> SEQUENCE: 23

```
Leu Pro Pro Leu Leu Pro Ser Ser Asp Val Pro Glu Gly Met Glu Leu
  1               5                  10                  15
Pro Pro Leu Leu Pro Ser Ser Asp Ile Pro Glu Gly Met Glu
                 20                  25                  30
```

```
<210> SEQ ID NO 24
<211> LENGTH: 90
<212> TYPE: PRT
<213> ORGANISM: Trypanosoma cruzi

<400> SEQUENCE: 24

Gly Cys Leu Leu Cys Phe Leu Pro Arg Thr Cys Pro Lys Ala Trp Ser
 1               5                  10                  15

Cys Leu Leu Cys Phe Leu Pro Arg Thr Tyr Pro Lys Ala Trp Ser Cys
                20                  25                  30

His Leu Cys Phe Leu Pro Arg Thr Tyr Pro Arg Ala Trp Ser Cys His
            35                  40                  45

Leu Cys Phe Leu Pro Arg Thr Cys Pro Lys Ala Trp Ser Cys His Leu
        50                  55                  60

Cys Phe Leu Pro Arg Thr Tyr Pro Arg Ala Trp Ser Cys His Leu Cys
 65                  70                  75                  80

Phe Leu Pro Arg Thr Tyr Pro Arg Val Trp
                85                  90

<210> SEQ ID NO 25
<211> LENGTH: 90
<212> TYPE: PRT
<213> ORGANISM: Trypanosoma cruzi

<400> SEQUENCE: 25

Ala Ala Ser Ser Ala Ser Phe Leu Gly Arg Ala Arg Arg His Gly Ala
 1               5                  10                  15

Ala Ser Ser Ala Ser Phe Leu Gly His Thr Arg Arg His Gly Ala Ala
                20                  25                  30

Thr Ser Ala Ser Phe Leu Gly Arg Thr Arg Gly His Gly Ala Ala Thr
            35                  40                  45

Ser Ala Ser Phe Leu Gly Arg Ala Arg Arg His Gly Ala Ala Thr Ser
        50                  55                  60

Ala Ser Phe Leu Gly Arg Thr Arg Gly His Gly Ala Ala Thr Ser Ala
 65                  70                  75                  80

Ser Phe Leu Gly Arg Thr Arg Gly His Gly
                85                  90

<210> SEQ ID NO 26
<211> LENGTH: 40
<212> TYPE: PRT
<213> ORGANISM: Trypanosoma cruzi

<400> SEQUENCE: 26

Ser Val Pro Gly Lys Arg Leu Arg Asn Ser His Gly Lys Ser Leu Arg
 1               5                  10                  15

Asn Val His Gly Lys Arg Pro Lys Asn Glu His Gly Lys Arg Leu Arg
                20                  25                  30

Ser Val Pro Asn Glu Arg Leu Arg
            35                  40

<210> SEQ ID NO 27
<211> LENGTH: 40
<212> TYPE: PRT
<213> ORGANISM: Trypanosoma cruzi

<400> SEQUENCE: 27

Glu Ala Glu Glu Leu Ala Arg Gln Glu Ser Gly Glu Arg Ala Arg Gln
 1               5                  10                  15
```

```
Glu Ala Glu Glu Arg Ala Trp Gln Ala Glu Glu Arg Ala Gln Arg
            20                  25                  30

Glu Ala Glu Glu Arg Ala Gln Arg
            35                  40
```

<210> SEQ ID NO 28
<211> LENGTH: 56
<212> TYPE: PRT
<213> ORGANISM: Trypanosoma cruzi

<400> SEQUENCE: 28

```
Ser Trp Gln Ser Gln Ser His Gln Gln Gln Val Pro Thr Cys Ala Arg
 1               5                  10                  15

Gln Ser Arg Ser His Gln Gln Ala Pro Lys Trp Ser Trp Gln Ser
            20                  25                  30

Gln Ser His Gln Gln Val Pro Thr Cys Ala Arg Gln Ser Arg Ser
            35                  40                  45

His Gln Gln Gln Val Pro Thr Trp
        50                  55
```

<210> SEQ ID NO 29
<211> LENGTH: 56
<212> TYPE: PRT
<213> ORGANISM: Trypanosoma cruzi

<400> SEQUENCE: 29

```
Gly Arg Gly Arg Ala Lys Ala Thr Asn Ser Arg Cys Arg Arg Val Arg
 1               5                  10                  15

Gly Arg Ala Glu Ala Thr Ser Ser Arg Arg Ser Gly Arg Gly Arg
            20                  25                  30

Ala Lys Ala Thr Ser Ser Arg Cys Arg Pro Val Arg Gly Arg Ala Glu
            35                  40                  45

Ala Thr Asn Ser Arg Cys Arg Arg
        50                  55
```

<210> SEQ ID NO 30
<211> LENGTH: 56
<212> TYPE: PRT
<213> ORGANISM: Trypanosoma cruzi

<400> SEQUENCE: 30

```
Val Val Ala Glu Pro Lys Pro Pro Thr Ala Gly Ala Asp Val Cys Ala
 1               5                  10                  15

Ala Glu Pro Lys Pro Pro Ala Ala Gly Ala Glu Val Val Val Ala Glu
            20                  25                  30

Pro Lys Pro Pro Ala Ala Gly Ala Asp Val Cys Ala Ala Glu Pro Lys
            35                  40                  45

Pro Pro Thr Ala Gly Ala Asp Val
        50                  55
```

<210> SEQ ID NO 31
<211> LENGTH: 7
<212> TYPE: PRT
<213> ORGANISM: Trypanosoma cruzi

<400> SEQUENCE: 31

```
Pro Pro Ala Lys Ala Ala Ala
 1               5
```

<210> SEQ ID NO 32

```
<211> LENGTH: 151
<212> TYPE: PRT
<213> ORGANISM: Trypanosoma cruzi

<400> SEQUENCE: 32

Val Leu Gln Lys Glu Arg Asp Glu Ala Val Ala Glu Asn Ala Gln Leu
 1               5                  10                  15

Gln Lys Glu Arg Asp Asp Ala Val Ala Glu Asn Ala Gln Leu Gln Lys
            20                  25                  30

Glu Arg Asp Asp Ala Val Ala Glu Asn Ala Gln Leu Gln Lys Glu Arg
        35                  40                  45

Asp Asp Ala Val Ala Glu Asn Ala Gln Leu Gln Lys Glu Arg Asp Asp
    50                  55                  60

Ala Val Ala Glu Asn Ala Gln Leu Gln Lys Glu Arg Asp Glu Ala Val
65                  70                  75                  80

Ala Glu Asn Ala Gln Leu Gln Arg Glu Arg Asp Asp Ala Val Ala Glu
                85                  90                  95

Asp Ala Gln Leu Gln Lys Glu Arg Asp Glu Ala Val Ala Glu Asn Ala
            100                 105                 110

Gln Leu Gln Arg Glu Arg Asp Glu Ala Val Ala Glu Asn Ala Gln Leu
        115                 120                 125

Gln Lys Glu Arg Asp Asp Val Val Ala Glu Asn Ala Gln Leu Gln Lys
    130                 135                 140

Glu Arg Asp Asp Ala Val Ala
145                 150

<210> SEQ ID NO 33
<211> LENGTH: 140
<212> TYPE: PRT
<213> ORGANISM: Trypanosoma cruzi

<400> SEQUENCE: 33

Cys Arg Arg Arg Gly Met Lys Pro Trp Arg Met Pro Ser Cys Arg
 1               5                  10                  15

Arg Arg Gly Met Thr Pro Trp Arg Met Pro Ser Cys Arg Arg Arg
            20                  25                  30

Gly Met Thr Pro Trp Arg Arg Met Pro Ser Cys Arg Arg Arg Gly Met
        35                  40                  45

Thr Pro Trp Arg Arg Met Pro Ser Cys Arg Arg Gly Met Thr Pro
    50                  55                  60

Trp Arg Arg Met Pro Ser Cys Arg Arg Arg Gly Thr Lys Pro Trp Arg
65                  70                  75                  80

Arg Met Pro Ser Cys Arg Gly Arg Gly Met Thr Pro Trp Arg Arg Met
                85                  90                  95

Pro Ser Cys Arg Arg Arg Gly Met Lys Pro Trp Arg Arg Met Pro Ser
            100                 105                 110

Cys Arg Gly Arg Gly Met Lys Pro Trp Arg Arg Met Pro Ser Cys Arg
        115                 120                 125

Arg Arg Gly Met Thr Ser Trp Arg Arg Met Pro Ser
    130                 135                 140

<210> SEQ ID NO 34
<211> LENGTH: 60
<212> TYPE: PRT
<213> ORGANISM: Trypanosoma cruzi

<400> SEQUENCE: 34
```

-continued

```
Gly Tyr Val Arg Gly Arg Lys Gln Arg Trp Gln Leu His Ala Phe Gly
 1               5                  10                  15

Tyr Val Arg Gly Arg Lys Gln Arg Trp Gln Leu His Ala Phe Gly Tyr
                20                  25                  30

Val Arg Gly Arg Lys Gln Arg Gln Leu His Ala Cys Gly Tyr Val
            35                  40                  45

Arg Gly Arg Lys Gln Arg Trp Gln Leu His Ala Cys
        50                  55                  60

<210> SEQ ID NO 35
<211> LENGTH: 60
<212> TYPE: PRT
<213> ORGANISM: Trypanosoma cruzi

<400> SEQUENCE: 35

Gly Thr Ser Glu Glu Gly Ser Arg Gly Gly Ser Ser Met Pro Ser Gly
 1               5                  10                  15

Thr Ser Glu Glu Gly Ser Arg Gly Gly Ser Ser Met Pro Ser Gly Thr
                20                  25                  30

Ser Glu Glu Gly Ser Arg Gly Gly Ser Ser Met Pro Ala Gly Thr Ser
            35                  40                  45

Glu Glu Gly Ser Arg Gly Gly Ser Ser Met Pro Ala
        50                  55                  60

<210> SEQ ID NO 36
<211> LENGTH: 60
<212> TYPE: PRT
<213> ORGANISM: Trypanosoma cruzi

<400> SEQUENCE: 36

Val Arg Pro Arg Lys Glu Ala Glu Val Ala Ala Pro Cys Leu Arg Val
 1               5                  10                  15

Arg Pro Arg Lys Glu Ala Glu Val Ala Ala Pro Cys Leu Arg Val Arg
                20                  25                  30

Pro Arg Lys Glu Ala Glu Val Ala Ala Pro Cys Leu Arg Val Arg Pro
            35                  40                  45

Arg Lys Glu Ala Glu Val Ala Ala Pro Cys Leu Arg
        50                  55                  60

<210> SEQ ID NO 37
<211> LENGTH: 639
<212> TYPE: PRT
<213> ORGANISM: Trypanosoma cruzi
<220> FEATURE:
<223> OTHER INFORMATION: Where any Xaa is an independently selected
      amino acid

<400> SEQUENCE: 37

Asp Ala Ser Val Val Asp Leu Gly Gly Glu Ala His Gly Thr His Tyr
 1               5                  10                  15

Ala Phe Leu Pro Asp Val Ile Lys Gly Ile Ala Gln Glu Glu Leu Tyr
                20                  25                  30

Leu Glu Asp Asp Ala Tyr Phe Gln Glu Leu Leu Ala Arg Tyr Lys Glu
            35                  40                  45

Leu Val Pro Val Gly Ala Glu Pro Thr Glu Pro Arg Ala Lys Gln Leu
        50                  55                  60

Arg Glu Gln Met Arg Ile Arg Ala Gly Gln Leu Ala Val Asp Thr Arg
 65                  70                  75                  80

Lys Leu His Ala Ala Glu Glu Arg Ala Ala Ser Arg Met Ala Thr Leu
```

```
                    85                  90                  95
Tyr Pro Phe Val Gly Ser Ala Pro Leu Gly Val Ala Leu Trp Asn Ile
            100                 105                 110

Pro Val Glu Ala Asp Glu Glu Phe Cys Ala Leu Leu Leu Lys Arg Glu
            115                 120                 125

Glu Ala Leu Ala Gly Lys Ser Gly Ser Val His Glu Val Glu Ser Ala
            130                 135                 140

Leu Ser Ala Arg Ala Glu Ala Met Ala Lys Ala Val Leu Glu Glu Glu
145                 150                 155                 160

Glu Ala Leu Ala Ala Ala Phe Pro Phe Leu Gly Arg Ser Val Lys Gly
                165                 170                 175

Ala Pro Leu Arg Glu Leu Ala Leu Met Ser Asp Pro Asn Phe Ala Glu
            180                 185                 190

Leu Ala Thr Arg His Ala Gln Glu Ala Thr Ser Gly Asp Ala Ala Gly
            195                 200                 205

Ile Leu Arg Leu Glu Gln Glu Leu Arg Asp Gln Ala Cys Arg Ile Ala
            210                 215                 220

Arg Glu Val Arg Val Ala Arg Arg Leu Asp Ala Xaa Arg Asn Glu Asp
225                 230                 235                 240

Leu His Glu Arg Tyr Pro Phe Leu Pro Glu Glu Pro Val Arg Gly Ile
                245                 250                 255

Leu Leu Gly Ala Val Arg Pro Val Gln Gln Pro Ala Phe Arg Glu Leu
            260                 265                 270

Ser Asn Lys Leu Asp Glu Gln Arg Arg Asp Pro Thr Arg Asn Ala Ala
            275                 280                 285

Ala Ile Arg Thr Thr Glu Glu Gln Met Thr Ala Leu Val Val Arg Leu
            290                 295                 300

Ala Glu Glu Arg Ala Glu Ala Thr Glu Arg Ala His Glu Gln Tyr Pro
305                 310                 315                 320

Phe Leu Pro Arg Arg Val Leu Gly Val Arg Leu Gly Asp Ile Ser Leu
                325                 330                 335

Gln Glu Asp Asp Val Leu Ser Gln Leu Ala Arg Arg Val Arg Gln
            340                 345                 350

Leu Arg Asn Ser Lys Thr Ala Ile Asp Ala His Ala Thr Glu Glu Glu
            355                 360                 365

Met Ile Arg Arg Ala Glu Glu Leu Ala Arg Asn Val Lys Leu Val Asp
            370                 375                 380

Ala Tyr Arg Gly Asn Gly Asn Glu Tyr Val Arg Ala Cys Asn Pro Phe
385                 390                 395                 400

Leu Val Tyr Glu Asp Arg Lys Cys Val Leu Leu Ser Glu Leu Pro Leu
                405                 410                 415

Ala Gly Gly Asp Val Tyr Gln Gly Leu Phe Arg Asp Tyr Leu Thr Ala
            420                 425                 430

Leu Glu Asp Ala Glu Ala Asn Ala Pro Arg Ile Ala Glu Leu Glu Asn
            435                 440                 445

Ala Leu Arg Ser Arg Ala Asp Glu Leu Ala Leu Glu Val Cys Glu Arg
            450                 455                 460

Asp Ala Arg Leu Leu His Tyr Ser Phe Leu Ser Ala Gln Asp Val Pro
465                 470                 475                 480

Gly Trp Ser Glu Ala Leu Leu His Asp Ala Glu Phe Gln Gln Leu Arg
                485                 490                 495

Glu Arg Tyr Glu Glu Leu Ser Lys Asp Pro Gln Gly Asn Ala Glu Ala
            500                 505                 510
```

```
Leu Arg Glu Leu Glu Asp Ala Met Glu Ala Arg Ser Arg Ala Ile Ala
            515                 520                 525

Glu Ala Leu Arg Thr Ala Glu Xaa Thr Asn Xaa Thr Glu Gln Ala Arg
        530                 535                 540

Leu Lys Thr Pro Ser Gln Ala Gly Ser Gly Val Ser Ala Gly Asp Arg
545                 550                 555                 560

Met His Gly Ser Glu His Ala Asp Leu Ala His Glu Gly Ser Thr
                565                 570                 575

Ala Gly Gly Thr Met Arg Gly Ala Glu Ser Val Ser Lys Ser Ser Gly
            580                 585                 590

Lys His Ser Xaa Arg Ser Val Ser His Ala Ser Val Val Asp Leu Gly
            595                 600                 605

Gly Glu Ala His Gly Thr His Tyr Ala Phe Leu Pro Asp Val Ile Lys
            610                 615                 620

Gly Ile Ala Gln Glu Glu Leu Tyr Leu Glu Asp Asp Ala Tyr Phe
625                 630                 635

<210> SEQ ID NO 38
<211> LENGTH: 231
<212> TYPE: PRT
<213> ORGANISM: Trypanosoma cruzi

<400> SEQUENCE: 38

Ala Arg Ala Val Leu Tyr Cys Arg Arg Ala Ala Met Gly Ile Val Arg
1               5                   10                  15

Ser Arg Leu His Lys Arg Lys Ile Thr Gly Gly Lys Thr Lys Ile His
                20                  25                  30

Arg Lys Arg Met Lys Ala Glu Leu Gly Arg Leu Pro Ala His Thr Lys
            35                  40                  45

Leu Gly Ala Arg Arg Val Ser Pro Val Arg Ala Arg Gly Gly Asn Phe
    50                  55                  60

Lys Leu Arg Gly Leu Arg Leu Asp Thr Gly Asn Phe Ala Trp Ser Thr
65                  70                  75                  80

Glu Ala Ile Ala Gln Arg Ala Arg Ile Leu Asp Val Val Tyr Asn Ala
                85                  90                  95

Thr Ser Asn Glu Leu Val Arg Thr Lys Thr Leu Val Lys Asn Cys Ile
            100                 105                 110

Val Val Val Asp Ala Ala Pro Phe Lys Leu Trp Tyr Ala Lys His Tyr
        115                 120                 125

Gly Ile Asp Leu Asp Ala Ala Lys Ser Lys Lys Thr Leu Gln Ser Thr
    130                 135                 140

Thr Glu Lys Lys Lys Ser Lys Lys Thr Ser His Ala Met Thr Glu Lys
145                 150                 155                 160

Tyr Asp Val Lys Lys Ala Ser Asp Glu Leu Lys Arg Lys Trp Met Leu
                165                 170                 175

Arg Arg Glu Asn His Lys Ile Glu Lys Ala Val Ala Asp Gln Leu Lys
            180                 185                 190

Glu Gly Arg Leu Leu Ala Arg Ile Thr Ser Arg Pro Gly Thr Ala Arg
        195                 200                 205

Ala Asp Gly Ala Leu Leu Glu Gly Ala Glu Leu Gln Phe Tyr Leu Lys
    210                 215                 220

Lys Leu Glu Lys Lys Lys Arg
225                 230
```

```
<210> SEQ ID NO 39
<211> LENGTH: 172
<212> TYPE: PRT
<213> ORGANISM: Trypanosoma cruzi

<400> SEQUENCE: 39

Ala Arg Glu Lys Arg Lys Gln Thr Asn Lys Ile Lys Asn Ser Lys Ser
  1               5                  10                  15

Ile Thr Ser Thr Met Ser Glu Ser Ala Phe Tyr Ala Phe Ala Ser
             20                  25                  30

Phe Gly Gly Ala Pro Thr Lys Glu Met Asp Asn Ala His Phe Ser Lys
             35                  40                  45

Met Leu Lys Glu Thr Lys Val Ile Gly Lys Gln Phe Thr Ser Thr Asp
 50                  55                  60

Ala Asp Leu Leu Phe Asn Lys Val Lys Ala Lys Gly Ala Arg Lys Ile
 65                  70                  75                  80

Thr Leu Ser Asp Phe Val Asp Lys Ala Val Pro Glu Ile Ala Ser Lys
                 85                  90                  95

Leu Lys Lys Ser Ala Glu Glu Leu Ile Ala Asp Ile Ser Ser Cys Ser
                100                 105                 110

Pro Glu Ala Arg Ala Thr Lys Ala Asp Ala Val Lys Phe His Asp Asp
            115                 120                 125

Lys Asn Met Tyr Thr Gly Val Tyr Lys Ala Gly Pro Thr Asn Val
        130                 135                 140

Asp Arg Asn Ser Gly Ser Leu Ser Gly Val Val Asp Arg Arg Val Ala
145                 150                 155                 160

Gln Thr Asp Val Arg Gly Thr Thr Ala Ser Gln Lys
                165                 170

<210> SEQ ID NO 40
<211> LENGTH: 233
<212> TYPE: PRT
<213> ORGANISM: Trypanosoma cruzi

<400> SEQUENCE: 40

Ala Arg Glu Leu Ser Ser Val Met Thr Leu Gly Lys Asn Lys Arg
  1               5                  10                  15

Ile Ser Lys Gly Gly Lys Arg Gly Lys Lys Thr Gln Glu Thr Met
             20                  25                  30

Ser Arg Lys Glu Trp Tyr Asp Val Val Ala Pro Lys Asn Phe Glu Val
             35                  40                  45

Arg Gln Phe Gly Lys Thr Ile Cys Asn Lys Thr Gln Gly Thr Lys Ile
 50                  55                  60

Ala Ala Asp Tyr Leu Arg Gly Arg Val Tyr Glu Ser Asn Leu Ala Asp
 65                  70                  75                  80

Leu Asn Lys Thr Gln Gly Asp Asp Ala Tyr Arg Lys Val Lys Phe
                 85                  90                  95

Val Val Gln Glu Val Gln Gly Arg Asn Leu Leu Thr Gln Phe His Ser
                100                 105                 110

Met Glu Met Thr Ser Asp Arg Val Tyr Phe Leu Leu Arg Lys Trp Cys
            115                 120                 125

Thr Thr Ile Glu Ala Ala Val Glu Thr Lys Thr Ala Asp Gly Tyr Thr
        130                 135                 140

Leu Arg Leu Phe Val Ile Ala Phe Thr Lys Lys Gln Ser Asn Gln Leu
145                 150                 155                 160

Ser Lys Asn Cys Tyr Ala Lys Thr Arg Leu Val Lys Trp Val Arg His
```

-continued

```
                    165                 170                 175
Arg Ile Thr Asn Leu Ile Arg Gln Arg Leu Ser Lys Val Asn Ile Asn
                180                 185                 190
Glu Ala Val Thr Leu Leu Thr Arg Asn Ile Leu Arg Asp Arg Leu Ala
            195                 200                 205
Lys Arg Cys Asn Pro Ile Val Pro Leu Arg Asp Leu Arg Ile Arg Lys
        210                 215                 220
Val Lys Val Val Arg Thr Pro Arg Phe
225                 230
```

<210> SEQ ID NO 41
<211> LENGTH: 128
<212> TYPE: PRT
<213> ORGANISM: Trypanosoma cruzi

<400> SEQUENCE: 41

```
Met Gln Ile Phe Val Lys Thr Leu Thr Gly Lys Thr Ile Ala Leu Glu
1               5                   10                  15
Val Glu Ser Ser Asp Thr Ile Glu Asn Val Lys Ala Lys Ile Gln Asp
            20                  25                  30
Lys Glu Gly Ile Pro Pro Asp Gln Gln Arg Leu Ile Phe Ala Gly Lys
        35                  40                  45
Gln Leu Glu Asp Gly Arg Thr Leu Ala Asp Tyr Asn Ile Gln Lys Glu
    50                  55                  60
Ser Thr Leu His Leu Val Leu Arg Leu Arg Gly Gly Val Met Glu Pro
65                  70                  75                  80
Thr Leu Glu Ala Leu Ala Lys Lys Tyr Asn Trp Glu Lys Lys Val Cys
                85                  90                  95
Arg Arg Cys Tyr Ala Arg Leu Pro Val Arg Ala Ser Asn Cys Arg Lys
            100                 105                 110
Lys Ala Cys Gly His Cys Ser Asn Leu Arg Met Lys Lys Lys Leu Arg
        115                 120                 125
```

<210> SEQ ID NO 42
<211> LENGTH: 145
<212> TYPE: PRT
<213> ORGANISM: Trypanosoma cruzi
<220> FEATURE:
<223> OTHER INFORMATION: Where any Xaa is an independently selected
      amino acid

<400> SEQUENCE: 42

```
Arg Leu Pro Pro Leu Leu Pro Ser Ser Asp Val Pro Glu Gly Met Glu
1               5                   10                  15
Leu Pro Pro Leu Leu Pro Ser Ser Asp Ile Pro Glu Gly Met Glu Leu
            20                  25                  30
Pro Pro Leu Leu Pro Ser Ser Asp Val Pro Ala Gly Met Glu Leu Thr
        35                  40                  45
Pro Leu Leu Pro Ser Ser Asp Val Pro Glu Gly Met Glu Leu Pro Pro
    50                  55                  60
Leu Leu Pro Ser Ser Asp Val Pro Ala Gly Met Glu Leu Pro Pro Leu
65                  70                  75                  80
Xaa Pro Ser Ser Asp Val Pro Ala Gly Met Glu Leu Pro Pro Leu Leu
                85                  90                  95
Pro Ser Ser Asp Val Pro Ala Xaa Ile Glu Leu Pro Pro Leu Ile Ser
            100                 105                 110
Xaa Leu Gly Arg Thr Xaa Arg Xaa Gly Asp Xaa Ser Ser Xaa Ser Cys
```

```
                  115                 120                 125
Leu Gly Arg Xaa Xaa Arg Xaa Arg Xaa Ala Pro Leu Xaa Pro Xaa Ser
    130                 135                 140
Glu
145

<210> SEQ ID NO 43
<211> LENGTH: 186
<212> TYPE: PRT
<213> ORGANISM: Trypanosoma cruzi

<400> SEQUENCE: 43

Glu Lys Glu Arg Arg Phe Pro Thr Lys Thr Ala Arg Ala Asp Pro Thr
  1               5                  10                  15

Thr Thr Lys Gln Leu Ile Ile Arg Ala Leu Gln Asn Ile Ser Leu Ala
             20                  25                  30

Phe Gly Ile Glu Pro Ser Ser Thr Val Lys Tyr Ala Glu Ser Thr Gln
         35                  40                  45

Glu Glu Asn Gly Lys Arg Ser Gln Ser Glu Ala Glu Glu Arg Ala Arg
     50                  55                  60

Arg Glu Ala Glu Glu Arg Ala Arg Arg Glu Ala Glu Glu Arg Ala Gln
 65                  70                  75                  80

Arg Glu Ala Glu Glu Arg Ala Gln Arg Glu Ala Glu Glu Arg Ala Arg
                 85                  90                  95

Arg Glu Ala Glu Lys Arg Ala Arg Arg Glu Ala Lys Glu Arg Ala Trp
                100                 105                 110

Gln Glu Ala Glu Glu Arg Ala Gln Arg Glu Ala Glu Glu Arg Ala Arg
            115                 120                 125

Arg Glu Ala Glu Glu Arg Ala Arg Arg Glu Val Glu Glu Arg Ala Arg
        130                 135                 140

Gln Glu Ala Glu Glu Leu Ala Arg Gln Glu Ser Glu Glu Arg Ala Arg
145                 150                 155                 160

Gln Glu Ala Glu Glu Arg Ala Trp Gln Glu Ala Glu Glu Arg Ala Gln
                165                 170                 175

Arg Glu Ala Glu Glu Arg Ala Gln Arg Ala
            180                 185

<210> SEQ ID NO 44
<211> LENGTH: 106
<212> TYPE: PRT
<213> ORGANISM: Trypanosoma cruzi
<220> FEATURE:
<223> OTHER INFORMATION: Where any Xaa is an independently selected
      amino acid

<400> SEQUENCE: 44

Gly Arg Gly Arg Ala Lys Ala Thr Asn Ser Arg Cys Arg Arg Val Arg
  1               5                  10                  15

Gly Arg Ala Glu Ala Thr Ser Ser Arg Arg Ser Gly Arg Gly Arg
             20                  25                  30

Ala Lys Ala Thr Ser Ser Arg Cys Arg Arg Val Arg Gly Arg Val Glu
         35                  40                  45

Ala Thr Asn Ser Arg Cys Arg Arg Gly Gly Arg Ala Lys Val Thr
     50                  55                  60

Ser Ser Arg Xaa Arg Arg Val Xaa Gly Arg Xaa Xaa Xaa Thr Ser Xaa
 65                  70                  75                  80

Arg Xaa Arg Arg Xaa Arg Gly Arg Xaa Xaa Val Thr Ser Arg Arg Xaa
```

-continued

```
                85                  90                  95

Arg Arg Xaa Xaa Gly Arg Gly Asp Val Thr
            100                 105

<210> SEQ ID NO 45
<211> LENGTH: 141
<212> TYPE: PRT
<213> ORGANISM: Trypanosoma cruzi

<400> SEQUENCE: 45

Ser Ile Pro Val Glu Ile Asp Ile Arg Asn Gln Asp Phe Ser Phe Leu
  1               5                  10                  15

Asp Pro Ala Pro Glu Gly Ile Pro Ile Gln Asp Ile His Leu Met Gly
             20                  25                  30

Asp Ser Ala Phe Ala Ala Ser Ala Arg Glu Arg Met Lys Leu Lys Arg
         35                  40                  45

Asn Pro Val Ala Asn Ala Ser Lys Ile Ser Ala Leu Glu Glu Glu Met
     50                  55                  60

Asp Gln Arg Ala His Val Leu Ala Lys Gln Val Arg Asp Lys Glu Arg
 65                  70                  75                  80

Thr Phe Leu Asp Pro Glu Pro Gly Val Pro Leu Glu Leu Leu Ser
                 85                  90                  95

Leu Asn Glu Asn Glu Ala Ser Gln Glu Leu Glu Arg Glu Leu Arg Ala
            100                 105                 110

Leu Asn Arg Lys Pro Arg Lys Asp Ala Lys Ala Ile Val Ala Leu Glu
        115                 120                 125

Asp Asp Val Arg Asp Glu His Thr Cys Leu Pro Arg Ser
    130                 135                 140

<210> SEQ ID NO 46
<211> LENGTH: 27
<212> TYPE: PRT
<213> ORGANISM: Trypanosoma cruzi

<400> SEQUENCE: 46

Arg Lys Met Ser Gly Thr Ser Leu Leu Ala Pro Gln Pro Glu Gly Val
  1               5                  10                  15

Pro Val Ser Glu Leu Ser Leu Asp Leu Asp Glu
             20                  25

<210> SEQ ID NO 47
<211> LENGTH: 117
<212> TYPE: PRT
<213> ORGANISM: Trypanosoma cruzi

<400> SEQUENCE: 47

Leu Leu Ala Leu Leu Gln Gly Leu Val Gln Leu Arg Thr Gln Ile His
  1               5                  10                  15

Gly Val Arg Pro Ala Leu Leu Pro Glu Ser Gly Gln Phe Leu Gly Gly
             20                  25                  30

Ser Leu Gln Leu Ala Met His Leu Leu Ala Leu Leu Gln Gly Leu Val
         35                  40                  45

Gln Leu Arg Thr Gln Ile His Gly Val Arg Pro Ala Leu Leu Pro Glu
     50                  55                  60

Ser Gly Gln Phe Leu Gly Gly Ser Leu Gln Leu Ala Met His Leu Leu
 65                  70                  75                  80

Ala Leu Leu Gln Gly Leu Val Gln Leu Arg Thr Gln Ile His Gly Val
                 85                  90                  95
```

Arg Pro Ala Leu Leu Pro Glu Ser Gly Gln Phe Leu Gly Gly Ser Leu
                100                 105                 110

Gln Leu Ala Thr His
        115

<210> SEQ ID NO 48
<211> LENGTH: 117
<212> TYPE: PRT
<213> ORGANISM: Trypanosoma cruzi

<400> SEQUENCE: 48

Ser Ser Arg Cys Cys Lys Ala Ser Ser Cys Ala Arg Arg Phe Thr
 1               5                  10                  15

Val Ser Ala Pro Leu Cys Ser Arg Ala Ala Ser Ser Val Val
                20                  25                  30

Arg Phe Ser Ser Arg Cys Thr Ser Ser Arg Cys Cys Lys Ala Ser Ser
                35                  40                  45

Ser Cys Ala Arg Arg Phe Thr Val Ser Ala Pro Leu Cys Ser Arg Arg
         50                  55                  60

Ala Gly Ser Ser Ser Val Val Arg Phe Ser Ser Arg Cys Thr Ser Ser
 65                  70                  75                  80

Arg Cys Cys Lys Ala Ser Ser Ser Cys Ala Arg Arg Phe Thr Val Ser
                85                  90                  95

Ala Pro Leu Cys Ser Arg Arg Ala Gly Ser Ser Ser Val Val Arg Phe
                100                 105                 110

Ser Ser Arg Arg Thr
        115

<210> SEQ ID NO 49
<211> LENGTH: 117
<212> TYPE: PRT
<213> ORGANISM: Trypanosoma cruzi

<400> SEQUENCE: 49

Pro Pro Arg Ala Ala Ala Arg Pro Arg Pro Ala Ala His Ala Asp Ser
 1               5                  10                  15

Arg Cys Pro Pro Arg Ser Ala Pro Gly Glu Arg Pro Val Pro Arg Trp
                20                  25                  30

Phe Ala Ser Ala Arg Asp Ala Pro Pro Arg Ala Ala Ala Arg Pro Arg
                35                  40                  45

Pro Ala Ala His Ala Asp Ser Arg Cys Pro Pro Arg Ser Ala Pro Gly
         50                  55                  60

Glu Arg Ala Val Pro Arg Trp Phe Ala Ser Ala Arg Asp Ala Pro Pro
 65                  70                  75                  80

Arg Ala Ala Ala Arg Pro Arg Pro Ala Ala His Ala Asp Ser Arg Cys
                85                  90                  95

Pro Pro Arg Ser Ala Pro Gly Glu Arg Ala Val Pro Arg Trp Phe Ala
                100                 105                 110

Ser Ala Arg Asp Ala
        115

<210> SEQ ID NO 50
<211> LENGTH: 207
<212> TYPE: PRT
<213> ORGANISM: Trypanosoma cruzi

<400> SEQUENCE: 50

-continued

```
Ala Glu Pro Lys Pro Ala Glu Pro Lys Ser Ala Glu Pro Lys Pro Ala
 1               5                   10                  15

Glu Pro Lys Ser Ala Glu Pro Lys Pro Ala Glu Pro Lys Ser Ala Glu
            20                  25                  30

Pro Lys Pro Ala Glu Pro Lys Ser Ala Gly Pro Lys Pro Ala Glu Pro
        35                  40                  45

Lys Ser Ala Glu Pro Lys Pro Ala Glu Pro Lys Ser Ala Glu Pro Lys
    50                  55                  60

Pro Ala Glu Pro Lys Ser Ala Glu Pro Lys Pro Ala Glu Pro Lys Ser
65                  70                  75                  80

Ala Glu Pro Lys Pro Ala Glu Ser Lys Ser Ala Glu Pro Lys Pro Ala
                85                  90                  95

Glu Pro Lys Ser Ala Glu Pro Lys Pro Ala Glu Ser Lys Ser Ala Glu
            100                 105                 110

Pro Lys Pro Ala Glu Pro Lys Ser Ala Glu Pro Lys Pro Ala Glu Pro
        115                 120                 125

Lys Ser Ala Glu Pro Lys Pro Ala Glu Pro Lys Ser Ala Glu Pro Lys
    130                 135                 140

Pro Ala Glu Pro Lys Ser Ala Glu Pro Lys Pro Ala Glu Ser Lys Ser
145                 150                 155                 160

Ala Gly Pro Lys Pro Ala Glu Pro Lys Ser Ala Glu Pro Lys Pro Ala
                165                 170                 175

Glu Pro Lys Ser Ala Glu Pro Lys Pro Ala Glu Pro Lys Ser Ala Glu
            180                 185                 190

Pro Lys Pro Ala Glu Pro Lys Ser Ala Glu Pro Lys Pro Ala Glu
        195                 200                 205

<210> SEQ ID NO 51
<211> LENGTH: 263
<212> TYPE: PRT
<213> ORGANISM: Trypanosoma cruzi
<220> FEATURE:
<223> OTHER INFORMATION: Where any Xaa is an independently selected
      amino acid

<400> SEQUENCE: 51

Arg Arg Gly Tyr Pro Arg Ser Arg Met Pro Ser Lys Glu Leu Trp Met
 1               5                   10                  15

Arg Arg Leu Arg Ile Leu Arg Leu Leu Arg Lys Tyr Arg Glu Glu
            20                  25                  30

Lys Lys Ile Asp Arg His Ile Tyr Arg Glu Leu Tyr Val Lys Ala Lys
        35                  40                  45

Gly Asn Val Phe Arg Asn Lys Arg Asn Leu Met Glu His Ile His Lys
    50                  55                  60

Val Lys Asn Glu Lys Lys Lys Glu Arg Gln Leu Ala Glu Gln Leu Ala
65                  70                  75                  80

Ala Asn Ala Xaa Lys Asp Glu Gln His Arg His Lys Ala Arg Lys Gln
                85                  90                  95

Glu Leu Arg Lys Arg Glu Lys Asp Arg Glu Arg Ala Arg Arg Glu Asp
            100                 105                 110

Ala Ala Ala Ala Ala Ala Lys Gln Lys Ala Ala Lys Lys Ala
        115                 120                 125

Ala Ala Pro Ser Gly Lys Lys Ser Ala Lys Ala Ile Ala Pro Ala
    130                 135                 140

Lys Ala Ala Ala Ala Pro Ala Lys Ala Ala Ala Pro Ala Lys Ala
145                 150                 155                 160
```

-continued

Ala Ala Ala Pro Ala Lys Ala Ala Ala Pro Ala Lys Ala Ala Ala
              165                 170                 175

Ala Pro Ala Lys Ala Ala Thr Ala Pro Ala Lys Ala Ala Ala Pro
            180                 185                 190

Ala Lys Thr Ala Ala Ala Pro Ala Lys Ala Ala Pro Ala Lys Ala
        195                 200                 205

Ala Ala Ala Pro Ala Lys Ala Ala Thr Ala Pro Ala Lys Ala Ala Ala
    210                 215                 220

Ala Pro Ala Lys Ala Ala Thr Ala Pro Ala Lys Ala Ala Thr Ala Pro
225                 230                 235                 240

Ala Lys Ala Ala Ala Pro Ala Lys Ala Ala Thr Ala Pro Val Gly
                245                 250                 255

Lys Lys Ala Gly Gly Lys Lys
            260

<210> SEQ ID NO 52
<211> LENGTH: 442
<212> TYPE: PRT
<213> ORGANISM: Trypanosoma cruzi

<400> SEQUENCE: 52

Asp Phe Ile Trp Tyr Lys Val Val Ala Leu Leu Val Val Ile Thr Ser
 1               5                  10                  15

Asn Gly Asp Asp Val Ser Val Tyr Thr Ala Thr Ile Lys Glu Phe Tyr
            20                  25                  30

Arg Tyr Leu Trp Ile Phe Val Pro Val Ser Leu Phe Ser Ile Ile Ile
        35                  40                  45

Tyr Phe Val Ser Ile Phe Cys Phe Pro Ala Ser Tyr Gly Leu Phe Phe
    50                  55                  60

Ser Ser Phe Leu Lys Phe Gln Leu Leu Asn His Lys His Pro Val
65                  70                  75                  80

Leu Gln Pro Pro His Gln Met Val Ser Leu Lys Leu Gln Ala Arg Leu
                85                  90                  95

Ala Ala Asp Ile Leu Arg Cys Gly Arg His Arg Val Trp Leu Asp Pro
            100                 105                 110

Asn Glu Ala Ser Glu Ile Ser Asn Ala Asn Ser Arg Lys Ser Val Arg
        115                 120                 125

Lys Leu Ile Lys Asp Gly Leu Ile Ile Arg Lys Pro Val Lys Val His
    130                 135                 140

Ser Arg Ser Arg Trp Arg His Met Lys Glu Ala Lys Ser Met Gly Arg
145                 150                 155                 160

His Glu Gly Ala Gly Arg Arg Glu Gly Thr Arg Glu Ala Arg Met Pro
                165                 170                 175

Ser Lys Glu Leu Trp Met Arg Arg Leu Arg Ile Leu Arg Arg Leu Leu
            180                 185                 190

Arg Lys Tyr Arg Glu Glu Lys Lys Ile Asp Arg His Ile Tyr Arg Glu
        195                 200                 205

Leu Tyr Val Lys Ala Lys Gly Asn Val Phe Arg Asn Lys Arg Asn Leu
    210                 215                 220

Met Glu His Ile His Lys Val Lys Asn Glu Lys Lys Glu Arg Gln
225                 230                 235                 240

Leu Ala Glu Gln Leu Ala Ala Lys Arg Leu Lys Asp Glu Gln His Arg
                245                 250                 255

His Lys Ala Arg Lys Gln Glu Leu Arg Lys Arg Glu Lys Asp Arg Glu

```
                    260                 265                 270
Arg Ala Arg Arg Glu Asp Ala Ala Ala Ala Ala Ala Lys Gln Lys
            275                 280                 285
Ala Ala Ala Lys Lys Ala Ala Pro Ser Gly Lys Lys Ser Ala Lys
            290                 295                 300
Ala Ala Ala Pro Ala Lys Ala Ala Ala Pro Ala Lys Ala Ala Ala
305                 310                 315                 320
Pro Pro Ala Lys Thr Ala Ala Pro Ala Lys Ala Ala Pro Ala
                325                 330                 335
Lys Ala Ala Ala Pro Pro Ala Lys Ala Ala Pro Pro Ala Lys Thr
            340                 345                 350
Ala Ala Pro Pro Ala Lys Thr Ala Ala Pro Pro Ala Lys Ala Ala Ala
            355                 360                 365
Pro Pro Ala Lys Ala Ala Ala Pro Pro Ala Lys Ala Ala Ala Pro Pro
        370                 375                 380
Ala Lys Ala Ala Ala Pro Ala Lys Ala Ala Ala Pro Ala Lys
385                 390                 395                 400
Ala Ala Ala Pro Pro Ala Lys Ala Ala Pro Pro Ala Lys Ala Ala
                405                 410                 415
Ala Pro Pro Ala Lys Ala Ala Pro Pro Ala Lys Ala Ala Ala Ala
                420                 425                 430
Pro Val Gly Lys Lys Ala Gly Gly Lys Lys
        435                 440
```

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: TcD antigenic epitope

<400> SEQUENCE: 53

```
Ala Glu Pro Lys Ser Ala Glu Pro Lys Pro Ala Glu Pro Lys Ser
 1               5                  10                  15
```

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: TcD antigenic epitope

<400> SEQUENCE: 54

```
Ala Glu Pro Lys Pro Ala Glu Pro Lys Ser Ala Glu Pro Lys Pro
 1               5                  10                  15
```

<210> SEQ ID NO 55
<211> LENGTH: 21
<212> TYPE: PRT
<213> ORGANISM: Artificial Sequence
<220> FEATURE:
<223> OTHER INFORMATION: Description of Artificial Sequence: TcE antigenic epitope

<400> SEQUENCE: 55

```
Lys Ala Ala Ile Ala Pro Ala Lys Ala Ala Ala Pro Ala Lys Ala
 1               5                  10                  15
Ala Thr Ala Pro Ala
            20
```

```
<210> SEQ ID NO 56
<211> LENGTH: 21
<212> TYPE: PRT
<213> ORGANISM: Artificial Sequence
<220> FEATURE:
<223> OTHER INFORMATION: Description of Artificial Sequence: TcE
      antigenic epitope

<400> SEQUENCE: 56

Lys Ala Ala Ala Ala Pro Ala Lys Ala Ala Ala Ala Pro Ala Lys Ala
 1               5                  10                  15

Ala Ala Ala Pro Ala
            20

<210> SEQ ID NO 57
<211> LENGTH: 22
<212> TYPE: PRT
<213> ORGANISM: Artificial Sequence
<220> FEATURE:
<223> OTHER INFORMATION: Description of Artificial Sequence: PEP2
      antigenic epitope

<400> SEQUENCE: 57

Gly Asp Lys Pro Ser Pro Phe Gly Gln Ala Ala Ala Gly Asp Lys Pro
 1               5                  10                  15

Ser Pro Phe Gly Gln Ala
            20

<210> SEQ ID NO 58
<211> LENGTH: 21
<212> TYPE: PRT
<213> ORGANISM: Artificial Sequence
<220> FEATURE:
<223> OTHER INFORMATION: Description of Artificial Sequence: TcE
      antigenic epitope

<400> SEQUENCE: 58

Lys Ala Ala Ala Ala Pro Ala Lys Ala Ala Ala Ala Pro Ala Lys Ala
 1               5                  10                  15

Ala Ala Ala Pro Ala
            20

<210> SEQ ID NO 59
<211> LENGTH: 21
<212> TYPE: PRT
<213> ORGANISM: Artificial Sequence
<220> FEATURE:
<223> OTHER INFORMATION: Description of Artificial Sequence: TcE
      antigenic epitope

<400> SEQUENCE: 59

Lys Ala Ala Thr Ala Pro Ala Lys Ala Ala Thr Ala Pro Ala Lys Ala
 1               5                  10                  15

Ala Thr Ala Pro Ala
            20

<210> SEQ ID NO 60
<211> LENGTH: 21
<212> TYPE: PRT
<213> ORGANISM: Artificial Sequence
<220> FEATURE:
<223> OTHER INFORMATION: Description of Artificial Sequence: TcE
      antigenic epitope

<400> SEQUENCE: 60
```

```
Lys Ala Ala Ile Ala Pro Ala Lys Ala Ala Ile Ala Pro Ala Lys Ala
  1               5                  10                  15

Ala Ile Ala Pro Ala

20

<210> SEQ ID NO 65
<211> LENGTH: 618
<212> TYPE: PRT
<213> ORGANISM: Trypanosoma cruzi

<400> SEQUENCE: 65

| Lys | Ala | Val | Asp | Pro | Phe | Gln | Gly | Thr | Thr | Pro | Pro | Tyr | Lys | Trp |
|---|---|---|---|---|---|---|---|---|---|---|---|---|---|---|
| 1 | | | | 5 | | | | | 10 | | | | | 15 |

| Gln | Glu | Met | Thr | Gly | Ser | Glu | Ala | Ala | Gly | Ser | Leu | Cys | Val | Pro |
|---|---|---|---|---|---|---|---|---|---|---|---|---|---|---|
| | | | 20 | | | | | 25 | | | | | 30 | |

| Ser | Leu | Ala | Glu | Val | Ala | Gly | Val | Phe | Ala | Val | Ala | Glu | Ala | Gln |
|---|---|---|---|---|---|---|---|---|---|---|---|---|---|---|
| | | 35 | | | | | 40 | | | | | 45 | | |

| Arg | Ser | Glu | Arg | Asp | Glu | Ala | Cys | Gly | His | Ala | Ala | Ile | Ala | Thr | Thr |
|---|---|---|---|---|---|---|---|---|---|---|---|---|---|---|---|
| | 50 | | | | | 55 | | | | | 60 | | | | |

| His | Ile | Glu | Thr | Gly | Gly | Gly | Ser | Lys | Ala | Ile | Ser | Ala | Met | Asp |
|---|---|---|---|---|---|---|---|---|---|---|---|---|---|---|
| 65 | | | | | 70 | | | | | 75 | | | | 80 |

| Ala | Gly | Val | Phe | Leu | Val | Glu | Leu | Val | Asp | Ala | Ala | Ser | Gly | Thr | Ile |
|---|---|---|---|---|---|---|---|---|---|---|---|---|---|---|---|
| | | | | 85 | | | | | 90 | | | | | 95 | |

| Arg | Thr | Arg | Glu | Lys | Met | Gln | Pro | Thr | Thr | Ile | Val | Ser | Gly | Asp | Thr |
|---|---|---|---|---|---|---|---|---|---|---|---|---|---|---|---|
| | | | | 100 | | | | | 105 | | | | | 110 | |

| Ile | Tyr | Met | Ala | Leu | Gly | Asp | Tyr | Glu | Lys | Lys | Thr | Ser | Gly | Gly | Arg |
|---|---|---|---|---|---|---|---|---|---|---|---|---|---|---|---|
| | | | 115 | | | | | 120 | | | | | 125 | | |

| Ala | Ala | Asp | Ala | Asp | Gly | Trp | Arg | Leu | Leu | Met | Arg | Gly | Thr | Leu |
|---|---|---|---|---|---|---|---|---|---|---|---|---|---|---|
| | | 130 | | | | | 135 | | | | | 140 | | |

| Thr | Glu | Asp | Gly | Gly | Gln | Lys | Lys | Ile | Met | Trp | Gly | Asp | Ile | Arg | Ala |
|---|---|---|---|---|---|---|---|---|---|---|---|---|---|---|---|
| 145 | | | | | 150 | | | | | 155 | | | | | 160 |

| Val | Asp | Pro | Val | Ala | Ile | Gly | Leu | Thr | Gln | Phe | Leu | Lys | Arg | Val | Ile |
|---|---|---|---|---|---|---|---|---|---|---|---|---|---|---|---|
| | | | | 165 | | | | | 170 | | | | | 175 | |

| Gly | Gly | Gly | Gly | Ser | Gly | Val | Val | Thr | Lys | Asn | Gly | Tyr | Leu | Val | Leu |
|---|---|---|---|---|---|---|---|---|---|---|---|---|---|---|---|
| | | | 180 | | | | | 185 | | | | | 190 | | |

| Pro | Met | Gln | Ala | Val | Glu | Lys | Asp | Gly | Arg | Ser | Val | Val | Leu | Ser | Met |
|---|---|---|---|---|---|---|---|---|---|---|---|---|---|---|---|
| | | 195 | | | | | 200 | | | | | 205 | | | |

| Arg | Phe | Asn | Met | Arg | Ile | Glu | Ala | Cys | Glu | Leu | Ser | Ser | Gly | Thr | Thr |
|---|---|---|---|---|---|---|---|---|---|---|---|---|---|---|---|
| | 210 | | | | | 215 | | | | | 220 | | | | |

| Gly | Ser | Asn | Cys | Lys | Glu | Pro | Ser | Ile | Ala | Asn | Leu | Glu | Gly | Asn | Leu |
|---|---|---|---|---|---|---|---|---|---|---|---|---|---|---|---|
| 225 | | | | | 230 | | | | | 235 | | | | | 240 |

| Ile | Leu | Ile | Thr | Ser | Cys | Ala | Ala | Gly | Tyr | Tyr | Glu | Val | Phe | Arg | Ser |
|---|---|---|---|---|---|---|---|---|---|---|---|---|---|---|---|
| | | | | 245 | | | | | 250 | | | | | 255 | |

| Leu | Asp | Ser | Gly | Thr | Ser | Trp | Glu | Met | Ser | Gly | Arg | Pro | Ile | Ser | Arg |
|---|---|---|---|---|---|---|---|---|---|---|---|---|---|---|---|
| | | | 260 | | | | | 265 | | | | | 270 | | |

| Val | Trp | Gly | Asn | Ser | Tyr | Gly | Arg | Lys | Gly | Tyr | Gly | Val | Arg | Cys | Gly |
|---|---|---|---|---|---|---|---|---|---|---|---|---|---|---|---|
| | | 275 | | | | | 280 | | | | | 285 | | | |

| Leu | Thr | Thr | Val | Thr | Ile | Glu | Gly | Arg | Glu | Val | Leu | Leu | Val | Thr | Thr |
|---|---|---|---|---|---|---|---|---|---|---|---|---|---|---|---|
| | 290 | | | | | 295 | | | | | 300 | | | | |

| Pro | Val | Tyr | Leu | Glu | Glu | Lys | Asn | Gly | Arg | Gly | Arg | Leu | His | Leu | Trp |
|---|---|---|---|---|---|---|---|---|---|---|---|---|---|---|---|
| 305 | | | | | 310 | | | | | 315 | | | | | 320 |

| Val | Thr | Asp | Gly | Ala | Arg | Val | His | Asp | Ala | Gly | Pro | Ile | Ser | Asp | Ala |
|---|---|---|---|---|---|---|---|---|---|---|---|---|---|---|---|
| | | | | 325 | | | | | 330 | | | | | 335 | |

| Ala | Asp | Asp | Ala | Ala | Ala | Ser | Ser | Leu | Leu | Tyr | Ser | Ser | Gly | Gly | Asn |
|---|---|---|---|---|---|---|---|---|---|---|---|---|---|---|---|
| | | | 340 | | | | | 345 | | | | | 350 | | |

| Leu | Ile | Ser | Leu | Tyr | Glu | Asn | Lys | Ser | Glu | Gly | Ser | Tyr | Gly | Leu | Val |
|---|---|---|---|---|---|---|---|---|---|---|---|---|---|---|---|
| | | | 355 | | | | | 360 | | | | | 365 | | |

```
Ala Val His Val Thr Thr Gln Leu Glu Arg Ile Lys Thr Val Leu Lys
    370                 375                 380

Arg Trp Gln Glu Leu Asp Glu Ala Leu Arg Thr Cys Arg Ser Thr Ala
385                 390                 395                 400

Thr Ile Asp Pro Val Arg Arg Gly Met Cys Ile Arg Pro Ile Leu Thr
                405                 410                 415

Asp Gly Leu Val Gly Tyr Leu Ser Gly Leu Ser Thr Gly Ser Glu Trp
            420                 425                 430

Met Asp Glu Tyr Leu Cys Val Asn Ala Thr Val His Gly Thr Val Arg
        435                 440                 445

Gly Phe Ser Asn Gly Val Thr Phe Glu Gly Pro Gly Ala Gly Ala Gly
    450                 455                 460

Trp Pro Val Ala Arg Ser Gly Gln Asn Gln Pro Tyr His Phe Leu His
465                 470                 475                 480

Lys Thr Phe Thr Leu Val Val Met Ala Val Ile His Asp Arg Pro Lys
                485                 490                 495

Lys Arg Thr Pro Ile Pro Leu Ile Arg Val Val Met Asp Asp Asn Asp
            500                 505                 510

Lys Thr Val Leu Phe Gly Val Phe Tyr Thr His Asp Gly Arg Trp Met
        515                 520                 525

Thr Val Ile His Ser Gly Gly Arg Gln Ile Leu Ser Thr Gly Trp Asp
    530                 535                 540

Pro Glu Lys Pro Cys Gln Val Val Leu Arg His Asp Thr Gly His Trp
545                 550                 555                 560

Asp Phe Tyr Val Asn Ala Arg Lys Ala Tyr Phe Gly Thr Tyr Lys Gly
                565                 570                 575

Leu Phe Ser Lys Gln Thr Val Phe His Thr Ser Asn Ser Thr Gly Arg
            580                 585                 590

Val Gly Lys Leu Gln Ser Pro Ala Ile Cys His Ser Ser Thr Pro Val
        595                 600                 605

Cys Ile Thr Glu Asp Ser Ile Pro Ser Ile
    610                 615

<210> SEQ ID NO 66
<211> LENGTH: 39
<212> TYPE: DNA
<213> ORGANISM: Trypanosoma cruzi

<400> SEQUENCE: 66
ggggacaaac cgtctccgtt ccaggctgct gctggtgac                        39

<210> SEQ ID NO 67
<211> LENGTH: 49
<212> TYPE: DNA
<213> ORGANISM: Trypanosoma cruzi

<400> SEQUENCE: 67
gagacggttt gtcaccagca gcagcctgga acggagacgg tttgtcccc             49

<210> SEQ ID NO 68
<211> LENGTH: 40
<212> TYPE: DNA
<213> ORGANISM: Trypanosoma cruzi

<400> SEQUENCE: 68
aaaccgtctc cgttcggtca ggctgctgaa ccgaaatctg                       40
```

```
<210> SEQ ID NO 69
<211> LENGTH: 40
<212> TYPE: DNA
<213> ORGANISM: Trypanosoma cruzi

<400> SEQUENCE: 69
ttcggttcag cagatttcgg ttcagcagcc tgaccgaacg                      40

<210> SEQ ID NO 70
<211> LENGTH: 51
<212> TYPE: DNA
<213> ORGANISM: Trypanosoma cruzi

<400> SEQUENCE: 70
ctgaaccgaa accggctgaa ccgaaaagcg ctctagatgc atgaattcca g         51

<210> SEQ ID NO 71
<211> LENGTH: 41
<212> TYPE: DNA
<213> ORGANISM: Trypanosoma cruzi

<400> SEQUENCE: 71
ctggaattca tgcatctaga gcgcttttcg gttcagccgg t                    41

<210> SEQ ID NO 72
<211> LENGTH: 49
<212> TYPE: DNA
<213> ORGANISM: Trypanosoma cruzi

<400> SEQUENCE: 72
aaagctgcta tcgctccggc taaagctgct gctgctccgg ctaaagctg            49

<210> SEQ ID NO 73
<211> LENGTH: 39
<212> TYPE: DNA
<213> ORGANISM: Trypanosoma cruzi

<400> SEQUENCE: 73
cggagcagca gcagctttag ccggagcgat agcagcttt                       39

<210> SEQ ID NO 74
<211> LENGTH: 29
<212> TYPE: DNA
<213> ORGANISM: Trypanosoma cruzi

<400> SEQUENCE: 74
ctaccgctcc ggccggctcg agatgcatg                                  29

<210> SEQ ID NO 75
<211> LENGTH: 43
<212> TYPE: DNA
<213> ORGANISM: Trypanosoma cruzi

<400> SEQUENCE: 75
aattcatgca tctcgagccg gccggagcgg tagcagcttt agc                  43

<210> SEQ ID NO 76
<211> LENGTH: 49
<212> TYPE: DNA
<213> ORGANISM: Trypanosoma cruzi

<400> SEQUENCE: 76
tcttctatgc cgtctggtac ctctgaagaa ggttctcgtg gtggttctt            49
```

```
<210> SEQ ID NO 77
<211> LENGTH: 39
<212> TYPE: DNA
<213> ORGANISM: Trypanosoma cruzi

<400> SEQUENCE: 77
acgagaacct tcttcagagg taccagacgg catagaaga                              39

<210> SEQ ID NO 78
<211> LENGTH: 26
<212> TYPE: DNA
<213> ORGANISM: Trypanosoma cruzi

<400> SEQUENCE: 78
ctatgccggc cggctcgaga tgcatg                                           26

<210> SEQ ID NO 79
<211> LENGTH: 40
<212> TYPE: DNA
<213> ORGANISM: Trypanosoma cruzi

<400> SEQUENCE: 79
aattcatgca tctcgagccg gccggcatag aagaaccacc                            40

<210> SEQ ID NO 80
<211> LENGTH: 23
<212> TYPE: DNA
<213> ORGANISM: Trypanosoma cruzi

<400> SEQUENCE: 80
ataccccggg gacaaccgtc tcc                                              23

<210> SEQ ID NO 81
<211> LENGTH: 26
<212> TYPE: DNA
<213> ORGANISM: Trypanosoma cruzi

<400> SEQUENCE: 81
cgccttagcc tggaattcat gcatct                                           26

<210> SEQ ID NO 82
<211> LENGTH: 85
<212> TYPE: PRT
<213> ORGANISM: Trypanosoma cruzi

<400> SEQUENCE: 82

Met Gly His His His His His His Gly Asp Lys Pro Ser Pro Phe Gln
  1               5                  10                  15

Ala Ala Ala Gly Asp Lys Pro Ser Pro Phe Gly Gln Ala Ala Glu Pro
             20                  25                  30

Lys Ser Ala Glu Pro Lys Pro Ala Glu Pro Lys Ser Lys Ala Ala Ile
         35                  40                  45

Ala Pro Ala Lys Ala Ala Ala Pro Ala Lys Ala Thr Ala Pro
     50                  55                  60

Ala Ser Ser Met Pro Ser Gly Thr Ser Glu Glu Gly Ser Arg Gly Gly
 65                  70                  75                  80

Ser Ser Met Pro Ala
             85

<210> SEQ ID NO 83
<211> LENGTH: 49
```

<212> TYPE: DNA
<213> ORGANISM: Artificial Sequence
<220> FEATURE:
<223> OTHER INFORMATION: Made in laboratory

<400> SEQUENCE: 83
aaaccgtctc cgttcggtca ggctggttgt ggtgctgaac cgaaatctg        49

<210> SEQ ID NO 84
<211> LENGTH: 49
<212> TYPE: DNA
<213> ORGANISM: Artificial sequence
<220> FEATURE:
<223> OTHER INFORMATION: Made in laboratory

<400> SEQUENCE: 84
ttcggttcag cagatttcgg ttcagcacca caaccagcct gaccgaacg        49

<210> SEQ ID NO 85
<211> LENGTH: 43
<212> TYPE: DNA
<213> ORGANISM: Artificial Sequence
<220> FEATURE:
<223> OTHER INFORMATION: Made in laboratory

<400> SEQUENCE: 85
ctgaaccgaa accggctgaa ccgaaaagcg ctctagatgc atg        43

<210> SEQ ID NO 86
<211> LENGTH: 37
<212> TYPE: DNA
<213> ORGANISM: Artificial Sequence
<220> FEATURE:
<223> OTHER INFORMATION: Made in laboratory

<400> SEQUENCE: 86
aattcatgca tctagagcgc ttttcggttc agccggt        37

<210> SEQ ID NO 87
<211> LENGTH: 49
<212> TYPE: DNA
<213> ORGANISM: Artificial Sequence
<220> FEATURE:
<223> OTHER INFORMATION: Made in laboratory

<400> SEQUENCE: 87
ggttgtggta aagctgctat cgctccggct aaagctgctg ctgctccgg        49

<210> SEQ ID NO 88
<211> LENGTH: 39
<212> TYPE: DNA
<213> ORGANISM: Artificial Sequence
<220> FEATURE:
<223> OTHER INFORMATION: Made in laboratory

<400> SEQUENCE: 88
agcagcttta gccggagcga tagcagcttt accacaacc        39

<210> SEQ ID NO 89
<211> LENGTH: 38
<212> TYPE: DNA
<213> ORGANISM: Artificial Sequence
<220> FEATURE:
<223> OTHER INFORMATION: Made in laboratory

<400> SEQUENCE: 89

```
ctaaagctgc taccgctccg gccggctcga gatgcatg                              38
```

<210> SEQ ID NO 90
<211> LENGTH: 52
<212> TYPE: DNA
<213> ORGANISM: Artificial Sequence
<220> FEATURE:
<223> OTHER INFORMATION: Made in laboratory

<400> SEQUENCE: 90

```
aattcatgca tctcgagccg gccggagcgg tagcagcttt agccggagca gc             52
```

<210> SEQ ID NO 91
<211> LENGTH: 44
<212> TYPE: DNA
<213> ORGANISM: Artificial Sequence
<220> FEATURE:
<223> OTHER INFORMATION: Made in laboratory

<400> SEQUENCE: 91

```
ggttgtggtt cttctatgcc gtctggtacc tctgaagaag gttc                      44
```

<210> SEQ ID NO 92
<211> LENGTH: 34
<212> TYPE: DNA
<213> ORGANISM: Artificial Sequence
<220> FEATURE:
<223> OTHER INFORMATION: Made in laboratory

<400> SEQUENCE: 92

```
cagaggtacc agacggcata gaagaaccac aacc                                 34
```

<210> SEQ ID NO 93
<211> LENGTH: 27
<212> TYPE: DNA
<213> ORGANISM: Artificial Sequence
<220> FEATURE:
<223> OTHER INFORMATION: Made in laboratory

<400> SEQUENCE: 93

```
tcgtggtggt tcttctatgc cggcctg                                         27
```

<210> SEQ ID NO 94
<211> LENGTH: 41
<212> TYPE: DNA
<213> ORGANISM: Artificial Sequence
<220> FEATURE:
<223> OTHER INFORMATION: Made in laboratory

<400> SEQUENCE: 94

```
aattcaggcc ggcatagaag aaccaccacg agaaccttct t                         41
```

<210> SEQ ID NO 95
<211> LENGTH: 94
<212> TYPE: PRT
<213> ORGANISM: Trypanosoma cruzi

<400> SEQUENCE: 95

```
Met Gly His His His His His His Gly Asp Lys Pro Ser Pro Phe Gln
  1               5                  10                  15

Ala Ala Ala Gly Asp Lys Pro Ser Pro Phe Gly Gln Ala Gly Cys Gly
             20                  25                  30

Ala Glu Pro Lys Ser Ala Glu Pro Lys Pro Ala Glu Pro Lys Ser Gly
         35                  40                  45
```

-continued

```
Cys Gly Lys Ala Ala Ile Ala Pro Ala Lys Ala Ala Ala Ala Pro Ala
    50              55                  60

Lys Ala Ala Thr Ala Pro Ala Gly Cys Gly Ser Ser Met Pro Ser Gly
65              70                  75                  80

Thr Ser Glu Glu Gly Ser Arg Gly Gly Ser Ser Met Pro Ala
                85                  90
```

COMPOUNDS AND METHODS FOR THE DETECTION AND PREVENTION OF *T.CRUZI* INFECTION

CROSS REFERENCE TO RELATED APPLICATIONS

This application is a continuation-in-part of U.S. application Ser. No. 08/993,674, filed Dec. 18, 1997, which is a continuation-in-part of U.S. application Ser. No. 08/834,306, filed Apr. 15, 1997, now U.S. Pat. No. 6,054,135, which claims priority from PCT Application No. PCT/US96/18624, filed Nov. 14, 1996, which claims priority from U.S. application Ser. No. 08/557,309, now U.S. Pat. No. 5,916,572, filed Nov. 14, 1995.

TECHNICAL FIELD

The present invention relates generally to the diagnosis of *T. cruzi* infection. The invention is more particularly related to the use of one or more *T. cruzi* antigenic peptides, or antibodies thereto, in methods and diagnostic kits to screen individuals and blood supplies for *T. cruzi* infection. The invention is also directed to vaccine compositions for immunizing an individual to prevent Chagas' disease.

BACKGROUND OF THE INVENTION

Protozoan parasites are a serious health threat in many areas of the world. *Trypanosoma cruzi* (*T. cruzi*) is one such parasite that infects millions of individuals, primarily in Central and South America. Infections with this parasite can cause Chagas' disease, which may result in chronic heart disease and a variety of immune system disorders. It is estimated that 18 million people in Latin America are infected with *T. cruzi*, but there is no reliable treatment for the clinical manifestations of infection. No vaccine for the prevention of Chagas' disease is currently available.

The most significant route of transmission in areas where the disease is endemic is through contact with an infected triatomid bug. In other areas, however, blood transfusions are the dominant means of transmission. To inhibit the transmission of *T. cruzi* in such regions, it is necessary to develop accurate methods for diagnosing *T. cruzi* infection in individuals and for screening blood supplies. Blood bank screening is particularly important in South America, where 0.1%–62% of samples may be infected and where the parasite is frequently transmitted by blood transfusion. There is also increasing concern that the blood supply in certain U.S. cities may be contaminated with *T. cruzi* parasites.

The diagnosis of *T. cruzi* infection has been problematic, since accurate methods for detecting the parasite that are suitable for routine use have been unavailable. During the acute phase of infection, which may last for decades, the infection may remain quiescent and the host may be asymptomatic. As a result, serological tests for *T. cruzi* infection are the most reliable and the most commonly used.

Such diagnoses are complicated, however, by the complex life cycle of the parasite and the diverse immune responses of the host. The parasite passes through an epimastigote stage in the insect vector and two main stages in the mammalian host. One host stage is present in blood (the trypomastigote stage) and a second stage is intracellular (the amastigote stage). The multiple stages result in a diversity of antigens presented by the parasite during infection. In addition, immune responses to protozoan infection are complex, involving both humoral and cell-mediated responses to the array of parasite antigens.

While detecting antibodies against parasite antigens is the most common and reliable method of diagnosing clinical and subclinical infections, current tests are expensive and difficult. Most serological tests use whole or lysed *T. cruzi* and require positive results on two of three tests, including complement fixation, indirect immunofluorescence, passive agglutination or ELISA, to accurately detect *T. cruzi* infection. The cost and difficulty of such tests has prevented the screening of blood or sera in many endemic areas.

Accordingly, there is a need in the art for more specific and sensitive methods of detecting *T. cruzi* infections in blood supplies and individuals. The present invention fulfills these needs and further provides other related advantages.

SUMMARY OF THE INVENTION

Briefly stated, this invention provides compounds and methods for detecting and protecting against *T. cruzi* infection in individuals and in blood supplies, and for screening for *T. cruzi* infection in biological samples. In one aspect, the present invention provides methods for detecting *T. cruzi* infection in a biological sample, comprising (a) contacting the biological sample with a polypeptide comprising an epitope of a *T. cruzi* antigen having an amino acid sequence encoded by a nucleotide sequence recited in SEQ ID NO:1–SEQ ID NO:22, or a variant of such an antigen that differs only in conservative substitutions and/or modifications; and (b) detecting in the biological sample the presence of antibodies that bind to the polypeptide, therefrom detecting *T. cruzi* infection in the biological sample.

In another aspect of this invention, polypeptides are provided comprising an epitope of a *T. cruzi* antigen having an amino acid sequence encoded by a nucleotide sequence recited in SEQ ID NO:1–SEQ ID NO:21, or a variant of such an antigen that differs only in conservative substitutions and/or modifications.

Within related aspects, DNA sequences encoding the above polypeptides, expression vectors comprising these DNA sequences and host cells transformed or transfected with such expression vectors are also provided.

In another aspect, the present invention provides diagnostic kits for detecting *T. cruzi* infection in a biological sample, comprising (a) a polypeptide comprising an epitope of a *T. cruzi* antigen having an amino acid sequence encoded by a nucleotide sequence recited in SEQ ID NO:1–SEQ ID NO:22, or a variant of such an antigen that differs only in conservative substitutions and/or modifications; and (b) a detection reagent.

In yet another aspect of the invention, methods for detecting the presence of *T. cruzi* infection in a biological sample are provided, comprising (a) contacting a biological sample with a monoclonal antibody that binds to an epitope of a *T. cruzi* antigen having an amino acid sequence encoded by a nucleotide sequence recited in SEQ ID NO:1–SEQ ID NO:22, or a variant of such an antigen that differs only in conservative substitutions and/or modifications; and (b) detecting in the biological sample the presence of *T. cruzi* parasites that bind to the monoclonal antibody.

Within related aspects, pharmaceutical compositions comprising the above polypeptides and a physiologically acceptable carrier, and vaccines comprising the above polypeptides in combination with an adjuvant, are also provided.

The present invention also provides, within other aspects, methods for inducing protective immunity against Chagas' disease in a patient, comprising administering to a patient a pharmaceutical composition or vaccine as described above.

Within other aspects, the present invention provides methods for detecting *T. cruzi* infection in a biological sample, comprising (a) contacting the biological sample with a first polypeptide comprising an epitope of a *T. cruzi* antigen having an amino acid sequence encoded by a nucleotide sequence recited in SEQ ID NO:1–SEQ ID NO:22, or a variant of said antigen that differs only in conservative substitutions and/or modifications; (b) contacting the biological sample with one or more additional polypeptides comprising one or more epitopes of other *T. cruzi* antigens, or a variant thereof that differs only in conservative substitutions and/or modifications; and (c) detecting in the biological sample the presence of antibodies that bind to one or more of said polypeptides, therefrom detecting *T. cruzi* infection in the biological sample. In one embodiment, the additional polypeptide comprises an epitope of TcD, or a variant thereof that differs only in conservative substitutions and/or modifications. In another embodiment, the additional polypeptides comprise an epitope of TcD (or a variant thereof that differs only in conservative substitutions and/or modifications) and an epitope of TcE (or a variant thereof that differs only in conservative substitutions and/or modifications). In yet another embodiment, the additional polypeptides comprise an epitope of TcD (or a variant thereof that differs only in conservative substitutions and/or modifications) and PEP-2 (or a variant thereof that differs only in conservative substitutions and/or modifications).

In yet further aspects, the present invention provides combination polypeptides comprising two or more polypeptides, each polypeptide comprising an epitope of a *T. cruzi* antigen having an amino acid sequence encoded by a nucleotide sequence recited in SEQ ID NO:1–SEQ ID NO:22, or a variant thereof that differs only in conservative substitutions and/or modifications. Combination polypeptides comprising at least one epitope of a *T. cruzi* antigen having an amino acid sequence encoded by a nucleotide sequence recited in SEQ ID NO:1–SEQ ID NO:22, or a variant thereof that differs only in conservative substitutions and/or modifications, and at least one epitope selected from the group consisting of TcD epitopes, TcE epitopes, PEP-2 epitopes and variants thereof that differ only in conservative substitutions and/or modifications are also provided. In specific embodiments, combination polypeptides comprising an amino acid sequence of SEQ ID NO:82 or 95 are provided. Such combination polypeptides may be prepared either by synthetic means or using recombinant DNA technology.

In related aspects, methods are provided for detecting *T. cruzi* infection in a biological sample, comprising (a) contacting the biological sample with at least one of the above combination polypeptides and (b) detecting in the biological sample the presence of antibodies that bind to the combination polypeptide.

These and other aspects of the present invention will become apparent upon reference to the following detailed description and attached drawings. All references disclosed herein are hereby incorporated by reference in their entirety as if each was incorporated individually.

DETAILED DESCRIPTION OF THE INVENTION

Figure 1:
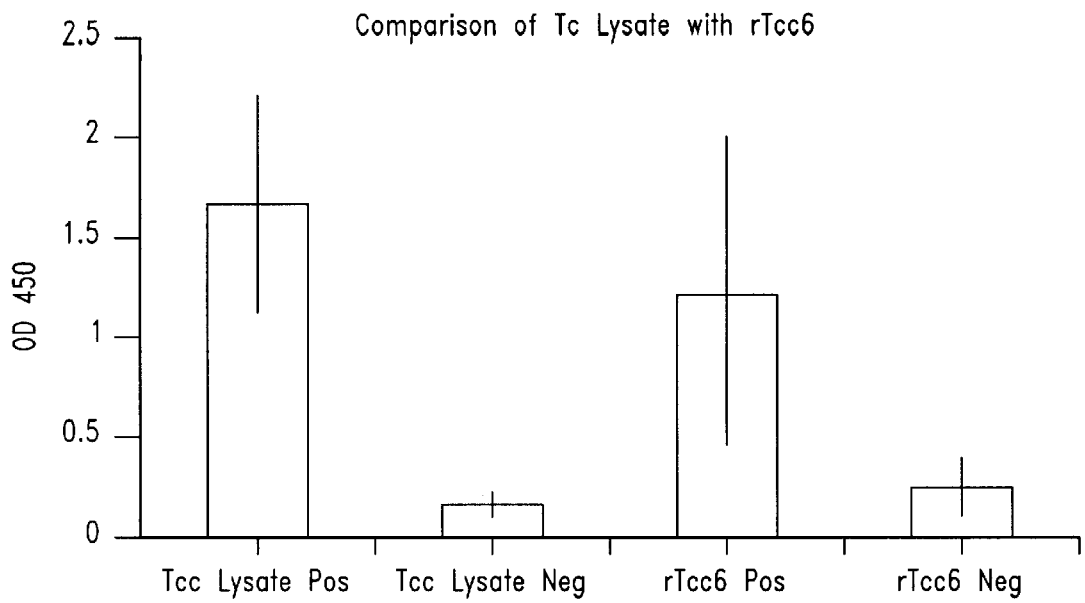
FIG. 1 is a graph comparing the reactivity of *T. cruzi* lysate and a representative polypeptide of the present invention (rTcc6) in an ELISA assay performed using sera from *T. cruzi*-infected (Pos) and uninfected (Neg) individuals. The bars represent±1 standard deviation.

As noted above, the present invention is generally directed to compounds and methods for detecting and protecting against *T. cruzi* infection in individuals and in blood supplies. The compounds of this invention generally comprise one or more epitopes of *T. cruzi* antigens. In particular, polypeptides comprising an epitope of a *T. cruzi* antigen having an amino acid sequence encoded by a nucleotide sequence recited in SEQ ID NO:1–SEQ ID NO:22 are preferred. As used herein, the term "polypeptide" encompasses amino acid chains of any length, including full length (i.e., native) antigens. Thus, a polypeptide comprising an epitope may consist entirely of the epitope or may contain additional sequences. The additional sequences may be derived from the native antigen or may be heterologous, and such sequences may (but need not) be antigenic. A protein "having" a particular amino acid sequence is a protein that contains, within its full length sequence, the recited sequence. Such a protein may, or may not, contain additional amino acid sequence. The use of one or more epitopes from additional *T. cruzi* proteins, prior to or in combination with one or more epitopes of sequences recited herein, to enhance the sensitivity and specificity of the diagnosis, is also contemplated.

An "epitope," as used herein, is a portion of a *T. cruzi* antigen that reacts with sera from *T. cruzi*-infected individuals (i.e., an epitope is specifically bound by one or more antibodies within such sera). Epitopes of the antigens described in the present application may generally be identified using methods known to those of ordinary skill in the art, such as those summarized in Paul, Fundamental Immunology, 3rd ed., 243–247 (Raven Press, 1993) and references cited therein. For example, a polypeptide derived from a native *T. cruzi* antigen may be screened for the ability to react with pooled sera obtained from *T. cruzi*-infected patients. Suitable assays for evaluating reactivity with *T. cruzi*-infected sera, such as an enzyme linked immunosorbent assay (ELISA), are described in more detail below, and in Harlow and Lane, *Antibodies: A Laboratory Manual*, Cold Spring Harbor Laboratory, 1988. An epitope of a polypeptide is a portion that reacts with such antisera at a level that is substantially similar to the reactivity of the full length polypeptide. In other words, an epitope may generate at least about 80%, and preferably at least about 100%, of the response generated by the full length polypeptide in an antibody binding assay (e.g., an ELISA).

The compounds and methods of this invention also encompass variants of the above polypeptides. A polypeptide "variant," as used herein, is a polypeptide that differs from the recited polypeptide only in conservative substitutions and/or modifications, such that the antigenic properties of the polypeptide are retained. In a preferred embodiment, variant polypeptides differ from an identified sequence by substitution, deletion or addition of five amino acids or fewer. Such variants may generally be identified by modifying one of the above polypeptide sequences, and evaluating the antigenic properties of the modified polypeptide using, for example, the representative procedures described herein. Polypeptide variants preferably exhibit at least about 70%, more preferably at least about 90% and most preferably at least about 95% identity (determined as described below) to the identified polypeptides.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA*, 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity (determined as described below) to the recited sequence.

The polypeptides provided by the present invention include variants that are encoded by DNA sequences which are substantially homologous to one or more of the DNA sequences specifically recited herein. "Substantial homology," as used herein, refers to DNA sequences that are capable of hybridizing under moderately stringent conditions. Suitable moderately stringent conditions include pre-washing in a solution of 5×SSC, 0.5% SDS, 1.0 mM EDTA (pH 8.0); hybridizing at 50° C.–65° C., 5×SSC, overnight or, in the event of cross-species homology, at 45° C. with 0.5×SSC; followed by washing twice at 65° C. for 20 minutes with each of 2×, 0.5× and 0.2× SSC containing 0.1% SDS. Such hybridizing DNA sequences are also within the scope of this invention, as are nucleotide sequences that, due to code degeneracy, encode an immunogenic polypeptide that is encoded by a hybridizing DNA sequence.

Two nucleotide or polypeptide sequences are said to be "identical" if the sequence of nucleotides or amino acid residues in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M.O. (1978) A model of evolutionary change in proteins—Matrices for detecting distant relationships. In Dayhoff, M.O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) Fast and sensitive multiple sequence alignments on a microcomputer CABIOS 5:151–153; Myers, E. W. and Muller W. (1988) Optimal alignments in linear space CABIOS 4:11–17; Robinson, E. D. (1971) *Comb. Theor* 11:105; Santou, N. Nes, M. (1987). The neighbor joining method. A new method for reconstructing phylogenetic trees *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif. ; Wilbur, W. J. and Lipman, D. J. (1983) Rapid similarity searches of nucleic acid and protein data banks *Proc. Natl. Acad, Sci. USA* 80:726–730.

Preferably, the "percentage of sequence identity" is determined by comparing two optimally aligned sequences over a window of comparison of at least 20 positions, wherein the portion of the polynucleotide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

In a related aspect, combination polypeptides comprising epitopes of multiple *T. cruzi* antigens are disclosed. A "combination polypeptide" is a polypeptide in which epitopes of different *T. cruzi* antigens, or variants thereof, are joined, for example through a peptide linkage, into a single amino acid chain. The amino acid chain thus formed may be either linear or branched. The epitopes may be joined directly (i.e., with no intervening amino acids) or may be joined by way of a linker sequence (e.g., Gly-Cys-Gly) that does not significantly alter the antigenic properties of the epitopes. The peptide epitopes may also be linked through non-peptide linkages, such as hetero- or homo-bifunctional agents that chemically or photochemically couple between specific functional groups on the peptide epitopes such as through amino, carboxyl, or sulthydryl groups. Bifunctional agents which may be usefully employed in the combination polypeptides of the present invention are well known to those of skill in the art. Epitopes may also be linked by means of a complementary ligand/anti-ligand pair, such as avidin/biotin, with one or more epitopes being linked to a first member of the ligand/anti-ligand pair and then being bound to the complementary member of the ligand/anti-ligand pair either in solution or in solid phase. A combination polypeptide may contain multiple epitopes of polypeptides as described herein and/or may contain epitopes of one or more other *T. cruzi* antigens, such as TcD, TcE or PEP-2, linked to an epitope described herein.

In general, *T. cruzi* antigens, and DNA sequences encoding such antigens, may be prepared using any of a variety of procedures. For example, a *T. cruzi* cDNA or genomic DNA expression library may be screened with pools of sera from *T. cruzi*-infected individuals. Such screens may generally be performed using techniques well known to those of ordinary skill in the art, such as those described in Sambrook et al., *Molecular Cloning: A Laboratory Manual*, Cold Spring Harbor Laboratories, Cold Spring Harbor, N.Y., 1989. Briefly, the bacteriophage library may be plated and transferred to filters. The filters may then be incubated with serum and a detection reagent. In the context of this invention, a "detection reagent" is any compound capable of binding to the antibody-antigen complex, which may then be detected by any of a variety of means known to those of ordinary skill in the art. Typical detection reagents for screening purposes contain a "binding agent," such as Protein A, Protein G, IgG or a lectin, coupled to a reporter group. Preferred reporter groups include, but are not limited to, enzymes, substrates, cofactors, inhibitors, dyes, radionuclides, luminescent groups, fluorescent groups and biotin. More preferably, the reporter group is horseradish peroxidase, which may be detected by incubation with a substrate such as tetramethylbenzidine or 2,2'-azino-di-3-ethylbenzthiazoline sulfonic acid. Plaques containing cDNAs that express a protein that binds to an antibody in the serum may be isolated and purified by techniques known to those of ordinary skill in the art. Appropriate methods may be found, for example, in Sambrook et al., *Molecular Cloning: A Laboratory Manual*, Cold Spring Harbor Laboratories, Cold Spring Harbor, N.Y., 1989.

DNA molecules having the nucleotide sequences recited in SEQ ID NO:1–SEQ ID NO:18 may be isolated by screening a *T. cruzi* genomic expression library with pools of sera from *T. cruzi*-infected individuals, as described above. More specifically, DNA molecules having the nucleotide sequences recited in SEQ ID NO:1–SEQ ID NO:16 may be isolated by screening the library with a pool of sera that displays serological reactivity (in an ELISA or Western assay) with parasite lysate and/or one or both of the *T. cruzi* antigens TcD and TcE, described in U.S. Pat. No. 5,304,371 and U.S. Ser. No. 08/403,379, filed Mar. 14, 1995. A subsequent screen is then performed with patient sera lacking detectable anti-TcD antibody. A DNA molecule having the nucleotide sequences recited in SEQ ID NO:17 (5' end) and SEQ ID NO:18 (3' end) may be isolated by screening the genomic expression library with a pool of sera that displays lower serological reactivity (i.e., detects a signal less than 3 standard deviations over background reactivity in an ELISA or Western assay) with lysate, TcD and TcE, followed by a subsequent screen with patient sera lacking detectable anti-TcD antibody.

DNA molecules having the sequences recited in SEQ ID NO:19–SEQ ID NO:22 may be obtained by screening an unamplified *T. cruzi* cDNA expression library with sera (both higher and lower serological reactivity) from *T. cruzi*-infected individuals, as described above.

Alternatively, DNA molecules having the sequences recited in SEQ ID NO:1–SEQ ID NO:22 may be amplified from *T. cruzi* genomic DNA or cDNA via polymerase chain reaction. For this approach, sequence-specific primers may be designed based on the sequences provided in SEQ ID NO:1–SEQ ID NO:22, and may be purchased or synthesized. An amplified portion of the DNA sequences may then be used to isolate the full length genomic or cDNA clones using well known techniques, such as those described in Sambrook et al., *Molecular Cloning: A Laboratory Manual*, Cold Spring Harbor Laboratories, Cold Spring Harbor, N.Y. (1989).

Epitopes of antigens having amino acid sequences encoded by the above DNA sequences may generally be identified by generating polypeptides containing portions of the native antigen and evaluating the reactivity of the polypeptides with sera from *T. cruzi*-infected individuals, as described above. In many instances, peptides comprising one or more repeat sequences found in the native antigen contain an epitope. Such repeat sequences may be identified based on inspection of the above nucleotide sequences. Representative repeat sequences for antigens encoded by the above DNA sequences are provided in SEQ ID NO:23–SEQ ID NO:36 and SEQ ID NO:47–SEQ ID NO:49. More specifically, repeat sequences for the sequence recited in SEQ ID NO:3 are provided in SEQ ID NO:23 (Frame 1), SEQ ID NO:24 (Frame 2) and SEQ ID NO:25 (Frame 3). Repeat sequences for the sequence recited in SEQ ID NO:4 are provided in SEQ ID NO:26 (Frame 1) and SEQ ID NO:27 (Frame 3) and repeat sequences for SEQ ID NO:9 are provided in SEQ ID NO:47 (Frame 1), SEQ ID NO:48 (Frame 2) and SEQ ID NO:49 (Frame 3). For SEQ ID NO:12, repeat sequences are provided in SEQ ID NO:28 (Frame 1), SEQ ID NO:29 (Frame 2) and SEQ ID NO:30 (Frame 3). SEQ ID NO:31 recites a repeat sequence for SEQ ID NO:15. For SEQ ID NO:16, repeat sequences are provided in SEQ ID NO:32 (Frame 2) and SEQ ID NO:33 (Frame 3). Finally, repeat sequences for SEQ ID NO:18 are provided in SEQ ID NO:34 (Frame 1), SEQ ID NO:35 (Frame 2) and SEQ ID NO:36 (Frame 3).

The polypeptides described herein may be generated using techniques well known to those of ordinary skill in the art. Polypeptides having fewer than about 100 amino acids, and generally fewer than about 50 amino acids, can be synthesized using, for example, the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied Biosystems Division, Foster City, Calif. Thus, for example, polypeptides comprising the above repeat sequences or portions thereof, may be synthesized by this method. Similarly, epitopes of other native antigens, or variants thereof, may be prepared using an automated synthesizer.

Alternatively, the polypeptides of this invention may be prepared by expression of recombinant DNA encoding the polypeptide in cultured host cells. Preferably, the host cells are *E. coli*, yeast, an insect cell line (such as Spodoptera or Trichoplusia) or a mammalian cell line, including (but not limited to) CHO, COS and NS-1. The DNA sequences expressed in this manner may encode naturally occurring proteins, such as full length antigens having the amino acid sequences encoded by the DNA sequences of SEQ ID NO:1–SEQ ID NO:22, portions of naturally occurring proteins, or variants of such proteins. Representative polypeptides encoded by such DNA sequences are provided in SEQ ID NO:37–SEQ ID NO:46, SEQ ID NO:52, and SEQ ID NO:65.

Expressed polypeptides of this invention are generally isolated in substantially pure form. Preferably, the polypeptides are isolated to a purity of at least 80% by weight, more preferably, to a purity of at least 95% by weight, and most preferably to a purity of at least 99% by weight. In general, such purification may be achieved using, for example, the standard techniques of ammonium sulfate fractionation, SDS-PAGE electrophoresis, and affinity chromatography.

In another aspect of this invention, methods for detecting *T. cruzi* infection in individuals and blood supplies are disclosed. In one embodiment, *T. cruzi* infection may be detected in any biological sample that contains antibodies. Preferably, the sample is blood, serum, plasma, saliva, cerebrospinal fluid or urine. More preferably, the sample is a blood or serum sample obtained from a patient or a blood supply. Briefly, *T. cruzi* infection may be detected using any one or more of the polypeptides described above, or variants thereof, to determine the presence or absence of antibodies to the polypeptide or polypeptides in the sample, relative to a predetermined cut-off value.

There are a variety of assay formats known to those of ordinary skill in the art for using purified antigen to detect antibodies in a sample. See, e.g., Harlow and Lane, *Antibodies: A Laboratory Manual*, Cold Spring Harbor Laboratory, 1988. In a preferred embodiment, the assay involves the use of polypeptide immobilized on a solid support to bind to and remove the antibody from the sample. The bound antibody may then be detected using a detection reagent that binds to the antibody/peptide complex and contains a detectable reporter group. Suitable detection reagents include antibodies that bind to the antibody/polypeptide complex and free polypeptide labeled with a reporter group (e.g., in a semi-competitive assay).

Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptide may be bound to the solid support using a variety of techniques known to those in the art, which are amply described in the patent and scientific literature. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 $\mu$g, and preferably about 100 ng, is sufficient to bind an adequate amount of antigen. Nitrocellulose will bind approximately 100 $\mu$g of protein per cm$^3$.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook (1991) at A12–A13).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

Once the polypeptide is immobilized on the support, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized polypeptide is then incubated with the sample, and antibody (if present in the sample) is allowed to bind to the antigen. The sample may be diluted with a suitable diluent, such as phosphate-buffered saline (PBS) prior to incubation. In general, an appropriate contact time (i.e., incubation time) is that period of time that is sufficient to permit detect the presence of *T. cruzi* antibody within a *T. cruzi*-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art. Common binding agents may also be purchased conjugated to a variety of reporter groups from many sources (e.g., Zymed Laboratories, San Francisco, Calif. and Pierce, Rockford, Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of *T. cruzi* antibodies in the sample, the signal detected from the reporter group that remains bound to the solid support is generally compared to a signal that corresponds to a predetermined cut-off value. This cut-off value is preferably the average mean signal obtained when the immobilized antigen is incubated with samples from an uninfected patient. In general, a sample generating a signal that is three standard deviations above the mean is considered positive for *T. cruzi* antibodies and *T. cruzi* infection. In an alternate preferred embodiment, the cut-off value is determined using a Receiver Operator Curve, according to the method of Sackett et al., *Clinical Epidemiology: A Basic Science for Clinical Medicine*, p. 106–7 (Little Brown and Co., 1985). Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive.

Alternatively, the cut-off value may be shifted to the left along the plot, to minimize the false positive rate, or to the right, to minimize the false negative rate. In general, a sample generating a signal that is higher than the cut-off value determined by this method is considered positive for *T. cruzi* infection.

In a related embodiment, the assay is performed in a flow-through or strip test format, wherein the antigen is immobilized on a membrane such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of *T. cruzi* antibodies in the sample. Such tests can typically be performed with a very small amount (e.g., one drop) of patient serum or blood.

The assays discussed above may be performed using one or more of the polypeptides described herein. Alternatively, the sensitivity may be improved by using epitopes of one or more additional T. cruzi antigens in combination with the above polypeptide(s). In particular, epitopes of TcD (disclosed, for example, in U.S. Pat. No. 5,304,371), PEP-2 and/or TcE (both of which are disclosed, for example, in U.S. Ser. No. 08/403,379, filed Mar. 14, 1995) may be used in conjunction with the above polypeptide(s). The PEP-2 antigenic epitope is also discussed in Peralta et al., *J Clin. Microbiol.* 32:971–74, 1994. The sequence of TcD is provided in SEQ ID NO:50, the sequence of TcE is provided in SEQ ID NO:51. The TcD antigenic epitope preferably has the amino acid sequence Ala Glu Pro Lys Ser Ala Glu Pro Lys Pro Ala Glu Pro Lys Ser (SEQ ID NO:53) or the amino acid sequence Ala Glu Pro Lys Pro Ala Glu Pro Lys Ser Ala Glu Pro Lys Pro (SEQ ID NO:54). The TcE epitope preferably has the amino acid sequence Lys Ala Ala Ile Ala Pro Ala Lys Ala Ala Ala Ala Pro Ala Lys Ala Ala Thr Ala Pro Ala (SEQ ID NO:55) or the amino acid sequence Lys Ala Ala Ala Ala Pro Ala Lys Ala Ala Ala Ala Pro Ala Lys Ala Ala Ala Ala Pro Ala (SEQ ID NO:56), and the PEP2 epitope preferably has the amino acid sequence Gly Asp Lys Pro Ser Pro Phe Gly Gln Ala Ala Ala Gly Asp Lys Pro Ser Pro Phe Gly Gln Ala (SEQ ID NO:57).

Additional epitopes may be present within the same polypeptide (i.e., in a combination polypeptide) or may be included in separate polypeptides. Combination polypeptides may be prepared either synthetically, as described below in Example 2, or using recombinant DNA technology as detailed below in Example 7. Preferably, the polypeptides are immobilized by adsorption on a solid support such as a well of a microtiter plate or a membrane, as described above, such that a roughly similar amount of each polypeptide contacts the support, and such that the total amount of polypeptide in contact with the support ranges from about 1 ng to about 10 µg. The remainder of the steps may generally be performed as described above.

The polypeptides described above may also be used following diagnosis using one or more of the epitopes from TcD, TcE and/or PEP2. In this embodiment, the polypeptides of the present invention are used to confirm a diagnosis of T. cruzi infection based on a screen with TcD, TcE and/or PEP2. Diagnosis of T. cruzi infection using epitopes from TcD, TcE and/or PEP2 is described in U.S. Ser. No. 08/403,379, filed Mar. 14, 1995.

In yet another aspect of this invention, methods are provided for detecting *T. cruzi* in a biological sample using monospecific antibodies (which may be polyclonal or monoclonal) to one or more epitopes, as described above. Antibodies to purified or synthesized polypeptides may be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared,. for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction.

Monospecific antibodies to epitopes of one or more of the polypeptides described herein may be used to detect *T. cruzi* infection in a biological sample using any of a variety of immunoassays, which may be direct or competitive. Suitable biological samples for use in this aspect of the present invention are as described above. Briefly, in one direct assay format, a monospecific antibody may be immobilized on a solid support (as described above) and contacted with the sample to be tested. After removal of the unbound sample, a second monospecific antibody, which has been labeled with a reporter group, may be added and used to detect bound antigen. In an exemplary competitive assay, the sample may be combined with the monoclonal or polyclonal antibody, which has been labeled with a suitable reporter group. The mixture of sample and antibody may then be combined with polypeptide antigen immobilized on a suitable solid support. Antibody that has not bound to an antigen in the sample is allowed to bind to the immobilized antigen, and the remainder of the sample and antibody is removed. The level of antibody bound to the solid support is inversely related to the level of antigen in the sample. Thus, a lower level of antibody bound to the solid support indicates the presence of *T. cruzi* in the sample. To determine the presence or absence of *T. cruzi* infection, the signal detected from the reporter group that remains bound to the solid support is generally compared to a signal that corresponds to a predetermined cut-off value. Such cut-off values may generally be determined as described above. Any of the reporter groups discussed above in the context of ELISAs may be used to label the monospecific antibodies, and binding may be detected by any of a variety of techniques appropriate for the reporter group employed. Other formats for using monospecific antibodies to detect *T. cruzi* in a sample will be apparent to those of ordinary skill in the art, and the above formats is provided solely for exemplary purposes.

In another aspect of this invention, vaccines and pharmaceutical compositions are provided for the prevention of *T. cruzi* infection, and complications thereof, in a mammal. The pharmaceutical compositions generally comprise one or more polypeptides, containing one or more epitopes of *T. cruzi* proteins, and a physiologically acceptable carrier. The vaccines comprise one or more of the above polypeptides and an adjuvant, for enhancement of the immune response.

Routes and frequency of administration and polypeptide doses will vary from individual to individual and may parallel those currently being used in immunization against other protozoan infections. In general, the pharmaceutical compositions and vaccines may be administered by injection (e.g., intramuscular, intravenous or subcutaneous), intranasally (e.g., by aspiration) or orally. Between 1 and 4 doses may be administered for a 2–6 week period. Preferably, two doses are administered, with the second dose 2–4 weeks later than the first. A suitable dose is an amount of polypeptide that is effective to raise antibodies in a treated mammal that are sufficient to protect the mammal from *T. cruzi* infection for a period of time. In general, the amount of polypeptide present in a dose ranges from about 1 pg to about 100 mg per kg of host, typically from about 10 pg to about 1 mg, and preferably from about 100 pg to about 1 $\mu$g. Suitable dose sizes will vary with the size of the animal, but will typically range from about 0.01 mL to about 5 mL for 10–60 kg animal.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune response, such as lipid A, *Bordella pertussis* or *Mycobacterium tuberculosis*. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

The following Examples are offered by way of illustration and not by way of limitation.

EXAMPLES

Example 1

A. Preparation of DNA Encoding *T. cruzi* Antigens

This Example illustrates the preparation of genomic and cDNA olecules encoding *T. cruzi* Antigens.
Preparation of Genomic Clones A genomic expression library was constructed from randomly sheared *T. cruzi* genomic DNA (Tulahuen C2 strain) using the Lambda ZAP expression system (Stratagene, La Jolla, Calif.) according to the manufacturer's instructions. In one screen, the library was screened with a pool of sera from five patients that displayed high reactivity with parasite lysate and/or one or both of the *T. cruzi* antigens TcD and TcE, described in U.S. Pat. No. 5,304,371 and U.S. Ser. No. 08/403,379, filed Mar. 14, 1995. Each of the five patients' sera was determined to be reactive based on Western and ELISA assays with whole lysate and/or TcD or TcE. Anti-*E. coli* reactivity was removed from the serum prior to screening by adsorption. 50,000 pfu of the unamplified library was screened with the serum pool and plaques expressing proteins that reacted with the serum were detected using protein A-horseradish peroxidase (with the ABTS substrate). A subsequent screen was then performed with a pool of sera from three patients lacking detectable anti-TcD antibody in Western and ELISA assays using recombinant TcD.

A similar screen was performed using a pool of sera that displayed low reactivity with lysate, TcD and TcE (i.e., detected a signal less than 3 standard deviations over background reactivity in an ELISA or Western assay), followed by a subsequent screen with patient sera lacking detectable anti-TcD antibody, as described above.

Twenty-eight clones that expressed proteins which reacted with both pools of sera in at least one of the above screens were then isolated. Excision of the pBSK(−) phagemid (Stratagene, Inc., La Jolla, Calif.) was carried out according to the manufacturer's protocol. Overlapping clones were generated by exonuclease III digestion and single-stranded templates were isolated after infection with VCSM 13 helper phage. The DNA was sequenced by the dideoxy chain termination method or by the Taq di-terminator system, using an Applied Biosystem automated sequencer, Model 373A.

Of the 28 clones, five had been reported previously, two were identical, and eight contained identical peptide sequences represented by a degenerate 42 base pair repeat. SEQ ID NO:16 shows the prototype clone containing the 42 base pair repeat sequence. Accordingly, 14 novel DNA sequences encoding *T. cruzi* antigens were prepared using the above screen with the reactive pool of sera (shown in SEQ ID NO:1–SEQ ID NO:16, where SEQ ID NO:4 and SEQ ID NO:5 represent the 5' and 3' ends, respectively, of a single clone, SEQ ID NO:9 and SEQ ID NO:10 represent the 5' and 3' ends, respectively, of a single clone. One novel sequence was obtained with the screen employing the sera with low reactivity (shown in SEQ ID NO:17 (5' end) and SEQ ID NO:18 (3' end)).

B. Preparation of cDNA Clones

Poly A+RNA was purified from the intracellular amastigote stage of *T. cruzi* (Tulahuen C2 strain). The RNA was reverse transcribed and used in the construction of a unidirectional cDNA expression library in the Lambda UniZap expression vector (Stratagene, La Jolla, Calif.) according to the manufacturer's instructions. 50,000 pfu of the unamplified library was screened with a serum pool containing patient sera that displayed both high and low serological reactivity, followed by a subsequent screen with patient sera lacking detectable anti-TcD antibody, as described above. A total of 32 clones were isolated from this screen. Twenty-five of these clones were proteins of the translational apparatus that have been previously identified as highly immunogenic, and all were different from the clones identified by screening the genomic expression library. The remaining seven are represented by the sequences provided in SEQ ID NO:19–SEQ ID NO:22. The sequence recited in SEQ ID NO:22 is that of *T. cruzi* ubiquitin.

Example 2

Synthesis of Synthetic Polyeptides

This Example illustrates the synthesis of polypeptides having sequences derived from *T. cruzi* antigens described herein.

Polypeptides may be synthesized on a Millipore 9050 peptide synthesizer using FMOC chemistry with HBTU (O-benzotriazole-N,N,N', N'-tetramethyuronium hexafluorophosphate) activation. A gly-cys-gly sequence may be attached to the amino or carboxyl terminus of the peptide to provide a method of conjugation or labeling of the peptide. Cleavage of the peptides from the solid support may be carried out using the following cleavage mixture: trifluoroacetic acid:ethanediol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1%TFA) may be used to elute the peptides. Following lyophilization of the pure fractions, the peptides are characterized using electrospray mass spectrometry and by amino acid analysis.

This procedure was used to synthesize peptides such as Tcc22-1, Tcc22-1+, Tcc22-2.1 (contained within SEQ ID NO:41), TcLo1.1,1.2 and 1.3 (contained within SEQ ID NO:34, 35 and 36) and TcHi10.1 and 10.3 (SEQ ID NO:26 and 27) which have the following sequences:

```
Tcc22-1                            VRASNCRKKACGHCSNLRMKKK

Tcc22-1+         EALAKKYNWEKKVCRRCYARLPVRASNCRKKACGHCSNLRMKKK

Tcc22-2.1  VLRLRGGVMEPTLEALAKKYNWEKKVCRRCYARL

TcLo1.1    GYVRGRKQRWQLHACGYVRGRKQRRQLHACGYVRGRKQRWQLHAF

TcLo1.2    GTSEEGSRGGSSMPSGTSEEGSRGGSSMPA

TcLo1.3    VRPRKEAEVAAPCLRVRPRKEAEEAAPCLR

TcHi10.1   SVPGKRLRNSHGKSLRNVHGKRPKNEHGKRLRSVPNERLR

TcHi10.3   EAEELARQESEERARQEAEERAWQEAEERAQREAEERAQR
```

Example 3

Serological Reactivity of *T. cruzi* Recombinant Antigens

This example illustrates the diagnostic properties of several recombinant antigens found to be serologically active. This includes studies of reactivity with *T. cruzi* positive and negative sera as well as cross reactivity studies with sera from patients with other diseases.

Assays were performed in 96 well plates (Coming Easiwash, Coming, N.Y.). Wells were coated in 50 μl of carbonate coating buffer pH 9.6. For *T. cruzi* lysate, 100 ng/well was used, and for each of the recombinant antigens 200 ng/well was used. The wells were coated overnight at 4° C. (or 2 hours at 37° C.). The plate contents were then removed and wells were blocked for 2 hours with 200 μl of PBS/1%BSA. After the blocking step, the wells were washed five times with PBS/0.1% Tween 20™. 50 μl of sera (either positive or negative for *T. cruzi* infection), diluted 1:50 in PBS/0.1% Tween 20/0.1%BSA was then added to each well and incubated for 30 minutes at room temperature. The plates were then washed again five times with PBS/0.1% Tween 20™.

The enzyme conjugate (horse radish peroxidase-Protein A, Zymed, San Francisco, Calif.) was then diluted 1:20,000 in PBS/0.1% Tween 20™/0.1%BSA, and 50 μl of the diluted conjugate was added to each well and incubated for 30 minutes at room temperature. Following incubation the wells were again washed five times with PBS/0.1% Tween 20™. 100 μl of the peroxidase substrate, tetramethylbenzidine (Kirkegaard and Perry Laboratories, Gaithersburg, Md.) was added, undiluted, to each of the wells and incubated for 15 minutes. The reaction was stopped by the addition of 100 μl of 1N $H_2SO_4$ to each well, and the plates were read at 450 nm.

Figure 2:
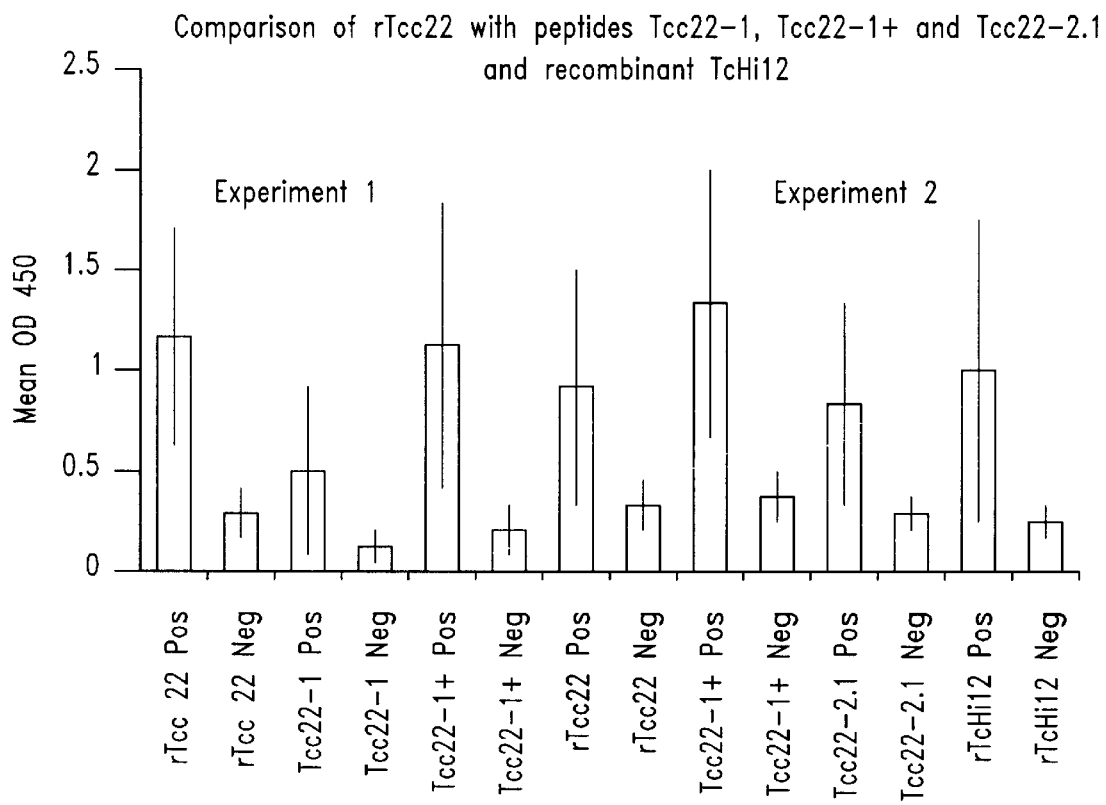
FIG. 2 is a graph presenting a comparison of the reactivity of representative polypeptides of the subject invention in an ELISA assay performed using sera from *T. cruzi*-infected (Pos) and uninfected (Neg) individuals. Experiment 1 shows a comparison of rTcc22 and the peptides Tcc22-1 and Tcc22-1+; Experiment 2 shows a comparison of rTcc22, rTcHi12 and the peptides Tcc22-1, Tcc22-1+ and Tcc22-2.1. The bars represent±1 standard deviation.
Figure 3:
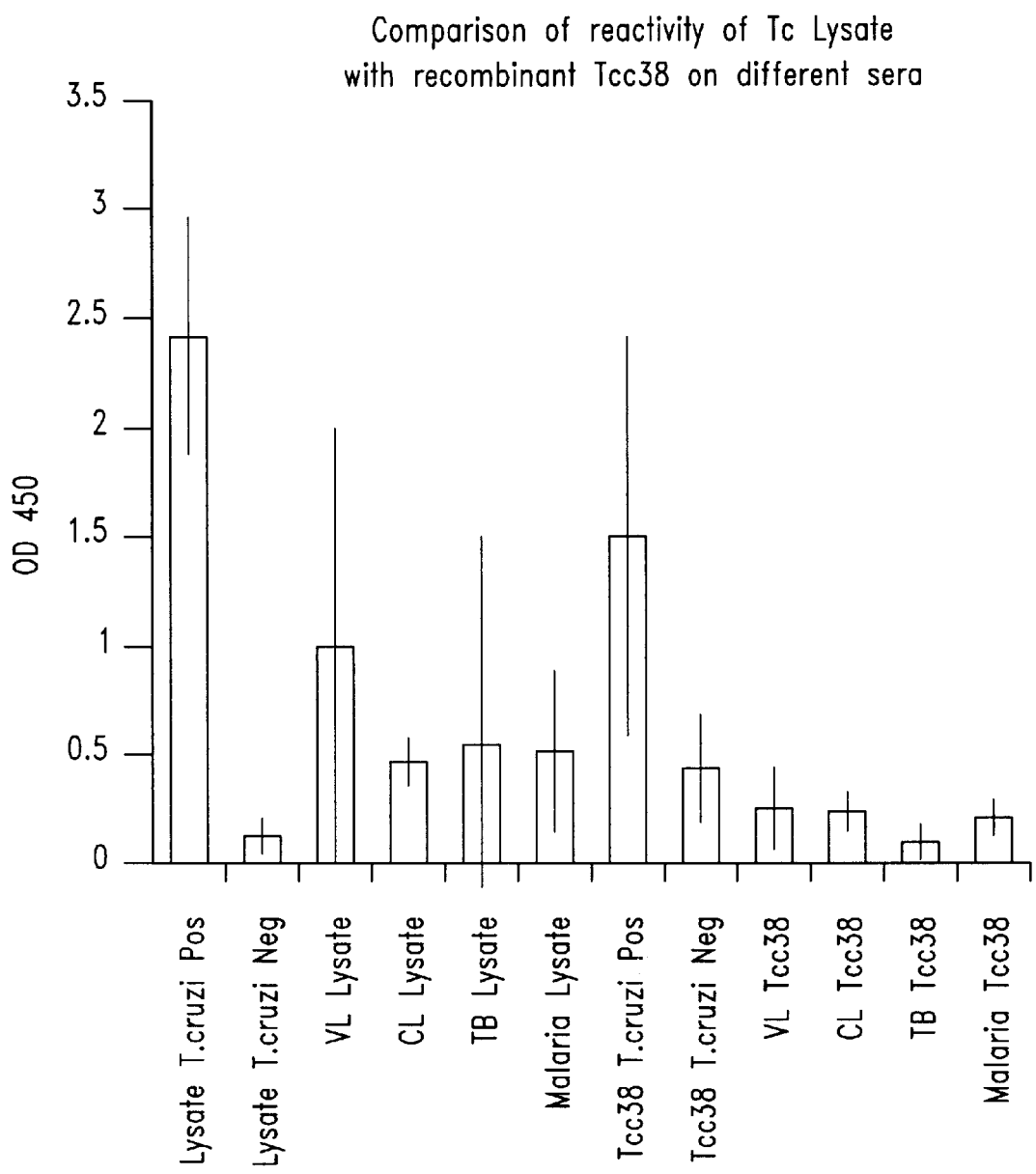
FIG. 3 is a graph depicting a comparison of the reactivity of *T. cruzi* lysate and a representative polypeptide (Tcc38) in an ELISA assay performed using sera from *T. cruzi*-infected (Pos) and uninfected (Neg) individuals, as well as using sera from individuals with visceral leishmaniasis (VL), cutaneous leishmaniasis (CL), tuberculosis (TB) and malaria. The bars represent±1 standard deviation.

FIG. 1 shows the reactivity of the recombinant rTcc6 (SEQ ID NO:39) as compared to that of *T. cruzi* lysate. Based on a cutoff of the mean of the negatives plus 3 standard deviations, 49 out of 50 serum samples were positive with lysate, and 34 out of 50 were positive with rTcc6. In a similar study (shown in FIG. 2), the recombinant rTcc22 (SEQ ID NO:41) was found to have a sensitivity of 79.2% (38 out of 48 serum samples were positive). Comparative studies of the recombinant rTcc38 (SEQ ID NO:38) with *T. cruzi* lysate using similar criteria showed that 24/39 were positive compared with 39/39 for lysate (FIG. 3). Tcc38 when tested with potentially cross reacting sera showed improved specificity over *T. cruzi* lysate.

The recombinant TcHi12 (SEQ ID NO:37) was also found to be immunoreactive (FIG. 2) having a sensitivity of 62.5% (15/24).

Example 4

Serological Reactivity of *T. cruzi* Synthetic Peptide Antigens

This example illustrates the diagnostic properties of several of the peptides described in Example 2. These peptides were tested for reactivity with *T. cruzi* positive and negative sera and, in some cases, for cross reactivity with sera from patients with other, potentially cross reactive, diseases.

Figure 4:
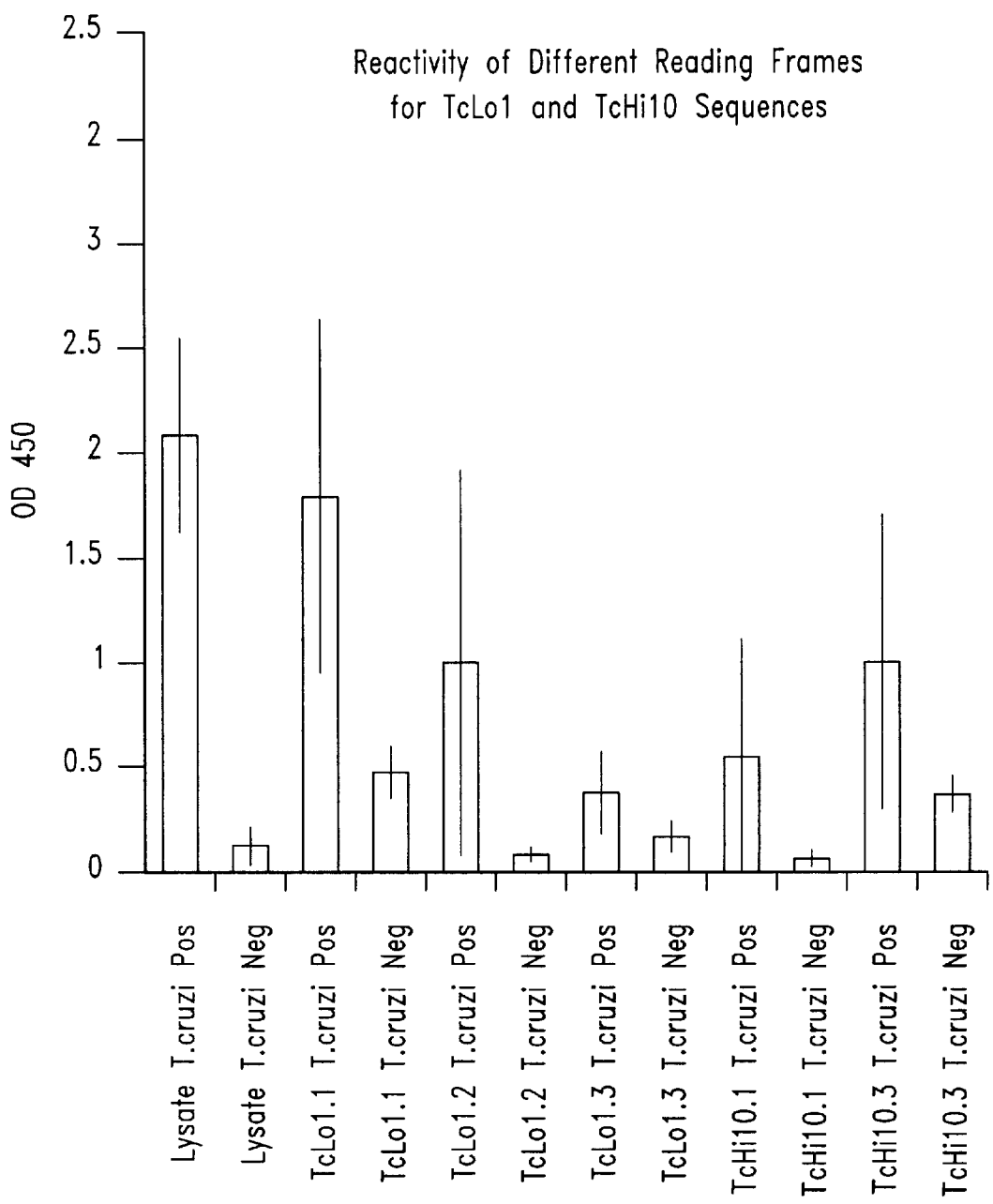
FIG. 4 is a graph presenting a comparison of the reactivity of *T. cruzi* lysate and several polypeptides of the present invention, representing different reading frames of the TcLo1 and TcHi10 antigens, in an ELISA assay performed using sera from *T. cruzi*-infected (Pos) and uninfected (Neg) individuals. The bars represent±1 standard deviation.
Figure 5:
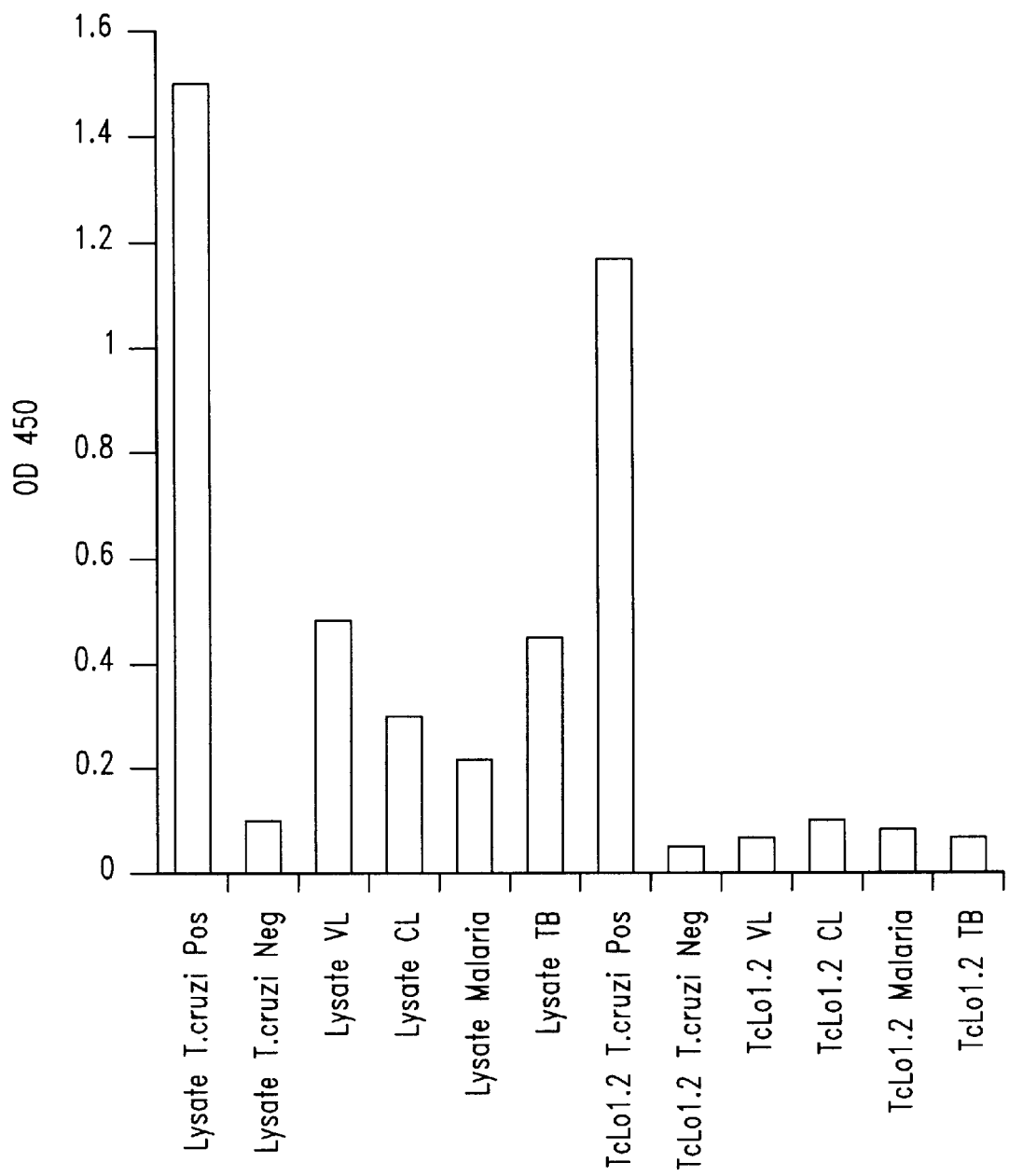
FIG. 5 is a graph comparing the reactivity of *T. cruzi* lysate and a representative polypeptide (TccLo1.2) in an ELISA assay performed using sera from *T. cruzi*-infected (Pos) and uninfected (Neg) individuals, as well as sera from individuals with visceral leishmaniasis (VL), cutaneous leishmaniasis (CL), malaria and tuberculosis (TB).

The first group of peptides included different reading frames to determine the most reactive repeat sequence. The peptides tested were TcLo1.1 (contained within SEQ ID NO:34), TcLo1.2 (contained within SEQ ID NO:35) and TcLo1.3 (contained within SEQ ID NO:36), representing reading frames 1, 2 and 3 of the DNA sequence provided in SEQ ID NO:18, and TcHi10.1 (SEQ ID NO:26) and TcHi10.3 (SEQ ID NO:27) which represent two of the reading frames for the TcHi10 sequence (shown in SEQ ID NO:5). The data is shown in FIG. 4. In the case of the TcLo frames, both the TcLo1.1 and 1.2 peptides were strongly reactive but the TcLo1.2 was superior in signal to noise when tested on sera from *T. cruzi* positive and negative individuals. TcLo1.3 had lower signal but also low background. In this study lysate detected 24/24 positives, TcLo1.1 detected 21/24, TcLo1.2 detected 23/24 and TcLo1.3 detected 15/24. In the same study, the two frames TcHi10.1 and 10.3 detected 19/24 and 14/24 positives respectively, but with lower signal than for TcLo1. Cross reactivity studies with these different reading frames demonstrate that TcLo1.2 has minimal cross reactivity with the sera tested (FIG. 5) as compared to *T. cruzi* lysate.

As discussed in Example 2, overlapping peptides were also synthesized for rTcc22 to determine the active epitope. The peptides Tcc22-1, 1+ and 2 were tested with *T. cruzi* positive and negative sera. The results are shown in FIG. 2. The Tcc22-1+ and Tcc22-2.1 peptides were more reactive than the Tcc22-1 peptide. In the first experiment, Tcc22-1 and Tcc22-1+ detected 29/48 and 36/48 positives as compared to the recombinant Tcc22 which detected 38/48 positives. In a subsequent experiment, Tcc22-2.1 was also shown to be reactive but with less signal than Tcc22-1+ at the same plate coating level.

A polypeptide having the TcH15 frame 3 repeat sequence (SEQ ID NO:49) was also synthesized and tested in an ELISA assay using a coating level of 200 ng/well. A total of 48 *T. cruzi* positive sera and 26 negative sera were tested in order to determine the reactivity of this peptide sequence. In this study, the peptide had a sensitivity of 68.75% (detecting 33 out of 48 positives) and a specificity of 92.3% (24 out of 36 negatives), indicating that this polypeptide has potential significance in detecting *T. cruzi* infections. The results of this assay are presented in Table 1, below.

TABLE 1

Reactivity of TcHi15 Frame 3 Polypeptide with *T. cruzi*-Positive and Negative Sera

| Sample ID | *T. cruzi* Status | OD 450 | Sample ID | *T. cruzi* Status | OD 450 |
|---|---|---|---|---|---|
| Tc011095-1 | Positive | 0.696 | DL4-0106 | Negative | 0.167 |
| Tc011095-2 | Positive | 0.699 | DL4-0112 | Negative | 0.05 |
| Tc011095-3 | Positive | 1.991 | DL4-0127 | Negative | 0.240 |
| Tc011095-4 | Positive | 3 | DL4-0140 | Negative | 0.008 |
| Tc011095-5 | Positive | 0.098 | DL4-0145 | Negative | 0.107 |
| Tc011095-6 | Positive | 0.238 | DL4-0161 | Negative | 0.119 |
| Tc011095-7 | Positive | 0.115 | DL4-0162 | Negative | 1.187 |
| Tc011095-8 | Positive | 0.156 | DL4-0166 | Negative | 0.210 |
| Tc011095-9 | Positive | 0.757 | DL4-0167 | Negative | 0.131 |
| Tc011095-10 | Positive | 1.147 | DL4-0172 | Negative | 0.073 |
| Tc011095-11 | Positive | 0.264 | DL4-0175 | Negative | 0.117 |
| Tc011095-12 | Positive | 1.7 | DL4-0176 | Negative | 0.815 |
| Tc011095-13 | Positive | 1.293 | AT4-0013 | Negative | 0.100 |
| Tc011095-14 | Positive | 0.242 | AT4-0041 | Negative | 0.107 |
| Tc011095-15 | Positive | 0.636 | AT4-0062 | Negative | 0.28 |
| Tc011095-16 | Positive | 0.44 | AT4-0063 | Negative | 0.155 |
| Tc011095-17 | Positive | 3 | E4-0051 | Negative | 0.162 |
| Tc011095-18 | Positive | 1.651 | E4-0059 | Negative | 0.176 |
| Tc011095-19 | Positive | 0.19 | E4-0068 | Negative | 0.241 |
| Tc011095-20 | Positive | 0.916 | E4-0071 | Negative | 0.127 |
| Tc011095-21 | Positive | 0.715 | C4-0072 | Negative | 0.101 |
| Tc011095-22 | Positive | 1.336 | C4-0088 | Negative | 0.141 |
| Tc011095-23 | Positive | 1.037 | C4-0090 | Negative | 0.078 |
| Tc011095-24 | Positive | 0.332 | C4-0096 | Negative | 0.162 |
| Tc011095-25 | Positive | 0.413 | C4-0101 | Negative | 0.181 |
| Tc011095-26 | Positive | 0.266 | C4-0105 | Negative | 0.702 |
| Tc011095-27 | Positive | 1.808 | | | |
| Tc011095-28 | Positive | 0.238 | | | |
| Tc011095-29 | Positive | 0.266 | | | |
| Tc011095-30 | Positive | 1.563 | | | |
| Tc011095-31 | Positive | 0.352 | Sensitivity | 33/48 | 68.75% |
| Tc011095-32 | Positive | 0.208 | Specificity | 24/26 | 92.30% |
| Tc011095-33 | Positive | 0.656 | Mean Pos. | 0.9188 | |
| Tc011095-34 | Positive | 1.281 | Std Dev Pos. | 0.79 | |
| Tc011095-35 | Positive | 0.907 | Mean Neg. | 0.1508 | |
| Tc011095-36 | Positive | 0.429 | Std Dev Neg. | 0.06695 | |
| Tc011095-37 | Positive | 0.454 | | | |
| Tc011095-38 | Positive | 0.725 | | | |
| Tc011095-39 | Positive | 0.703 | | | |
| Tc0394-7 | Positive | 0.186 | | | |
| Tc0394-8 | Positive | 1.06 | | | |
| Tc0394-9 | Positive | 1.813 | | | |
| Tc0394-10 | Positive | 0.131 | | | |
| Tc0394-11 | Positive | 1.631 | | | |
| Tc0394-12 | Positive | 0.613 | | | |
| Tc0394-13 | Positive | 3 | | | |
| Tc0394-14 | Positive | 0.268 | | | |
| Tc0394-15 | Positive | 2.211 | | | |

Example 5

Serological Reactivity of Peptide Combinations

This example illustrates the diagnostic properties of several peptide combinations.

The TcLo1.2 peptide (contained within SEQ ID NO:35) was tested in combination with the synthetic peptide TcD and also the dual epitope peptides D/2 (which contains the TcD and the PEP-2 sequences) and D/E (which contains TcD and TcE sequences). These combinations were compared with the individual peptides as well as the tripeptide 2/D/E, which contains TcD, TcE and PEP-2. The TcD sequence used was Ala Glu Pro Lys Ser Ala Glu Pro Lys Pro Ala Glu Pro Lys Ser (SEQ ID NO:53), the TcE sequence was Lys Ala Ala Ile Ala Pro Ala Lys Ala Ala Ala Ala Pro Ala Lys Ala Ala Thr Ala Pro Ala (SEQ ID NO:55), and the PEP2 sequence was Gly Asp Lys Pro Ser Pro Phe Gly Gln Ala Ala Ala Gly Asp Lys Pro Ser Pro Phe Gly Gln Ala (SEQ ID NO:57).

Figure 6:
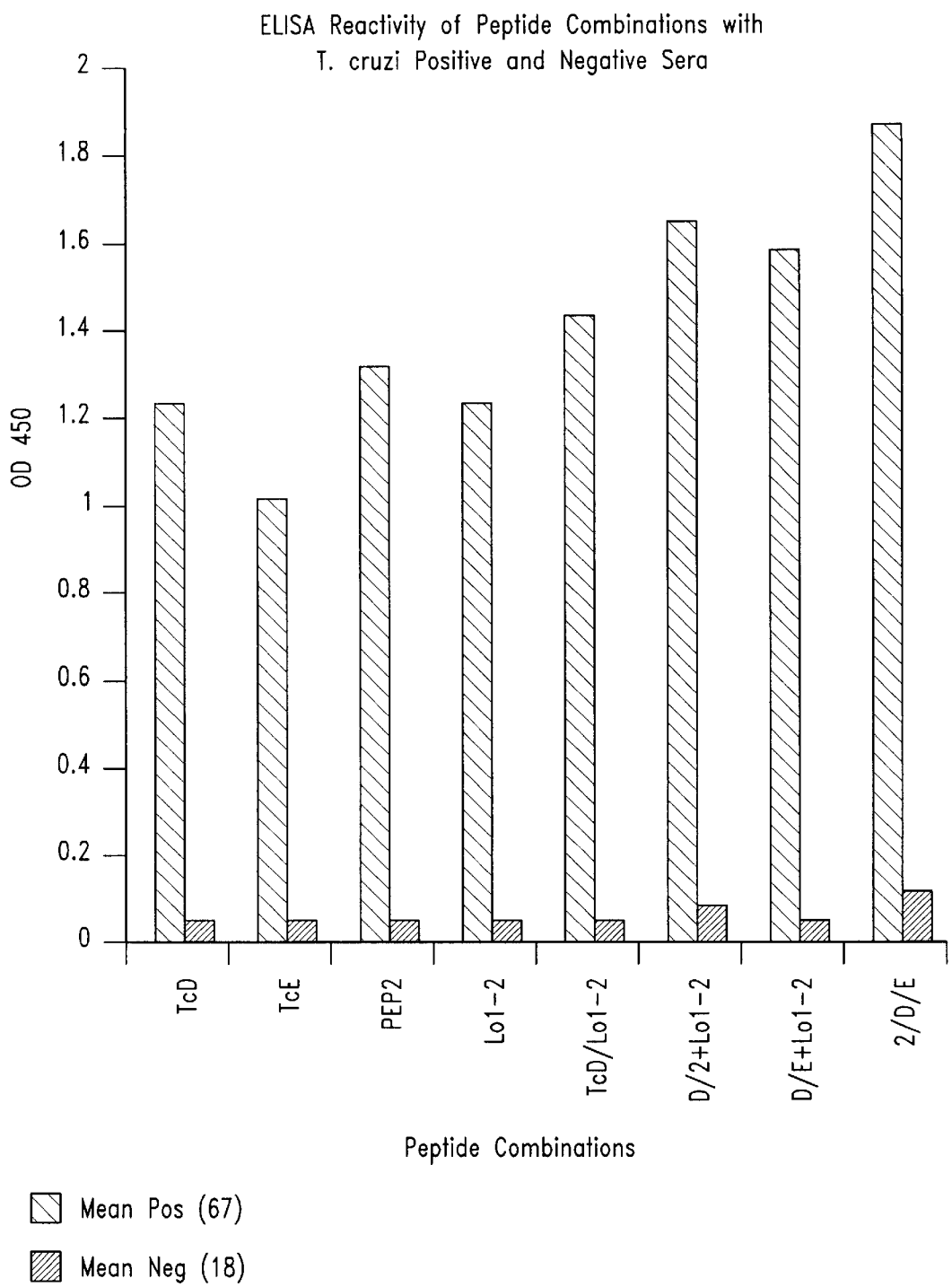
FIG. 6 is a graph depicting the ELISA reactivity of a series of polypeptide combinations with *T. cruzi* positive and negative sera.

The data are shown in FIG. 6. The results show that TcLo1.2 can augment the reactivity of TcD, D/2 and D/E, as summarized in Table 2.

TABLE 2

Sensitivity of Peptide Combinations in the Detection of *T. cruzi* Infection

| Peptides | Number of Positives |
|---|---|
| TcD | 62/67 |
| TcE | 50/67 |
| PEP-2 | 66/67 |
| TcLo1.2 | 61/67 |
| TcD + TcLo1.2 | 66/67 |
| D/2 + TcLo1.2 | 67/67 |
| D/E + TcLo1.2 | 67/67 |
| 2/D/E | 67/67 |

These results demonstrate the use of *T. cruzi* antigens as described herein to enhance the serodiagnostic properties of other antigens.

Example 6

Serological Reactivity of TcE Repeat Sequences

This example illustrates the diagnostic properties of several TcE repeat sequences.

The repeat sequence region of the recombinant TcE contains several degeneracies, resulting in residues where an A (alanine), T (threonine) or I (isoleucine) can be present in the repeat sequence. In order to represent all degeneracies, the original sequence for the synthetic TcE peptide was made with an A, T and I in a single peptide containing three repeats (see Example 5). In order to further epitope map the repeat region and to determine the number of repeats required for serological activity, the following peptides were prepared as described in Example 2:

```
original TcE  KAAIAPAKAAAAPAKAATAPA (SEQ ID NO: 55)

TcE(3A)       KAAAAPAKAAAAPAKAAAAPA (SEQ ID NO: 58)

TcE(3T)       KAATAPAKAATAPAKAATAPA (SEQ ID NO: 59)

TcE(3I)       KAAIAPAKAAIAPAKAAIAPA (SEQ ID NO: 60)

TcE(2A)       KAAAAPAKAAAAPA (SEQ ID NO:61)

TcE(AT)       KAAAAPAKAATAPA (SEQ ID NO:62)
```

Figure 7:
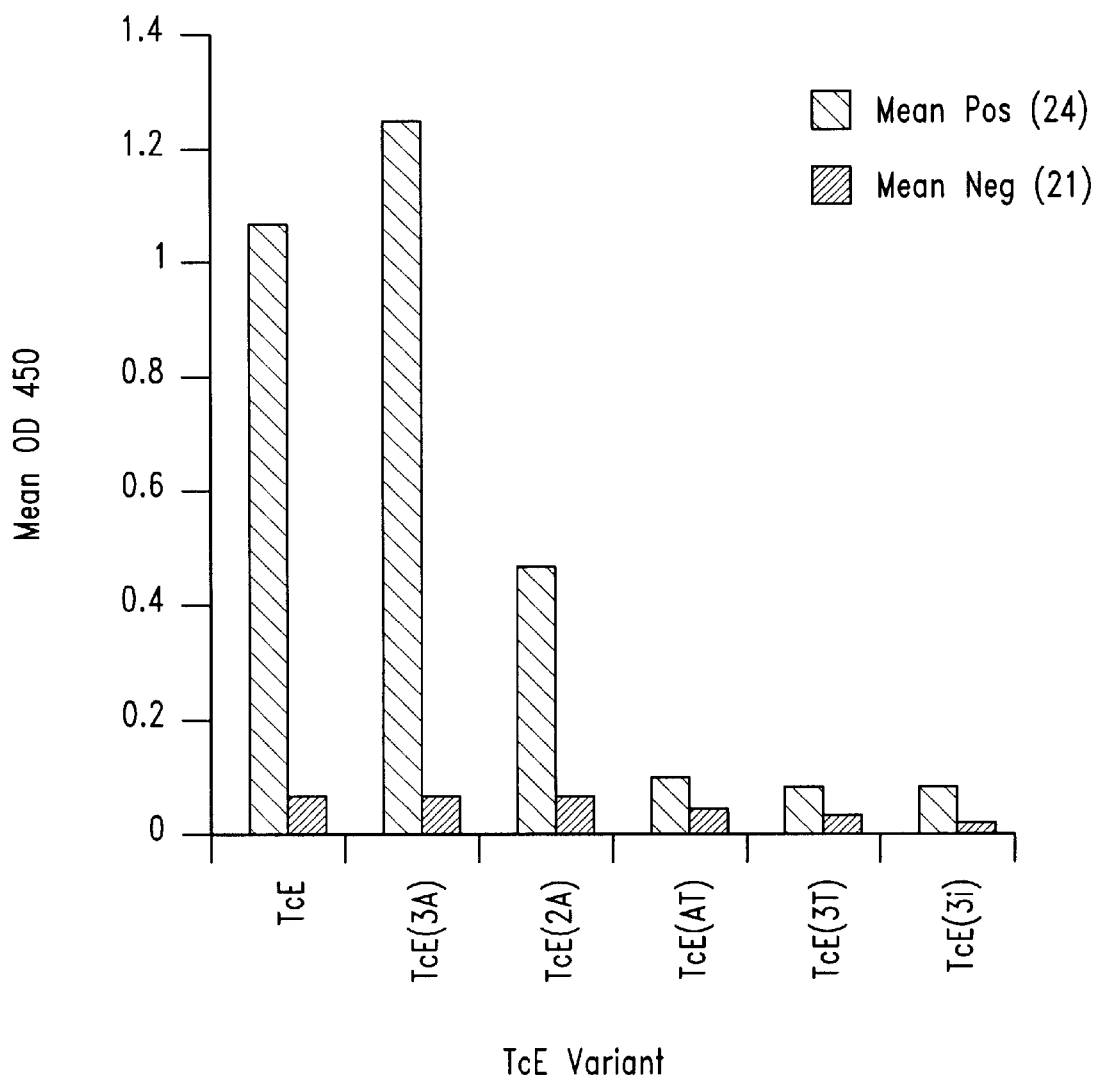
FIG. 7 is a graph presenting the ELISA reactivity of a series of TcE polypeptide variants with *T. cruzi* positive and negative sera.
Figure 8:
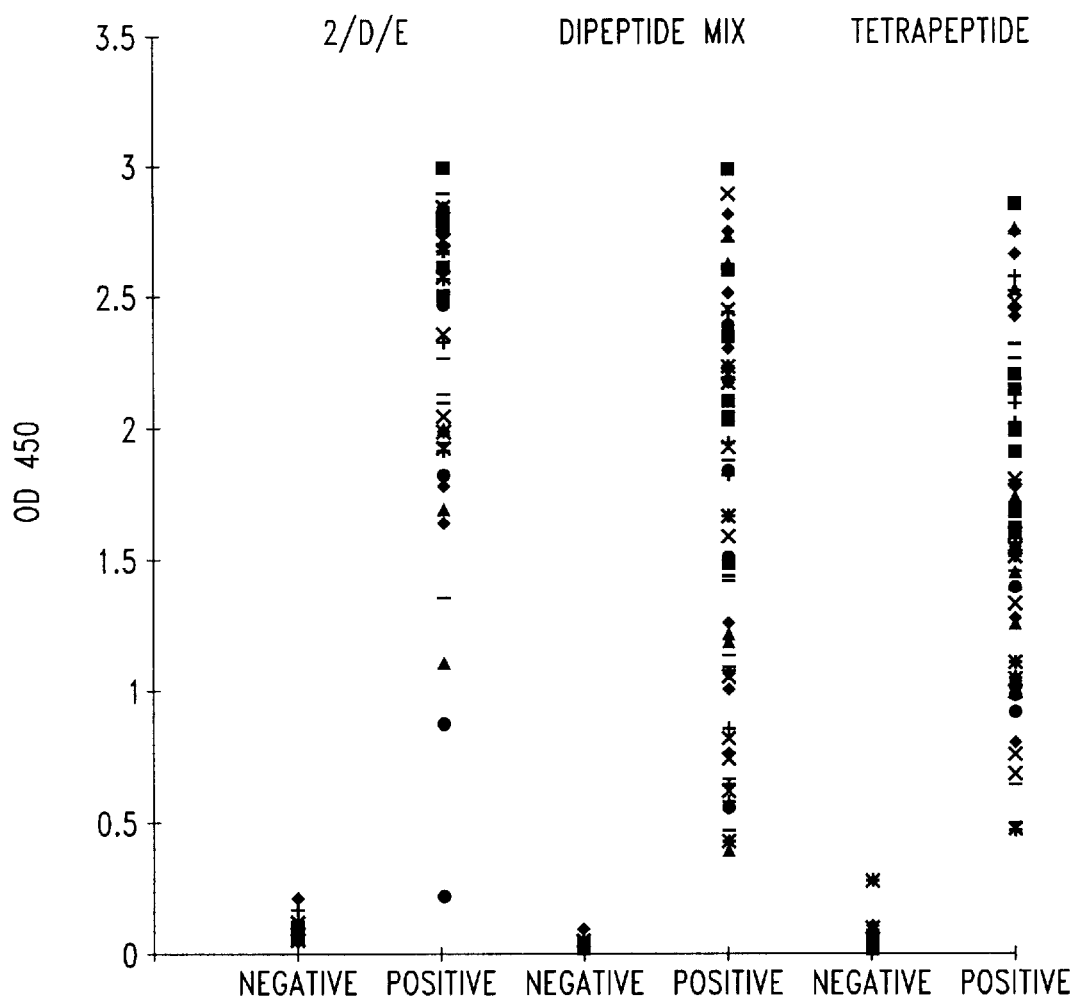
FIG. 8 is a graph comparing the ELISA reactivity of two dipeptides, a tripeptide and a tetrapeptide of the present invention with *T. cruzi* positive and negative sera.

The serological reactivity of these peptides was then compared. A total of 24 positive and 21 negative sera were tested with each of the TcE variants as the solid phase in an ELISA assay performed as described in Example 3, using 25 ng/well of peptide. The reactivity of the different peptides is shown in FIG. 7. The highest reactivity was seen with the 3-repeat peptide in which each repeat contained an A at the degenerate residue (TcE(3A)). This peptide displayed even higher reactivity than the original TcE sequence containing an A, T and I residue in the three repeats. The 3I and 3T variants by contrast were essentially negative with the *T. cruzi* positive samples tested. The sequence containing two repeats with A (TcE(2A)) was clearly less reactive than the 3A sequence and the two repeat sequence with an A and a T (TcE(AT)) was negative. Based on a cutoff of the mean of the negatives plus three standard deviations, the original TcE (A,T,I) detected 17 out of 24 positives and the 3A variant detected 19 out of 24 positives. It also appears that to obtain maximal serological activity at least three repeats are required.

Example 7

Serological Reactivity of Multi-epitope Peptide Combinations

This example illustrates the diagnostic properties of several multi-epitope peptide combinations.

Two dipeptides PEP-2/TcLo1.2, which contains the PEP-2 (SEQ ID NO:57) and TcLo1.2 (SEQ ID NO:35) sequences, and TcD/TcE, which contains the TcD (SEQ ID NO:53) and TcE (SEQ ID NO:55) sequences, were synthesized as described above in Example 2. The reactivity of these two dipeptides with *T. cruzi* antibody-positive sera was compared to that of the tripeptide 2/D/E. ELISA's were performed as described in Example 3 using PEP-2/TcLo1.2 at 250 ng/well and TcD/TcE at 50 ng/well. The results of this study are shown in FIG. 8. One *T. cruzi* positive serum found not to react with the tripeptide 2/D/E was used in screening for the TcLo1.2 epitope. This serum was detected by the TcLo1.2 epitope and also by the dipeptide mix (PEP-2/TcLo1.2 together with TcD/TcE) as expected.

A tetrapeptide containing the four immunoreactive *T. cruzi* epitopes PEP-2, TcD, TcE and TcLo1.2 in a linear sequence, herein after referred to as 2/Lo/2E/D (SEQ ID NO:63) was synthesized as described in Example 2. This tetrapeptide was coated at 100 ng/well and its reactivity with *T. cruzi* positive and negative sera was assayed as described in Example 3. The reactivity of the tetrapeptide 2/Lo/2E/D is shown in FIG. 8. The one *T. cruzi* positive serum found not to react with the tripeptide 2/D/E was detected by the tetrapeptide as expected.

The four immunoreactive *T. cruzi* epitopes PEP-2, TcD, TcE and TcLo1.2 may also be linked into one reagent by the use of a 'branched' peptide originating from a lysine core residue. Orthogonal protection of the lysine, for example employing 9-Fluorenylmethoxycarbonyl (Fmoc) on the α-amino group and 1-(4,4-Dimethyl-2,6-dioxocyclohex-1-ylidene)ethyl (Dde) on the ε-amino group, is used to permit selective deprotection of one amino group in the presence of the other, thereby allowing the synthesis of the first peptide chain from either the α- or ε-group on the lysine. This first peptide chain is terminated with a protecting group that is not removed during the course of the synthesis of the second peptide chain. For example, a tert-Butoxy carbonyl (Boc) amino acid could be used with the Dde and Fmoc combination. The remaining lysine amino protecting group is then removed before a second amino acid chain is synthesized from the second amino moiety. For example, ε-Dde is removed with 20% hydrazine. Cleavage of the branched peptide from a solid support and removal of the N-α-Boc moiety is carried out using trifluoroacetic acid, following standard protocols. Using this approach two independent amino acid sequences can be built from a 'core' lysine residue, as shown below, thus allowing various combinations of TcD, TcE, PEP2, TcLo1.2, and other epitopes to be coupled to the core residue. Purification of the resulting peptide is performed as described in Example 2.

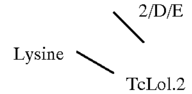

Example 8

Preparation of Multi-epitope Peptide Combinations using Recombinant DNA Technology This example illustrates the preparation of a fusion polypeptide (hereinafter referred to as TcF) of the peptides PEP-2 (SEQ ID NO:57), TcD (SEQ ID NO:53), TcE (SEQ ID NO:55) and TcLo1.2 (SEQ ID NO:35) using recombinant DNA technology.

The TcF polypeptide fusion was created by synthesizing overlapping phosphorylated oligonucleotides, annealing the matched oligonucleotide pairs to create double stranded DNA, ligating the annealed pairs with vector DNA that was cut with appropriate enzymes, and transforming into suitable bacteria host strains (XL2, Stratagene, La Jolla, Calif.) for sequencing. Once the correct sequence was obtained, the construct was subcloned into a modified pET28 vector and transformed into BLR pLYS S (Novagen, Madison, Wis.) for expression and purification.

For construction of the PEP2-TcD fusion, the matched pairs of oligonucleotides PDM-95 (SEQ ID NO:66) and PDM-98 (SEQ ID NO:67); PDM-96 (SEQ ID NO:68) and PDM-99 (SEQ ID NO:69); and PDM-97 (SEQ ID NO:70) and PDM-100 (SEQ ID NO:71) were synthesized, kinased and annealed. These three pairs of annealed oligos were then ligated, digested with EcoRI (New England Biolabs, Beverly, Mass.) and cloned into a modified T vector construct with Eco72I and EcoRI. For construction of the PEP2-TcD-TcE fusion, the following matched pairs of oligonucleotides were synthesized, kinased and annealed: PDM-103 (SEQ ID NO:72) and PDM-105 (SEQ ID NO:73); and PDM-104 (SEQ ID NO:74) and PDM-106 (SEQ ID NO:75). These two pairs of annealed oligos were ligated into the pT7ΔL2PEP2-TcD construct cut with Eco47III (New England Biolabs) and EcoRI.

For construction of the PEP2-TcD-TcE-Lo1.2 fusion, the two matched pairs of oligonucleotides PDM-108 (SEQ ID NO:76) and PDM-110 (SEQ ID NO:77); and PDM-109 (SEQ ID NO:78) and PDM-111 (SEQ ID NO:79) were synthesized, kinased and annealed. These two pairs of annealed oligonucleotides were ligated with the pT7ΔL2PEP2-TcD-TcE construct which had been cut with EagI, treated for blunt ends with T4 DNA polymerase and then cut with EcoRI. Due to an internal EagI site in the pT7ΔL2 vector, a PCR reaction was performed with the ligation mix as template in order to clone the full length PEP2-TcD-TcE-Lo1.2 construct. PCR was accomplished with the primers PDM-101 and PDM-107 (SEQ ID NOS:80 and 81, respectively) using the following conditions:

96° C. 2 minutes

96° C. 15 seconds 61° C. 15 seconds, 72° C. 1 minute×40 cycles

72° C. 4 minutes.

Pful DNA polymerase (Stratagene, La Jolla, Calif.) was used for the PCR reaction. Following PCR, the DNA was subjected to an ethanol precipitation, digested with SmaI and EcoRI, and ligated into a modified T vector construct which had been digested with Eco72I and EcoRI.

The resulting clone was digested with Hind III (Gibco BRL, Gaitherburg, Md.) and Sph I (New England Biolabs), treated with T4 DNA polymerase for blunt ends and then religated in order to delete the vector's internal Eag I and Nsi I sites. This new clone was then digested with Eag I and Nsi I, treated with T4 DNA polymerase for blund ends, and religated in order to create a stop codon in frame at the end of the TcLo1.2 sequence. This clone was digested with NdeI and Eco RI, and subcloned into a modified pET28b vector cut with the same enzymes.

The resulting expression construct was transformed into BLR pLys S *E. coli* (Novagen) and grown overnight in LB broth with kanamycin (30 ug/ml, Sigma, St. Louis, Mo.) and chloramphenicol (34 ug/ml Sigma). The overnight culture (12 ml) was used to inoculate 500 ml of 2XYT with the same antibiotics and the culture was induced at an OD560 of 0.3–0.6 with IPTG to a final concentration of 1.0 mM. Four hours post-induction, the bacteria were harvested and sonicated in 20 mM Tris (8.0), 100 mM NaCl, 0.1% DOC, 20 ug/ml Leupeptin and 20 mM PMSF followed by centrifugation at 26,000×g. The fusion protein was found in the soluble supernatant after sonication. The supernatant was bound to a Pro-bond nickel resin column (Invitrogen, Carlsbad, Calif.). The column was washed with 50 ml of 20 mM Tris (8.0), 100 mM NaCl wash buffer and eluted with an increasing imidazole concentration. Specifically, the elutions were made with 50 mM, 100 mM and 500 mM imidazole in the 20 mM Tris (8.0), 100 mM NaCl wash buffer. The eluates containing the protein of interest were pooled and dialyzed against 10 mM Tris (8.0).

After dialysis, the protein was concentrated, sterile filtered and tested for endotoxins. Test results indicated a high level of endotoxin contamination. The sterile filtered protein was therefore purified over a High Q anion exchange column (Biorad, Hercules, Calif.), binding in 10 mM Tris (8.0) and eluting with a NaCl gradient up to 1 M in 10 mM Tris (8.0). The elutions containing the protein of interest were pooled and dialyzed against 10 mM Tris (8.0). After dialysis, the protein was reconcentrated, sterile filtered and a BCA assay (Pierce, Rockford, Ill.) was performed to determine protein concentration. The determined amino acid sequence of TcF is provided in SEQ ID NO:82.

Figure 11:
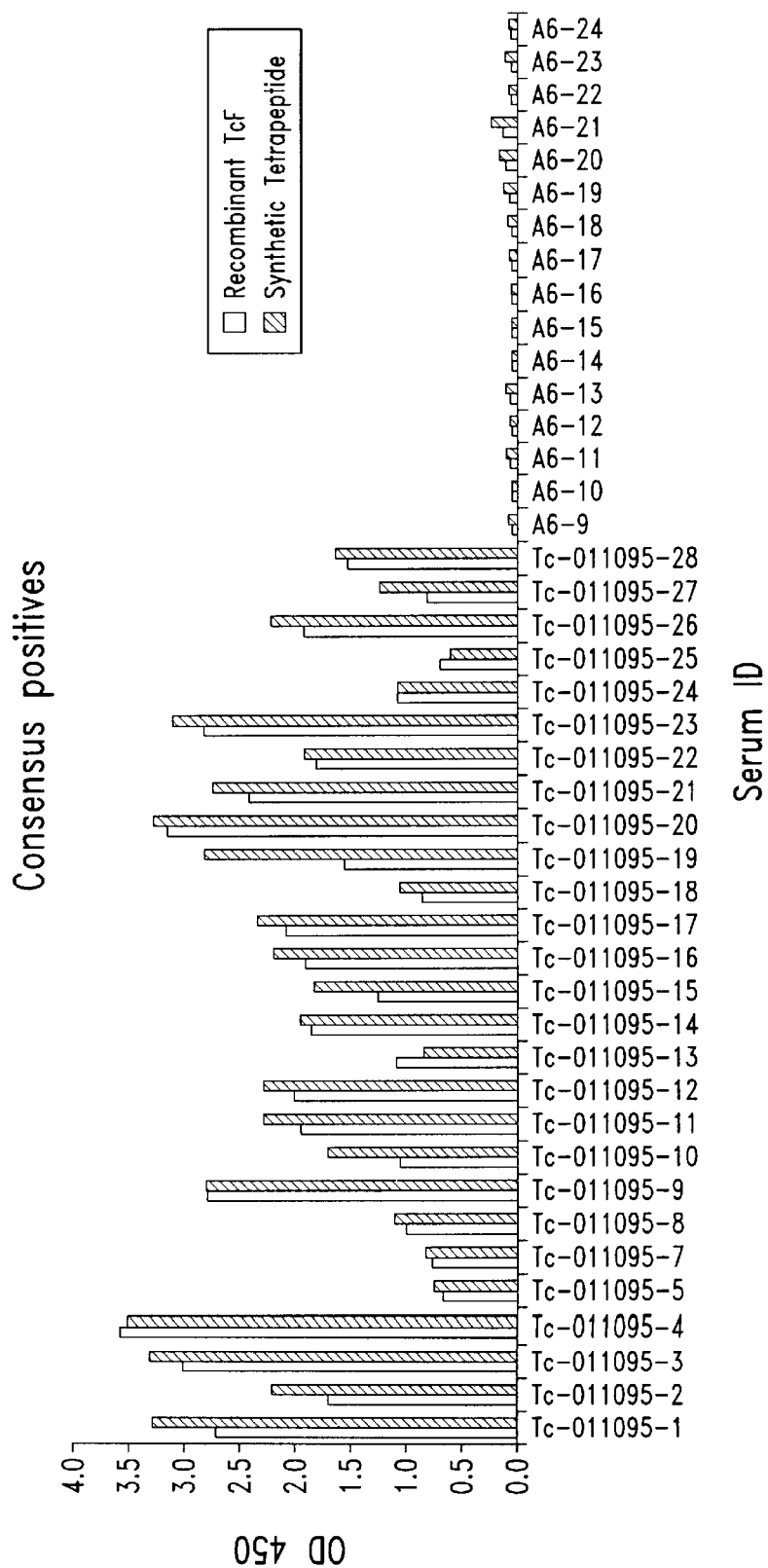
FIG. 11 is a graph comparing the ELISA reactivity of the recombinant fusion polypeptide TcF with sera from *T. cruzi* patients and from normal donors with the reactivity of the synthetic branched tetrapeptide 2/D/E/Lo1.2.

The reactivity of the recombinant fusion polypeptide TcF with sera from *T. cruzi* patients and from normal donors was examined by ELISA as described above. As shown in FIG. 11, the reactivity of TcF was found to be very similar to that of the branched synthetic tetrapeptide 2/D/E/Lo1.2.

It is envisioned that the order of the peptides in the recombinant fusion polypeptide TcF could be altered without significantly changing the activity of the polypeptide. Also, the inclusion of a Gly-Cys-Gly linkage between the peptides may enhance solid phase binding without significantly affecting the activity of the polypeptide.

A fusion polypeptide (hereinafter referred to as TcF-2) of the peptides PEP-2 (SEQ ID NO:57), TcD (SEQ ID NO:53), TcE (SEQ ID NO:55) and TcLo1.2 (SEQ ID NO:35) with a glycine-cysteine-glycine amino acid spacer between each of the fused peptides was prepared by synthesizing overlapping phosphorylated oligos, annealing the matched oligo pairs to create double-stranded DNA, ligating the annealed pairs with vector DNA that was cut with appropriate enzymes and transformed into suitable bacterial host strains for sequencing (XL2, Stratagene). Once the correct sequence was obtained, the construct was subcloned into a modified pET28 vector and transformed into BLR pLYS S (Novagen, Madison, Wis.) for expression and purification.

More specifically, the PEP2-GCG-TcD fusion was constructed by synthesizing, kinasing and annealing the following matched pairs of oligos: PDM-95 (SEQ ID NO:66) and PDM-98 (SEQ ID NO:67); PDM-112 (SEQ ID NO:83) and PDM-113 (SEQ ID NO:84); and PDM-114 (SEQ ID NO:85) and PDM-115 (SEQ ID NO:86). The three pairs of annealed oligos were ligated, digested with EcoRI (New England Biolabs, Beverly, Mass.) and cloned into a modified pT7 blue construct with a His tag in frame when cut with Eco 72I and EcoRI. For construction of the PEP2-GCG-TcD-GCG-TcE fusion, the following matched pairs of oligos were synthesized, kinased and annealed: PDM-116 (SEQ ID NO:87) and PDM-117 (SEQ ID NO:88); and PDM-118 (SEQ ID NO:89) and PDM-119 (SEQ ID NO:90). These two pairs of matched oligos were then ligated into the above PEP2-GCG-TcD construct cut with Eco 47III (New England Labs.) and Eco RI.

The matched pairs of oligos PDM-120 (SEQ ID NO:92) and PDM-121 (SEQ ID NO:92), and PDM-122 (SEQ ID NO:93) and PDM-123 (SEQ ID NO:94) were synthesized, kinased and annealed, and then ligated with the above PEP2-GCG-TcD-GCG-TcE construct which had been cut with Eag I, treated for blunt ends with T4 DNA polymerase and then cut with Eco RI. This clone was then digested with Nde I (Gibco BRL) and Eco RI, and subcloned into a modified pET28 vector cut with the same enzymes.

The expression construct was then transformed to BLR pLys S *E. coli* (Novagen) and grown overnight in LB broth with kanamycin (30 ug/ml, Sigma, St. Louis, Mo.) and chloramphenicol (34 ug/ml, Sigma). 12 ml of the overnight culture was used to inoculate 500 ml of 2XYT with the same antibiotics and the culture was induced at an OD560 of 0.37 with IPTG to a final concentration of 1.0 mM. Four hours post-induction, the bacteria were harvested and sonicated in 20 mM Tris (8.0), 100 mM NaCl, 0.1% DOC, 20 ug.ml leupeptin, 20 mM PMSF followed by centrifugation at 26,000×g. The fusion protein was found in the soluble supernatant after sonication. The supernatant was then bound to Pro-bond nickel resin (Invitrogen, Carlsbad, Calif.). The column was washed with 50 ml of 20 mM Tris (8.0), 100 mM NaCl wash buffer and then eluted with an increasing imidazole concentration. The elutions were made with 50 mM, 100 mM and 500 mM imidazole in the 20 mM Tris (8.0), 100 mM NaCl wash buffer. The eluates containing the protein of interest were pooled and then dialyzed against 10 mM Tris (8.0).

After dialysis, the protein was taken over a High Q (Biorad, Hercules, Calif.) anion exchange column, binding in 10 mM Tris (8.0) and eluting with a NaCl gradient up to 1 M in 10 mM Tris (8.0). The elutions containing the protein of interest were pooled and dialyzed against 10 mM Tris (8.0). After dialysis, the protein was reconcentrated and sterile filtered, and a BCA assay (Pierce) was performed to determine protein concentration. The determined amino acid sequence for TcF-2 is provided in SEQ ID NO:95).

Example 9

Comparison of the Serological Reactivity of TcHi29 and TcE

The antigen TcHi29 (SEQ ID NO:52) was shown to be a polymorph of the TcE repeat sequence. A TcHi29 peptide was synthesized that had the following sequence as compared to TcE.

```
TcE      KAAIAPAKAAAAPAKAATAPA (SEQ ID NO: 55)

TcHi29   KTAAPPAKTAAPPAKTAAPPA (SEQ ID NO: 64)
```

Figure 9:
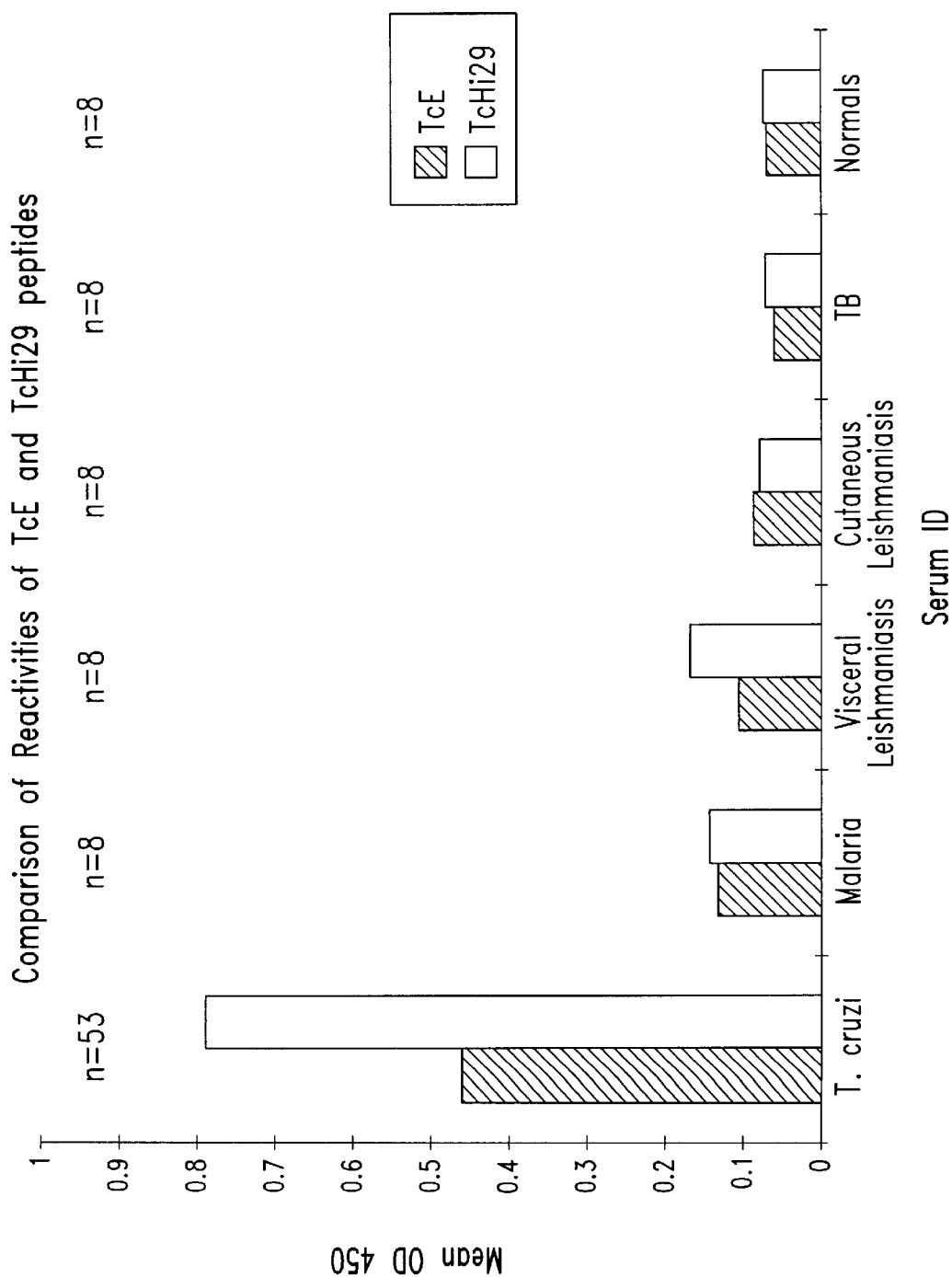
FIG. 9 is a graph presenting the ELISA reactivity of a representative polypeptide of the present invention (TcHi29) and of TcE with sera from normal individuals, *T. cruzi* patients, and patients with other diseases.
Figure 10:
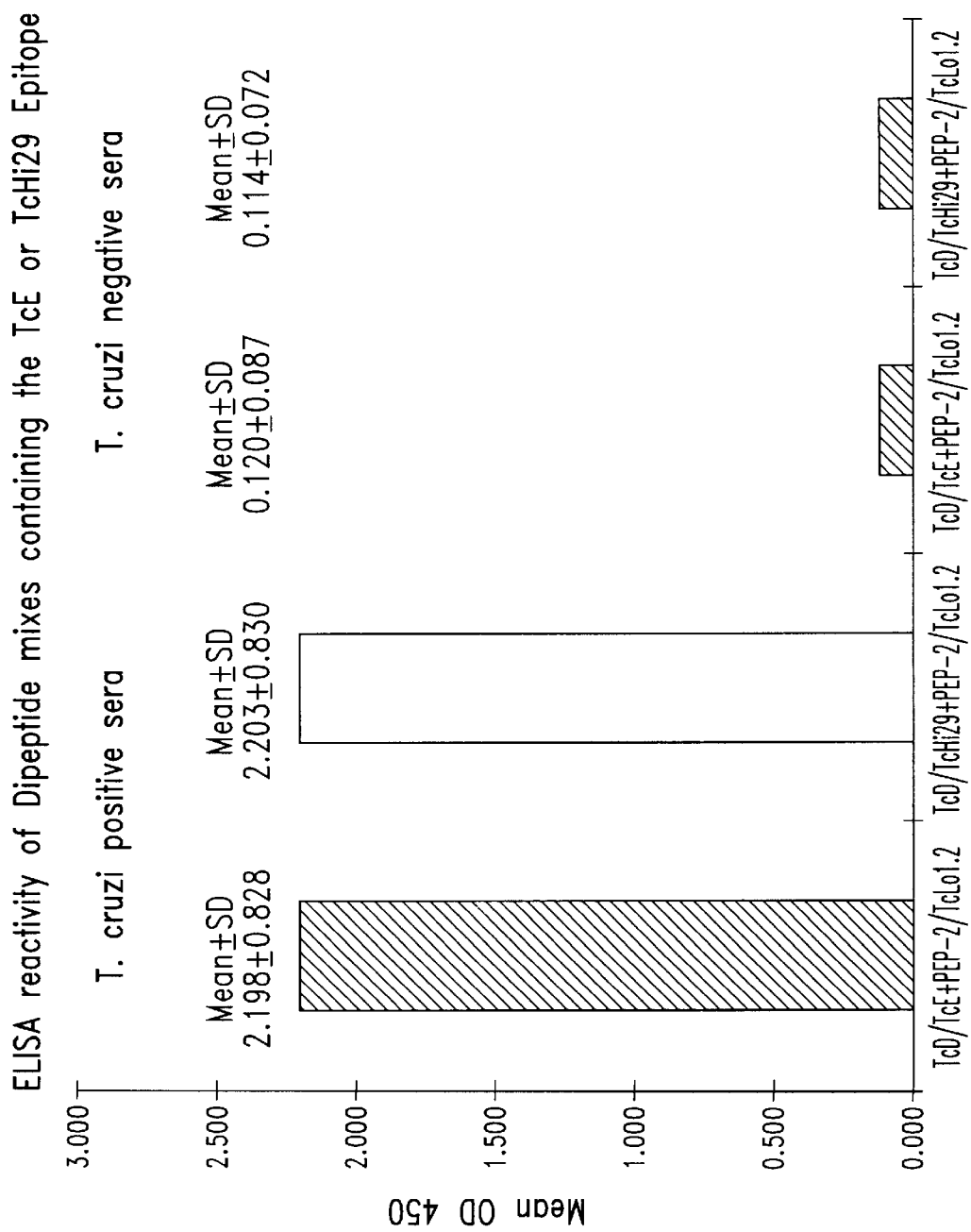
FIG. 10 is a graph comparing the ELISA reactivity of two representative dipeptide mixtures with *T. cruzi* positive and negative sera, one mixture including a TcE epitope and the other including a TcHi29 epitope of the present invention.

FIG. 9 shows a comparison of the reactivity of these two related seqences with sera from *T. cruzi* positive patients as well as from other disease categories, as determined by ELISA using the procedure described above. The data indicate little or no cross reactivity with the other disease groups tested but the distribution of reactivity amongst the *T. cruzi* positive sera partially overlapped for the two peptides. Of the 53 consensus positive samples tested, TcE detected 31/53 and TcHi 29 36/53. Within this group TcE and TcHi29 both detected 24 of the same sera. TcE detected 7 positive sera not detected by TcHi29, which in turn detected 12 positive sera missed by TcE. A dipeptide, TcD/TcHi29, was also synthesized and used in combination with the PEP-2/TcLo1.2 dipeptide in ELISA (100 ng/well TcD/TcHi29, 250 ng/well PEP-2/TcLo1.2) and compared with the TcD/TcE plus PEP-2/TcLo1.2 dipeptide combination. As shown in FIG. 10, the data indicates that the overall activity of the two mixes are similar for both the *T. cruzi* positive and negative populations studied and suggests that, in such peptide combinations, TcHi29 can be considered to be an alternative to TcE.

From the foregoing, it will be appreciated that, although specific embodiments of the invention have been described herein for the purpose of illustration, various modifications may be made without deviating from the spirit and scope of the invention.

What is claimed is:

1. A combination polypeptide comprising at least two amino acid sequences, wherein at least one of the amino acid sequences comprises SEQ ID NO:35.

2. A combination polypeptide comprising SEQ ID NO:35, wherein the combination polypeptide further comprises SEQ ID NO:82.

3. A combination polypeptide comprising SEQ ID NO:35, wherein the combination polypeptide further comprises SEQ ID NO:95.

4. A combination polypeptide according to claim 1, wherein the combination polypeptide is prepared using recombinant DNA technology.

5. A combination polypeptide according to claim 1, wherein the combination polypeptide is prepared synthetically.

6. A combination polypeptide according to claim 1, further comprising the sequence of SEQ ID NO:53.

7. A combination polypeptide according to claim 1, further comprising the sequence of SEQ ID NO:55.

8. A combination polypeptide according to claim 1, further comprising the sequence of SEQ ID NO:57.

* * * * *